US009579390B2

(12) United States Patent
Kudirka et al.

(10) Patent No.: US 9,579,390 B2
(45) Date of Patent: Feb. 28, 2017

(54) COMPOUNDS AND METHODS FOR PRODUCING A CONJUGATE

(71) Applicant: Redwood Bioscience, Inc., Emeryville, CA (US)

(72) Inventors: Romas Alvydas Kudirka, Berkeley, CA (US); Aaron Edward Albers, San Francisco, CA (US); David Rabuka, Kensington, CA (US)

(73) Assignee: Redwood Bioscience, Inc., Emeryville, CA (US)

( * ) Notice: Subject to any disclaimer, the term of this patent is extended or adjusted under 35 U.S.C. 154(b) by 0 days.

(21) Appl. No.: 14/704,802

(22) Filed: May 5, 2015

(65) Prior Publication Data

US 2016/0038602 A1 Feb. 11, 2016

Related U.S. Application Data

(63) Continuation of application No. PCT/US2013/059267, filed on Sep. 11, 2013.

(60) Provisional application No. 61/725,405, filed on Nov. 12, 2012.

(51) Int. Cl.
*A61K 38/10* (2006.01)
*A61K 47/48* (2006.01)
*A61K 49/00* (2006.01)
*C07D 231/20* (2006.01)
*C07D 405/04* (2006.01)
*C07K 16/22* (2006.01)
*C07K 16/40* (2006.01)
*C12N 9/12* (2006.01)
*C12N 9/96* (2006.01)
*G01N 33/533* (2006.01)

(52) U.S. Cl.
CPC ......... *A61K 47/48061* (2013.01); *A61K 38/10* (2013.01); *A61K 47/48215* (2013.01); *A61K 47/48384* (2013.01); *A61K 47/48584* (2013.01); *A61K 47/48715* (2013.01); *A61K 49/0041* (2013.01); *A61K 49/0058* (2013.01); *C07D 231/20* (2013.01); *C07D 405/04* (2013.01); *C07K 16/22* (2013.01); *C07K 16/40* (2013.01); *C12N 9/12* (2013.01); *C12N 9/96* (2013.01); *G01N 33/533* (2013.01); *C12Y 207/10001* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,816,567 A | 3/1989 | Cabilly et al. |
| 4,935,496 A | 6/1990 | Kudo et al. |
| 5,075,046 A | 12/1991 | Stoll |
| 5,089,261 A | 2/1992 | Nitecki et al. |
| 5,100,992 A | 3/1992 | Cohn et al. |
| 5,134,192 A | 7/1992 | Feijen et al. |
| 5,166,309 A | 11/1992 | Maj et al. |
| 5,171,264 A | 12/1992 | Merrill |
| 5,200,534 A | 4/1993 | Rao |
| 5,202,448 A | 4/1993 | Carver et al. |
| 5,213,891 A | 5/1993 | Maj et al. |
| 5,219,564 A | 6/1993 | Zalipsky et al. |
| 5,225,539 A | 7/1993 | Winter |
| 5,229,529 A | 7/1993 | Ueno et al. |
| 5,274,137 A | 12/1993 | Nicolaou et al. |
| 5,275,838 A | 1/1994 | Merrill |
| 5,279,949 A | 1/1994 | Nair |
| 5,281,698 A | 1/1994 | Nitecki |
| 5,283,253 A | 2/1994 | Holton et al. |
| 5,294,637 A | 3/1994 | Chen et al. |
| 5,298,643 A | 3/1994 | Greenwald |
| 5,312,808 A | 5/1994 | Shorr et al. |
| 5,321,095 A | 6/1994 | Greenwald |
| 5,324,844 A | 6/1994 | Zalipsky |
| 5,349,001 A | 9/1994 | Greenwald et al. |
| 5,352,756 A | 10/1994 | Meldal |
| 5,393,895 A | 2/1995 | Gaullier et al. |
| 5,393,896 A | 2/1995 | Margraff |
| 5,405,877 A | 4/1995 | Greenwald et al. |
| 5,415,869 A | 5/1995 | Straubinger et al. |
| 5,446,090 A | 8/1995 | Harris |
| 5,455,027 A | 10/1995 | Zalipsky et al. |
| 5,470,829 A | 11/1995 | Prisell |
| 5,478,805 A | 12/1995 | Shorr et al. |

(Continued)

FOREIGN PATENT DOCUMENTS

EP 0208874 1/1987
EP 239400 9/1987

(Continued)

OTHER PUBLICATIONS

Angelastro et al. ('Inhibition of Human Neutrophil Elastase with Peptidyl Electrophilic Ketones. 2. Orally Active PG-Val-Pro-Val Pentafluoroethyl Ketones' J. Med. Chem. v37 1994 pp. 4538-4554).*

Mass Spectrometry (retrieved from http://www2.chemistry.msu.edu/faculty/reusch/virttxtjml/spectrpy/massspec/masspec1.htm on Apr. 14, 2016, 9 pages).*

Aly et al. (1994) "X Y—ZH Compounds as potential 1,3-Dipoles.: Part 41. Azomethine ylide formation from the reactions of α-amino acids and esters with alloxan (strecker degradation) and with 1-phenyl-3-methylpyrazolin-4,5-dione," *Tetrahedron*, 50(3): 895-906.

(Continued)

*Primary Examiner* — Karlheinz R Skowronek
*Assistant Examiner* — Ronald Niebauer
(74) *Attorney, Agent, or Firm* — Rudy J. Ng; Carol L. Francis; Bozicevic, Field & Francis LLP

(57) ABSTRACT

The present disclosure provides conjugate structures and compound structures used to produce these conjugates. The disclosure also encompasses methods of production of such conjugates, as well as methods of using the same.

10 Claims, 44 Drawing Sheets

(56) References Cited

U.S. PATENT DOCUMENTS

| | | | |
|---|---|---|---|
| 5,502,167 | A | 3/1996 | Waldmann et al. |
| 5,530,101 | A | 6/1996 | Queen et al. |
| 5,558,864 | A | 9/1996 | Bendig et al. |
| 5,565,332 | A | 10/1996 | Hoogenboom et al. |
| 5,567,422 | A | 10/1996 | Greenwald |
| 5,585,089 | A | 12/1996 | Queen et al. |
| 5,605,976 | A | 2/1997 | Martinez et al. |
| 5,612,460 | A | 3/1997 | Zalipsky |
| 5,614,549 | A | 3/1997 | Greenwald et al. |
| 5,618,528 | A | 4/1997 | Cooper et al. |
| 5,637,749 | A | 6/1997 | Greenwald |
| 5,643,575 | A | 7/1997 | Martinez et al. |
| 5,650,388 | A | 7/1997 | Shorr et al. |
| 5,672,662 | A | 9/1997 | Harris et al. |
| 5,681,567 | A | 10/1997 | Martinez et al. |
| 5,686,110 | A | 11/1997 | Greenwald et al. |
| 5,693,493 | A | 12/1997 | Robinson et al. |
| 5,698,417 | A | 12/1997 | Robinson et al. |
| 5,705,154 | A | 1/1998 | Dalie et al. |
| 5,717,103 | A | 2/1998 | Denis et al. |
| 5,730,990 | A | 3/1998 | Greenwald et al. |
| 5,739,208 | A | 4/1998 | Harris |
| 5,750,078 | A | 5/1998 | Shitara et al. |
| 5,756,593 | A | 5/1998 | Martinez et al. |
| 5,770,403 | A | 6/1998 | Dalie et al. |
| 5,808,096 | A | 9/1998 | Zalipsky |
| 5,821,263 | A | 10/1998 | Scola et al. |
| 5,824,701 | A | 10/1998 | Greenwald et al. |
| 5,824,778 | A | 10/1998 | Ishikawa et al. |
| 5,824,784 | A | 10/1998 | Kinstler et al. |
| 5,840,699 | A | 11/1998 | Sakakibara et al. |
| 5,840,900 | A | 11/1998 | Greenwald et al. |
| 5,869,680 | A | 2/1999 | Mas et al. |
| 5,874,500 | A | 2/1999 | Rhee et al. |
| 5,880,131 | A | 3/1999 | Greenwald et al. |
| 5,900,461 | A | 5/1999 | Harris |
| 5,902,588 | A | 5/1999 | Greenwald et al. |
| 5,919,442 | A | 7/1999 | Yin et al. |
| 5,919,455 | A | 7/1999 | Greenwald et al. |
| 5,932,462 | A | 8/1999 | Harris et al. |
| 5,965,119 | A | 10/1999 | Greenwald et al. |
| 5,965,566 | A | 10/1999 | Greenwald et al. |
| 5,985,263 | A | 11/1999 | Lee et al. |
| 6,136,808 | A | 10/2000 | Abe et al. |
| 6,306,893 | B1 | 10/2001 | Mandai et al. |
| 6,323,315 | B1 | 11/2001 | Pettit et al. |
| 6,570,040 | B2 | 5/2003 | Saxon et al. |
| 7,985,783 | B2 | 7/2011 | Carrico et al. |
| 8,163,757 | B2 | 4/2012 | Matthews |
| 2004/0086979 | A1 | 5/2004 | Zhang et al. |
| 2005/0033031 | A1 | 2/2005 | Couto |
| 2012/0183566 | A1 | 7/2012 | Barfield et al. |

FOREIGN PATENT DOCUMENTS

| | | |
|---|---|---|
| EP | 519596 | 12/1992 |
| EP | 590267 | 4/1994 |
| EP | 592106 | 4/1994 |
| EP | 1391213 | 2/2004 |
| EP | 1983033 | 10/2008 |
| GB | 2373789 | 10/2002 |
| JP | 2010169666 | 8/2010 |
| WO | WO 9013540 | 11/1990 |
| WO | WO 9109967 | 7/1991 |
| WO | WO 9200748 | 1/1992 |
| WO | WO 9216555 | 10/1992 |
| WO | WO 9310076 | 5/1993 |
| WO | WO 9323555 | 11/1993 |
| WO | WO 9404193 | 3/1994 |
| WO | WO 9407880 | 4/1994 |
| WO | WO 9414758 | 7/1994 |
| WO | WO 9417039 | 8/1994 |
| WO | WO 9418247 | 8/1994 |
| WO | WO 9428937 | 12/1994 |
| WO | WO 9511924 | 5/1995 |
| WO | WO 9513312 | 5/1995 |
| WO | WO 9600080 | 1/1996 |
| WO | WO 9614856 | 5/1996 |
| WO | WO 9621469 | 7/1996 |
| WO | WO 9623794 | 8/1996 |
| WO | WO 9703106 | 1/1997 |
| WO | WO 9807713 | 2/1998 |
| WO | WO 9813059 | 4/1998 |
| WO | WO 9822451 | 5/1998 |
| WO | WO 9828288 | 7/1998 |
| WO | WO 9841562 | 9/1998 |
| WO | WO 9845331 | 10/1998 |
| WO | WO 9845332 | 10/1998 |
| WO | WO 9848837 | 11/1998 |
| WO | WO 9858927 | 12/1998 |
| WO | WO 9909021 | 2/1999 |
| WO | WO 9930727 | 6/1999 |
| WO | WO 9932134 | 7/1999 |
| WO | WO 9933483 | 7/1999 |
| WO | WO 9945964 | 9/1999 |
| WO | WO 9953951 | 10/1999 |
| WO | WO 0126692 | 4/2001 |
| WO | 2006129524 | 12/2006 |
| WO | WO 2011/038874 | * 4/2011 |
| WO | 2011085039 | 7/2011 |

OTHER PUBLICATIONS

Eggink et al. (2009) "Detailed Mechanistic Insights into HIV-1 Sensitivity to Three Generations of Fusion Inhibitors," *J. Biol. Chem.*; 284:26941-26950.

Fridman (1991) "Fc receptors and immunoglobulin binding factors," *FASEB*; 5(12):2684-2690.

Graham, et al., (1954) "The Reaction of 1-Substituted-3-amino-5-pyrazolones with Amines," *JACS*, 76:3993-3995.

Liu et al. (1996) "Eradication of large colon tumor xenografts by targeted delivery of maytansinoids," *PNAS*; 93(16):8618-8623.

Matos et al. (2010) "HIV-1 Fusion Inhibitor Peptides Enfuvirtide and T-1249 Interact with Erythrocyte and Lymphocyte Membranes," *PLoS One*; 5:e9830.

Padlan (1991) "A possible procedure for reducing the immunogenicity of antibody variable domains while preserving their ligand-binding properties," *Mol. Immun.* 28(4/5):489-498.

Reim, et. al., (2008) "Synthesis and solution structure of 3,5-dioxopimelic acid diesters-stable 1,3,5,7-tetracarbonyl derivatives," *Org. Biomol. Chem.*; 6:3079-3084.

Riechmann et al. (1988) "Reshaping human antibodies for therapy," *Nature*; 332:323.

Roguska et al. (1994) "Humanization of murine monoclonal antibodies through variable domain resurfacing," *PNAS*; 91:969-973.

Studnicka et al. (1994) "Human-engineered monoclonal antibodies retain full specific binding activity by preserving non-CDR complementarity-modulating residues," *Protein Engineering*; 7(6):805-814.

Jones (1949) "The Synthesis of Some Amines and Amino Acids Containing the Pyrazole Nucleus," *J.Am.Chem.Soc.*; 71(12):3994-4000.

Kakiuchi et al. (2004) "A novel pyrazolone, 4.4-dichloro-1-(2.4-dichlorophenyl)-3-methyl-5-pyrazolone, as a potent catalytic inhibitor of human telomerase," *Biochem Biophys Res Commun.*: 320(4):1351-1358.

Rabuka et al. (2012) "Site-specific chemical protein conjugation using genetically encoded aldehyde tags," *Nature Protocols*; 7(6)1052-1067.

You et al. (2008) "Detection of carbohydrates using new labeling reagent 1-(2-naphthyl)3-methyl-5-pyrazolone by capillary zone electrophoresis with absorbance (UV)," *Analytica Chimica Acta*: 609:66-75.

\* cited by examiner

B
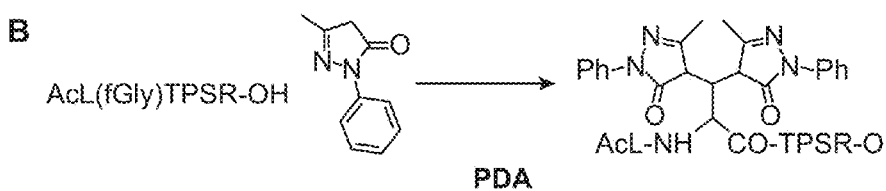
AcL(fGly)TPSR-OH
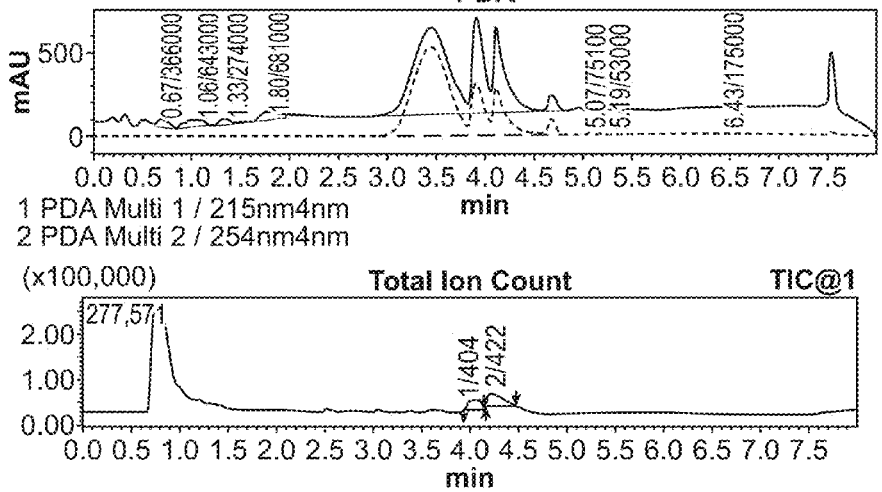
1 PDA Multi 1 / 215nm4nm
2 PDA Multi 2 / 254nm4nm
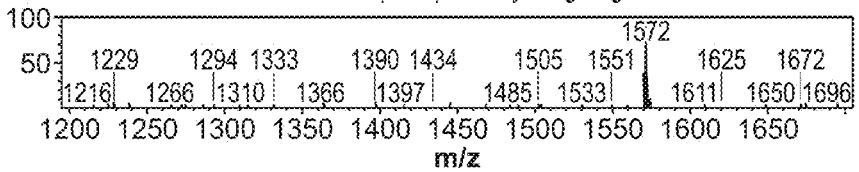
MS Spectrum Graph
1
:1 Ret.Time:Averaged 4.040-4.048(Scan#:1011-1013)
BG Mode:Calc 3.928<->4.144(083<->1037)
Mass Peaks:188 Base Peak:1571.70(7004) Polarity: Neg Segment1 - Event1
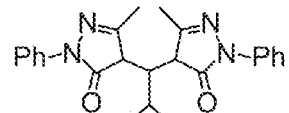
2
:2 Ret.Time:Averaged 4.216-4.224(Scan#:1055-1057)
BG Mode:Calc 4.164<->4.456(1042<->1115)
Mass Peaks:184 Base Peak:1572.00(10658) Polarity: Neg Segment1 - Event1
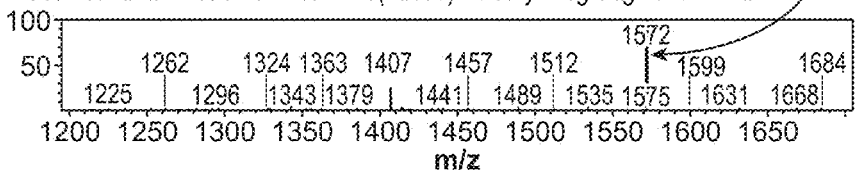
FIG. 3 (Cont. 1)

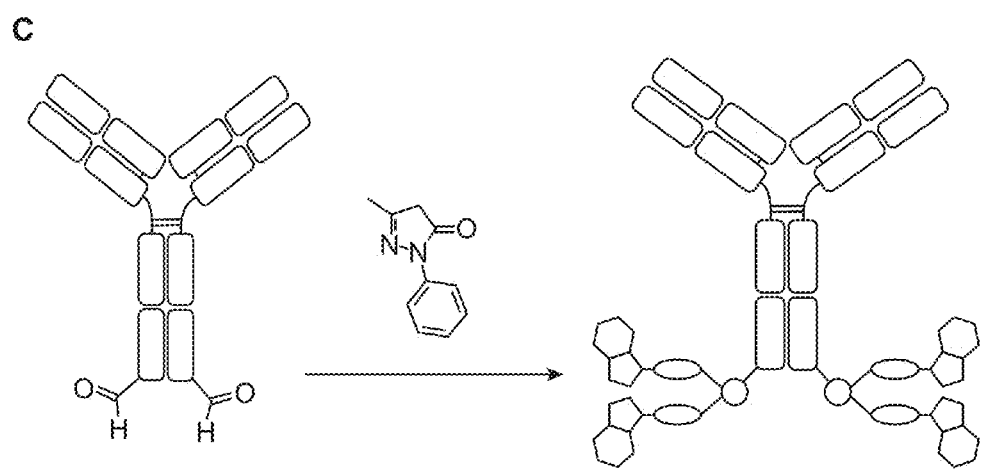
FIG. 3 (Cont. 2)

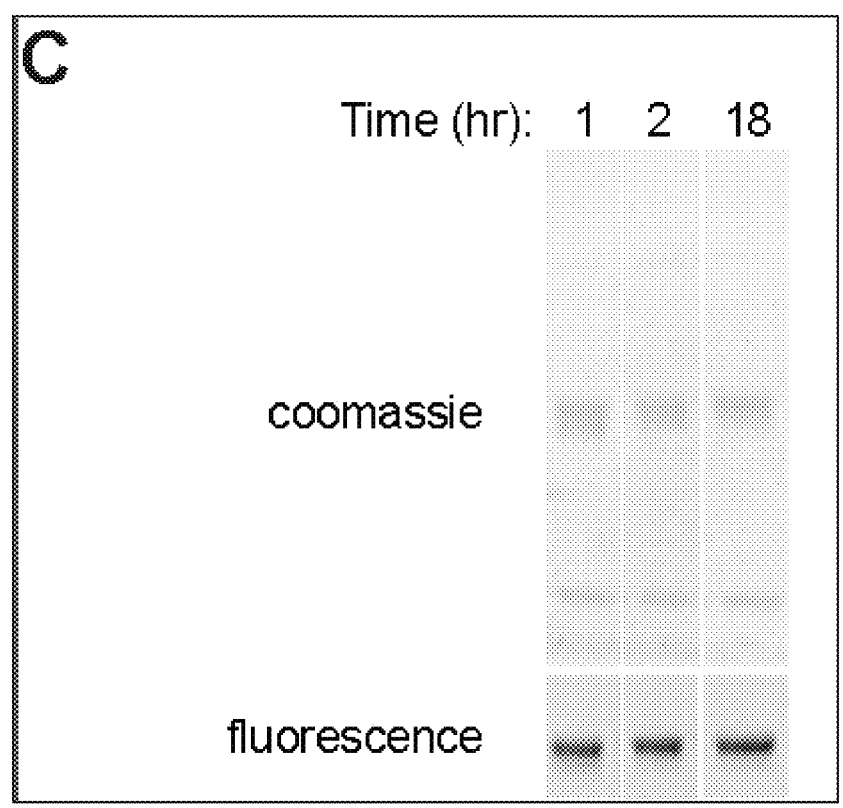
FIG. 5, continued

FIG. 9B

COMPOUNDS AND METHODS FOR PRODUCING A CONJUGATE

CROSS-REFERENCE TO RELATED APPLICATIONS

This application is a continuation of PCT Application No. PCT/US2013/059267, filed Sep. 11, 2013, which claims the benefit of U.S. Provisional Application No. 61/725,405, filed Nov. 12, 2012, the disclosures of each of which are incorporated herein by reference.

INTRODUCTION

The field of protein-small molecule therapeutic conjugates has advanced greatly, providing a number of clinically beneficial drugs with the promise of providing more in the years to come. Protein-conjugate therapeutics can provide several advantages, due to, for example, specificity, multiplicity of functions and relatively low off-target activity, resulting in fewer side effects. Chemical modification of proteins may extend these advantages by rendering them more potent, stable, or multimodal.

A number of standard chemical transformations are commonly used to create and manipulate post-translational modifications on proteins. There are a number of methods where one is able to modify the side chains of certain amino acids selectively. For example, carboxylic acid side chains (aspartate and glutamate) may be targeted by initial activation with a water-soluble carbodiimide reagent and subsequent reaction with an amine. Similarly, lysine can be targeted through the use of activated esters or isothiocyanates, and cysteine thiols can be targeted with maleimides and α-halo-carbonyls.

One significant obstacle to the creation of a chemically altered protein therapeutic or reagent is the production of the protein in a biologically active, homogenous form. Conjugation of a drug or detectable label to a polypeptide can be difficult to control, resulting in a heterogeneous mixture of conjugates that differ in the number of drug molecules attached and in the position of chemical conjugation. In some instances, it may be desirable to control the site of conjugation and/or the drug or detectable label conjugated to the polypeptide using the tools of synthetic organic chemistry to direct the precise and selective formation of chemical bonds on a polypeptide.

SUMMARY

The present disclosure provides conjugate structures and compound structures used to produce these conjugates. The disclosure also encompasses methods of production of such conjugates, as well as methods of using the same.

Embodiments of the present disclosure include a conjugate that includes at least one modified amino acid residue of the formula:

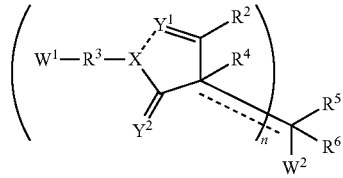

wherein
X is N, NH, O, S, CH or $CH_2$;
$Y^1$ and $Y^2$ are each independently selected from N, O and S;
n is 1 or 2;
$R^2$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
$R^3$ is selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl;
$R^4$ is optional and if present is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester;
$R^5$ is optional and if present is hydrogen or hydroxyl; and
$R^6$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl,
wherein one of $W^1$ and $W^2$ is a polypeptide and the other is a drug or a detectable label,
wherein the dotted lines represent optional bonds,
wherein when the dotted line between the $R^4$-carbon and the $R^5$-carbon is a double bond, n is 1 and $R^4$ and $R^5$ are not present, and
wherein, when n is 2, the dotted line between the $R^4$-carbon and the $R^5$-carbon is not a double bond and $R^5$ is not present.

In some embodiments of the conjugate, $Y^1$ is N.
In some embodiments of the conjugate, $Y^2$ is O.
In some embodiments of the conjugate, $R^2$ is alkyl, substituted alkyl, aryl or substituted aryl.
In some embodiments of the conjugate, $R^2$ is methyl, t-butyl or aryl.
In some embodiments of the conjugate, the dotted line between the $R^4$-carbon and the $R^5$-carbon is a double bond, n is 1, and $R^4$ and $R^5$ are not present.
In some embodiments of the conjugate, the dotted line between the $R^4$-carbon and the $R^5$-carbon is not a double bond, n is 1, and $R^5$ is hydroxyl.
In some embodiments of the conjugate, n is 2, the dotted line between the $R^4$-carbon and the $R^5$-carbon is not a double bond and $R^5$ is not present.
In some embodiments of the conjugate, the dotted line between X and $Y^1$ is a bond, such that the modified amino acid residue has the formula:

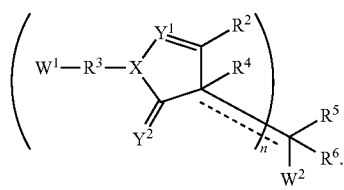

In some embodiments of the conjugate, the dotted line between X and Y is not a bond, such that the modified amino acid residue has the formula:

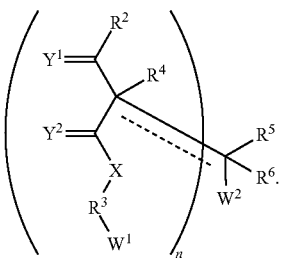

In some embodiments of the conjugate, the detectable label includes a fluorophore.

In some embodiments of the conjugate, $W^1$ is the drug or the detectable label, and $W^2$ is the polypeptide.

In some embodiments of the conjugate, $W^1$ is the polypeptide, and $W^2$ is the drug or the detectable label.

Embodiments of the present disclosure include a compound of the formula:

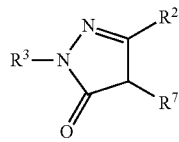

wherein $R^2$ is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^3$ is selected from hydroxyl, alkyl, substituted alkyl, alkenyl, substituted alkenyl, alkynyl, substituted alkynyl, alkoxy, substituted alkoxy, amino, substituted amino, acyl, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, substituted heterocyclyl, and —$R^9W$;

$R^7$ is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester;

$R^9$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl; and W is selected from a drug, a detectable label and a polypeptide.

In some embodiments of the compound, $R^2$ is alkyl, substituted alkyl, aryl or substituted aryl.

In some embodiments of the compound, $R^2$ is methyl, t-butyl or aryl.

In some embodiments of the compound, $R^3$ is substituted aryl.

In some embodiments of the compound, $R^3$ is substituted with one or more groups each independently selected from alkyl, substituted alkyl, alkoxy, substituted alkoxy, amino, substituted amino, carboxyl, carboxyl ester, amide, substituted amide, alkylamide, substituted alkylamide, aryl, substituted aryl, heteroaryl, substituted heteroaryl, cycloalkyl, substituted cycloalkyl, heterocyclyl, and substituted heterocyclyl.

In some embodiments of the compound, $R^3$ is alkylamide or substituted alkylamide.

In some embodiments of the compound, $R^3$ is —$R^9W$.

In some embodiments of the compound, $R^7$ is hydrogen.

In some embodiments of the compound, $R^7$ is halogen.

In some embodiments of the compound, $R^7$ is alkyl or substituted alkyl.

In some embodiments of the compound, the compound is 4-(3-methyl-5-oxo-4,5-dihydro-1H-pyrazol-1-yl)benzoic acid (Compound 10); 3-(2-mercaptoethyl)-1-methyl-1H-pyrazol-5(4H)-one (Compound A4); 3-(2-(2-(3-methyl-5-oxo-4,5-dihydro-1H-pyrazol-1-yl)ethoxy)ethoxy)propanoic acid (Compound 230); perfluorophenyl 3-(2-(2-(3-methyl-5-oxo-4,5-dihydro-1H-pyrazol-1-yl)ethoxy)ethoxy)propanoate (Compound 240); or N-"cargo"-3-(2-(2-(3-methyl-5-oxo-4,5-dihydro-1H-pyrazol-1-yl)ethoxy)ethoxy) propanamide (Compound 250).

Embodiments of the present disclosure include a compound of the formula:

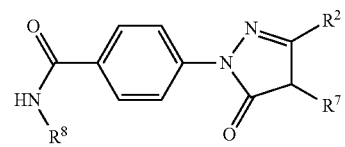

wherein $R^2$ is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^7$ is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester;

$R^8$ is selected from alkyl, substituted alkyl, alkoxy, substituted alkoxy, amino, substituted amino, carboxyl, carboxyl ester, amide, substituted amide, alkylamide, substituted alkylamide, aryl, substituted aryl, heteroaryl, substituted heteroaryl, cycloalkyl, substituted cycloalkyl, heterocyclyl, substituted heterocyclyl, and —$R^9W$;

$R^9$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl; and W is selected from a drug, a detectable label and a polypeptide.

In some embodiments of the compound, $R^2$ is alkyl, substituted alkyl, aryl or substituted aryl.

In some embodiments of the compound, $R^2$ is methyl, t-butyl or aryl.

In some embodiments of the compound, $R^7$ is hydrogen.

In some embodiments of the compound, $R^7$ is halogen.

In some embodiments of the compound, $R^7$ is alkyl or substituted alkyl.

In some embodiments of the compound, $R^8$ is —$R^9W$.

Embodiments of the present disclosure include a conjugate that includes one or more compounds of the formula:

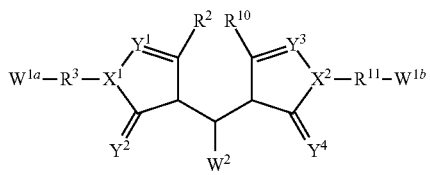

wherein $X^1$ and $X^2$ are each independently selected from N and CH;

$Y^1$ and $Y^3$ are each independently selected from N and S;

$Y^2$ and $Y^4$ are each independently selected from N, O and S;

$R^2$ and $R^{10}$ are each independently selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^3$ and $R^{11}$ are each independently selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl; and $W^{1a}$, $W^{1b}$ and $W^2$ are each independently selected from a drug, a detectable label and a polypeptide.

In some embodiments of the conjugate, $Y^1$ and $Y^3$ are N.

In some embodiments of the conjugate, $R^2$ and $R^{10}$ are each independently selected from alkyl, substituted alkyl, aryl and substituted aryl.

In some embodiments of the conjugate, $R^2$ and $R^{10}$ are each independently selected from methyl, t-butyl and aryl.

In some embodiments of the conjugate, $Y^2$ and $Y^4$ are O.

In some embodiments of the conjugate, $W^{1a}$ and $W^{1b}$ are each independently selected from the drug and the detectable label, and $W^2$ is the polypeptide.

Embodiments of the present disclosure include a method of producing a conjugate. The method includes combining in a reaction mixture a compound of claim 14 and a second compound comprising a reactive group, where the combining is under reaction conditions suitable to promote reaction between the compound and the reactive group of the second compound to form a conjugate. The method also includes isolating the conjugate from the reaction mixture.

In some embodiments of the method, $R^3$ is —$R^9W$, W is the drug or the detectable label, and the second compound is the polypeptide.

In some embodiments of the method, $R^3$ is —$R^9W$, W is the polypeptide, and the second compound is the drug or the detectable label.

In some embodiments of the method, the reactive group includes a reactive aldehyde group or a reactive ketone group.

In some embodiments of the method, the reaction mixture includes water.

In some embodiments of the method, the reaction mixture has a pH of 7.

In some embodiments of the method, the reaction conditions are at a temperature of 37° C.

Embodiments of the present disclosure include a pharmaceutical composition that includes a conjugate as described herein and a pharmaceutically acceptable excipient.

Embodiments of the present disclosure include a method of delivering a conjugate to a subject. The method includes administering to the subject an effective amount of a conjugate as described herein.

Embodiments of the present disclosure include a method of treating a condition in a subject. The method includes administering to the subject having the condition a therapeutically effective amount of a pharmaceutical composition comprising a conjugate as described herein, where the administering is effective to treat the condition in the subject.

Embodiments of the present disclosure include a conjugate that includes a compound of the formula:

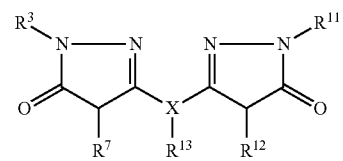

wherein

X is N or CH;

$R^3$ and $R^{11}$ are each independently selected from alkyl, substituted alkyl, alkenyl, substituted alkenyl, alkynyl, substituted alkynyl, alkoxy, substituted alkoxy, amino, substituted amino, acyl, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl, and —$R^9W$;

$R^7$ and $R^{12}$ are each independently selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester;

$R^9$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl;

$R^{13}$ is selected from hydrogen, alkyl, substituted alkyl, alkenyl, substituted alkenyl, alkynyl, substituted alkynyl, alkoxy, substituted alkoxy, amino, substituted amino, acyl, carboxyl, carboxyl ester, acylamino, alkylamide, substituted alkylamide, and —$R^{14}W$;

$R^{14}$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl; and W is selected from a drug, a detectable label and a polypeptide.

In some embodiments of the conjugate, X is N. In some embodiments, X is CH.

In some embodiments of the conjugate, $R^3$ and $R^{11}$ are each independently selected from methyl and phenyl.

In some embodiments of the conjugate, $R^{13}$ is H or substituted alkyl.

BRIEF DESCRIPTION OF THE DRAWINGS

FIG. 4A shows a schematic showing conjugations carried out with either compound C or compound D. FIG. 4B shows the ratio of starting material and product formation was analyzed by liquid chromatography multiple reaction monitoring mass spectrometry (LC-MRM-MS). The disappearance of starting material using compound D is highlighted by the arrow. Compound C did not significantly react with the antibody under the same reaction conditions.

FIGS. 9B and 9C are LC-MS/MS analyses of Product C4 from the conjugation reaction.

FIG. 21 (bottom panel) shows that the major product was double addition on to the heavy chain of the antibody.

DEFINITIONS

Figure 1:
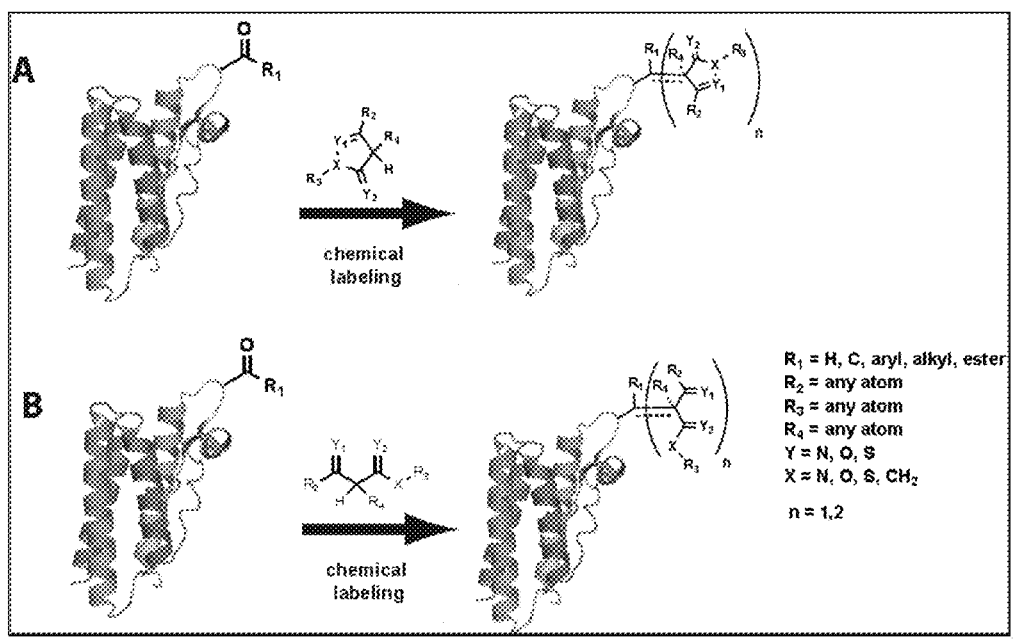
FIG. 1 shows schematic drawings of polypeptide conjugates according to embodiments of the present disclosure. Figure (panel A) shows a reaction scheme for the production of a polypeptide conjugate that includes a cyclic coupling moiety. Figure (panel B) shows a reaction scheme for the production of a polypeptide conjugate that includes an acyclic coupling moiety.

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain (except the $C_1$ carbon) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—C($CH_3)_2CH_2CH_2$—), (—C($CH_3)_2CH_2C(O)$—), (—C($CH_3)_2CH_2C(O)NH$—), (—CH($CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —$SO_2$-alkyl, —$SO_2$-substituted alkyl, —$SO_2$-aryl and —$SO_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—$CH_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO₂H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O— alkynyl, —O—C(O)O-substituted alkynyl, —O—C(O)O-aryl, —O—C(O)O-substituted aryl, —O—C(O)O—cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl and —SO₂-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO₂— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (═O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cycloalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (═S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with ═O, ═NR$^{70}$, ═N—OR$^{70}$, ═N$_2$ or ═S) on saturated carbon atoms in the specified group or radical are, unless otherwise specified, —R$^{60}$, halo, ═O, —OR$^{70}$, —SR$^{70}$, —NR$^{80}$R$^{80}$, trihalomethyl, —CN, —OCN, —SCN, —NO, —NO$_2$, ═N$_2$, —N$_3$, —SO$_2$R$^{70}$, —SO$_2$O$^−$M$^+$, —SO$_2$OR$^{70}$, —OSO$_2$R$^{70}$, —OSO$_2$O$^−$M$^+$, —OSO$_2$OR$^{70}$, —P(O)(O$^−$)$_2$(M$^+$)$_2$, —P(O)(OR$^{70}$)O$^−$M$^+$, —P(O)(OR$^{70}$)$_2$, —C(O)R$^{70}$, —C(S)R$^{70}$, —C(NR$^{70}$)R$^{70}$, —C(O)O$^−$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^−$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^−$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^−$M$^+$, —OR$^{70}$, —SR$^{70}$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$M$^+$, —SO$_3$R$^{70}$, —OSO$_2$R$^{70}$, —OSO$_3$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —OO$_2$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR and —NR where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —OR$^{70}$, —SR$^{70}$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$OR$^{70}$, —P(O)(O)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acids also include naturally occurring amino acids in D-, rather than L-form. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

The term "antibody" is used in the broadest sense and includes monoclonal antibodies (including full length monoclonal antibodies), polyclonal antibodies, and multispecific antibodies (e.g., bispecific antibodies), humanized antibodies, single-chain antibodies, chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in US20040086979 and US20050033031. Accordingly, the antibodies described above may be humanized using methods that are well known in the art.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences that facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest, and the cassette and restriction sites are designed to facilitate insertion of the cassette in the proper reading frame for transcription and translation. Expression cassettes can also comprise elements that facilitate expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

By "reactive partner" is meant a molecule or molecular moiety that specifically reacts with another reactive partner to produce a reaction product. Exemplary reactive partners include a cysteine or serine of sulfatase motif and Formylglycine Generating Enzyme (FGE), which react to form a reaction product of a converted aldehyde tag containing a formylglycine (fGly) in lieu of cysteine or serine in the motif. Other exemplary reactive partners include an aldehyde of an fGly residue of a converted aldehyde tag and an "aldehyde-reactive reactive partner", which comprises an aldehyde-reactive group and a moiety of interest, and which reacts to form a reaction product of a modified aldehyde tagged polypeptide having the moiety of interest conjugated to the modified polypeptide through a modified fGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides conjugates (e.g., polypeptide conjugates), compounds for producing the conjugates and methods of making and using the same. Embodiments of each are described in more detail in the sections below.

Conjugates

The present disclosure provides conjugates. By "conjugate" is meant a first moiety that is stably associated with a second moiety. By "stably associated" is meant that a moiety is bound to another moiety or structure under standard conditions. In certain embodiments, the first and second moieties are bound to each other through one or more covalent bonds.

In certain embodiments, the conjugate is a polypeptide conjugate, which includes a polypeptide conjugated to a second moiety. As described in more detail below, the moiety conjugated to the polypeptide can be any of a variety of moieties such as, but not limited to, a detectable label, a drug, a water-soluble polymer, or a moiety for immobilization of the polypeptide to a membrane or a surface. The moiety of interest can be conjugated to the polypeptide at any desired site of the polypeptide. Thus, the present disclosure provides, for example, a modified polypeptide having a moiety conjugated at a site at or near the C-terminus of the polypeptide. Other examples include a modified polypeptide having a moiety conjugated at a position at or near the N-terminus of the polypeptide. Examples also include a modified polypeptide having a moiety conjugated at a position between the C-terminus and the N-terminus of the polypeptide (e.g., at an internal site of the polypeptide). Combinations of the above are also possible where the modified polypeptide is conjugated to two or more moieties.

Embodiments of the present disclosure include conjugates where a polypeptide is conjugated to one or more moieties, such as 2 moieties, 3 moieties, 4 moieties, 5 moieties, 6 moieties, 7 moieties, 8 moieties, 9 moieties, or 10 or more moieties. The moieties may be conjugated to the polypeptide at one or more sites in the polypeptide. For example, one or more moieties may be conjugated to a single amino acid residue of the polypeptide. In some cases, one moiety is conjugated to an amino acid residue of the polypeptide. In other embodiments, two moieties may be conjugated to the same amino acid residue of the polypeptide. In other embodiments, a first moiety is conjugated to a first amino acid residue of the polypeptide and a second moiety is conjugated to a second amino acid residue of the polypeptide. Combinations of the above are also possible, for example where a polypeptide is conjugated to a first moiety at a first amino acid residue and conjugated to two other moieties at a second amino acid residue. Other combinations are also possible, such as, but not limited to, a polypeptide conjugated to first and second moieties at a first amino acid residue and conjugated to third and fourth moieties at a second amino acid residue, etc.

The one or more amino acid residues that are conjugated to the one or more moieties may be naturally occurring amino acids, unnatural amino acids, or combinations thereof. For instance, the conjugate may include a moiety conjugated to a naturally occurring amino acid residue of the polypeptide. In other instances, the conjugate may include a moiety conjugated to an unnatural amino acid residue of the polypeptide. One or more moieties may be conjugated to the polypeptide at a single natural or unnatural amino acid residue as described above. One or more natural or unnatural amino acid residues in the polypeptide may be conjugated to the moiety or moieties as described herein. For example, two (or more) amino acid residues (e.g., natural or unnatural amino acid residues) in the polypeptide may each be conjugated to one or two moieties, such that multiple sites in the polypeptide are modified.

Although described herein in terms of a polypeptide conjugated to one or more moieties (e.g., a drug, a detectable label, a polypeptide, etc.), embodiments of the present disclosure also include conjugates where a moiety (e.g., a drug or a detectable label) is conjugated to one or more other moieties (e.g., a drug, a detectable label, a polypeptide, etc.). For example, a drug may be conjugated to one or more other moieties (e.g., a drug, a detectable label, a polypeptide, etc.), or in other embodiments, a detectable label may be conjugated to one or more other moieties (e.g., a drug, a detectable label, a polypeptide, etc.). Thus, for instance, embodiments of the present disclosure include, but are not limited to, the following: a conjugate of a polypeptide and a drug; a conjugate of a polypeptide and a detectable label; a conjugate of two or more polypeptides; a conjugate of two or more drugs; a conjugate of two of more detectable labels; a conjugate of a drug and a detectable label; a conjugate of a polypeptide, a drug and a detectable label; a conjugate of a polypeptide and two or more drugs; a conjugate of a polypeptide and two or more detectable labels; a conjugate of a drug and two or more polypeptides; a conjugate of a detectable label and two or more polypeptides; and the like.

In certain embodiments, the polypeptide and the moiety of interest are conjugated through a coupling moiety. For example, the polypeptide and the moiety of interest may each be bound (e.g., covalently bonded) to the coupling moiety, thus indirectly binding the polypeptide and the moiety of interest together. In some cases, the coupling moiety includes a pyrazalinone (Pz) compound or a derivative of a pyrazalinone compound. For instance, a general scheme for coupling a moiety to a polypeptide through a pyrazalinone coupling moiety is shown in the general reaction scheme below.

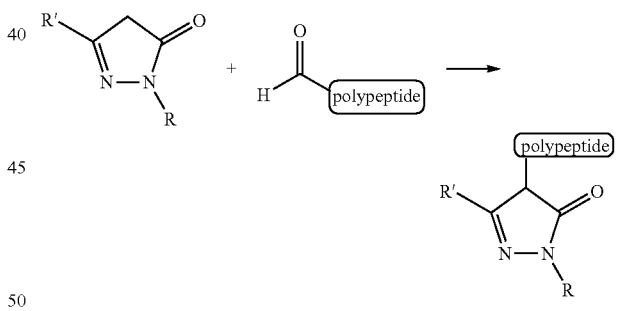

In the reaction scheme above, R may be the moiety of interest conjugated to the polypeptide. As described herein, the moiety can be any of a variety of moieties such as, but not limited to, a detectable label, a drug, a water-soluble polymer, or a moiety for immobilization of the polypeptide to a membrane or a surface of a substrate. R may be any desired substituent, such as, but not limited to, hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. The bond between the polypeptide and the pyrazalinone coupling moiety may be a single bond or a double bond as described in more detail below. Other coupling moieties are also possible, as shown in the conjugates and compounds described in more detail below.

In certain embodiments, the conjugate includes at least one modified amino acid residue of the formula:

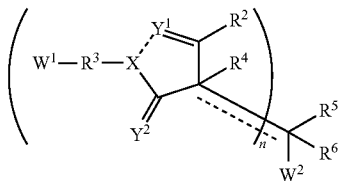

wherein

X is N, NH, O, S, CH or CH$_2$;

Y$^1$ and Y$^2$ are each independently selected from N, O and S;

n is 1 or 2;

R$^2$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

R$^3$ is selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl;

R$^4$ is optional and if present is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester;

R$^5$ is optional and if present is hydrogen or hydroxyl; and

R$^6$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl, wherein one of W$^1$ and W$^2$ is a polypeptide and the other is a drug or a detectable label, wherein the dotted lines represent optional bonds, wherein when the dotted line between the R$^4$-carbon and the R$^5$-carbon is a double bond, n is 1 and R$^4$ and R$^5$ are not present, and wherein, when n is 2, the dotted line between the R$^4$-carbon and the R$^5$-carbon is not a double bond and R$^5$ is not present.

In certain embodiments, X is N, NH, O, S, CH or CH$_2$. In certain embodiments, X is N or NH. In certain embodiments, X is O. In certain embodiments, X is S. In certain embodiments, X is CH or CH$_2$.

In certain embodiments, Y$^1$ and Y$^2$ are each independently selected from N, O and S. In certain embodiments, Y$^1$ is N. In certain embodiments, Y$^1$ is O. In certain embodiments, Y$^1$ is S. In certain embodiments, Y$^2$ is N. In certain embodiments, Y$^2$ is O. In certain embodiments, Y$^2$ is S.

In certain embodiments, Y$^1$ is N and Y$^2$ is O. In certain embodiments, Y$^1$ is N and X is N.

In certain embodiments, n is 1 or 2. In certain embodiments, n is 1. In these embodiments, the polypeptide may be conjugated to a single moiety. For example, in embodiments where W$^2$ is a polypeptide, W$^1$ is the conjugated moiety and n is 1, then the polypeptide is conjugated to one moiety. For instance, as described above, W$^1$ may be a drug or a detectable label, thus the polypeptide may be conjugated to one drug moiety or one detectable label at an amino acid residue of the polypeptide. In certain embodiments, W$^1$ may include a linker moiety through which the drug, detectable label or polypeptide is conjugated to the compound. For example, the linker moiety may include one or more monomer units, such as ethylene oxide of the formula —(CH$_2$—CH$_2$—O)— or —(O—CH$_2$—CH$_2$)—. The number of such units can vary, with the number of such units being from 2 to 10, 2 to 8, 2 to 6, 2 to 4, for example some embodiments include 2 units.

In certain embodiments, n is 2. In some embodiments, the conjugate may include a polypeptide conjugated to two moieties at a single amino acid residue of the polypeptide. For example, in embodiments where W$^2$ is a polypeptide, W$^1$ is the conjugated moiety and n is 2, then the polypeptide is conjugated to two moieties at a single amino acid residue. For instance, as described above, W$^1$ may be a drug or a detectable label, thus the polypeptide may be conjugated to two drug moieties or two detectable labels at a single amino acid residue. In other embodiments, W$^1$ may be the polypeptide and W$^2$ may be the drug or the detectable label. In these embodiments, when n is 2, the drug or detectable label may be conjugated to two polypeptides. In certain embodiments, W$^1$ and/or W$^2$ may include a linker moiety through which the drug, detectable label or polypeptide is conjugated to the compound. For example, the linker moiety may include one or more monomer units, such as ethylene oxide of the formula —(CH$_2$—CH$_2$—O)— or —(O—CH$_2$—CH$_2$)—. The number of such units can vary, with the number of such units being from 2 to 10, 2 to 8, 2 to 6, 2 to 4, for example some embodiments include 2 units.

In certain embodiments, R$^2$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, R$^2$ is hydrogen. In certain embodiments, R$^2$ is alkyl or substituted alkyl. In certain embodiments, R$^2$ is alkenyl or substituted alkenyl. In certain embodiments, R$^2$ is alkynyl or substituted alkynyl. In certain embodiments, R$^2$ is aryl or substituted aryl. In certain embodiments, R$^2$ is heteroaryl or substituted heteroaryl. In certain embodiments, R$^2$ is cycloalkyl or substituted cycloalkyl. In certain embodiments, R$^2$ is heterocyclyl or substituted heterocyclyl.

In certain embodiments, R$^2$ is alkyl, substituted alkyl, aryl or substituted aryl. For example, R$^2$ may be alkyl or substituted alkyl, such as, C$_1$-C$_{10}$ alkyl or C$_1$-C$_{10}$ substituted alkyl (e.g., C$_1$-C$_6$ alkyl or C$_1$-C$_6$ substituted alkyl). In some cases, R$^2$ is methyl, ethyl, n-propyl, iso-propyl, n-butyl, sec-butyl, isobutyl, t-butyl, or the like. In certain cases, R$^2$ is methyl or t-butyl. In certain embodiments, R$^2$ is methyl, t-butyl, aryl or substituted aryl. In certain embodiments, R$^2$ is methyl, t-butyl or aryl.

In certain embodiments, R$^3$ is selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, R$^3$ is alkyl or substituted alkyl. In certain embodiments, R$^3$ is alkenyl or substituted alkenyl. In certain embodiments, R$^3$ is alkynyl or substituted alkynyl. In certain embodiments, R$^3$ is alkoxy or substituted alkoxy. In certain embodiments, $R^3$ is amino or substituted amino. In certain embodiments, $R^3$ is carboxyl or carboxyl ester. In certain embodiments, $R^3$ is acyl amino. In certain embodiments, $R^3$ is alkylamide or substituted alkylamide. In certain embodiments, $R^3$ is aryl or substituted aryl. For example, in some instances, $R^3$ is phenyl or substituted phenyl. In certain embodiments, $R^3$ is heteroaryl or substituted heteroaryl. In certain embodiments, $R^3$ is cycloalkyl or substituted cycloalkyl. In certain embodiments, $R^3$ is heterocyclyl or substituted heterocyclyl.

In certain embodiments, $R^4$ is present. In embodiments where $R^4$ is present, $R^4$ may be selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester. In certain embodiments, $R^4$ is hydrogen. In certain embodiments, $R^4$ is halogen, such as F, Cl, Br or I. In certain embodiments, $R^4$ is F. In certain embodiments, $R^4$ is Cl. In certain embodiments, $R^4$ is Br. In certain embodiments, $R^4$ is I. In certain embodiments, $R^4$ is cyano. In certain embodiments, $R^4$ is alkyl or substituted alkyl. In certain embodiments, $R^4$ is alkenyl or substituted alkenyl. In certain embodiments, $R^4$ is alkynyl or substituted alkynyl. In certain embodiments, $R^4$ is alkylalkoxy or substituted alkylalkoxy. In certain embodiments, $R^4$ is acyl, carboxyl or carboxyl ester.

In certain embodiments, $R^5$ is present. In embodiments where $R^5$ is present, $R^5$ may be hydrogen or hydroxyl. In certain embodiments, $R^5$ is hydrogen. In certain embodiments, $R^5$ is hydroxyl.

In certain embodiments, both $R^4$ and $R^5$ are present. For example, in some embodiments, n is 1 and the dotted line between the $R^4$-carbon and the $R^5$-carbon is absent (i.e., the bond between the $R^4$-carbon and the $R^5$-carbon is a single bond and not a double bond). In these embodiments, both $R^4$ and $R^5$ are present. For instance, $R^5$ may be hydroxyl and $R^4$ may be as described above.

In certain embodiments, $R^4$ is not present. In certain embodiments, $R^5$ is not present. For example, when the dotted line between the $R^4$-carbon and the $R^5$-carbon is a double bond, $R^4$ and $R^5$ are not present. In these embodiments, n is 1. In other embodiments, one of $R^4$ or $R^5$ may be absent. For instance, in some embodiments, n is 2 and the dotted line between the $R^4$-carbon and the $R^5$-carbon may be absent (i.e., the bond between the $R^4$-carbon and the $R^5$-carbon is a single bond and not a double bond). In these embodiments, $R^5$ is not present and $R^4$ is present.

In certain embodiments, $R^6$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, $R^6$ is hydrogen. In certain embodiments, $R^6$ is alkyl or substituted alkyl. In certain embodiments, $R^6$ is alkenyl or substituted alkenyl. In certain embodiments, $R^6$ is alkynyl or substituted alkynyl. In certain embodiments, $R^6$ is alkoxy or substituted alkoxy. In certain embodiments, $R^6$ is amino or substituted amino. In certain embodiments, $R^6$ is carboxyl or carboxyl ester. In certain embodiments, $R^6$ is acyl amino. In certain embodiments, $R^6$ is alkylamide or substituted alkylamide. In certain embodiments, $R^6$ is aryl or substituted aryl. In certain embodiments, $R^6$ is heteroaryl or substituted heteroaryl. In certain embodiments, $R^6$ is cycloalkyl or substituted cycloalkyl. In certain embodiments, $R^6$ is heterocyclyl or substituted heterocyclyl.

In certain embodiments, one of $W^1$ and $W^2$ is a polypeptide and the other is a drug or a detectable label. In certain embodiments, $W^1$ is the drug or the detectable label, and $W^2$ is the polypeptide. In certain embodiments, $W^1$ is the polypeptide, and $W^2$ is the drug or the detectable label.

In certain embodiments, the dotted line between X and $Y^1$ is a bond, such that the modified amino acid residue has the formula:

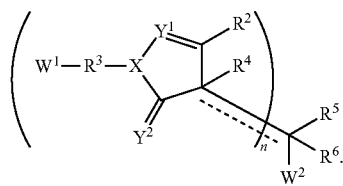

In these embodiments, the elements $R^2$, $R^3$, $R^4$, $R^5$, $R^6$, $W^1$, $W^2$, X, $Y^1$, $Y^2$ and n are as described above.

In certain embodiments, the dotted line between X and $Y^1$ is not a bond, such that the modified amino acid residue has the formula:

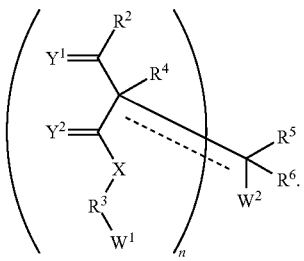

In these embodiments, the elements $R^2$, $R^3$, $R^4$, $R^5$, $R^6$, $W^1$, $W^2$, X, $Y^1$, $Y^2$ and n are as described above.

As described above, in certain embodiments of the conjugate, n is 2. In these embodiments, the conjugate may include conjugation between three moieties. For example, embodiments of the conjugate may include a conjugate having one or more compounds of the formula:

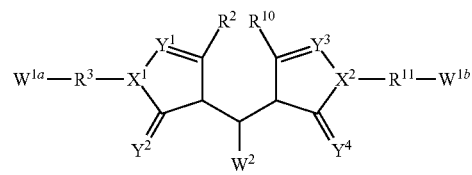

wherein
$X^1$ and $X^2$ are each independently selected from N and CH;
$Y^1$ and $Y^3$ are each independently selected from N and S;
$Y^2$ and $Y^4$ are each independently selected from N, O and S;
$R^2$ and $R^{10}$ are each independently selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl; and
$R^3$ and $R^{11}$ are each independently selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl, $W^{1a}$, $W^{1b}$ and $W^2$ are each independently selected from a drug, a detectable label and a polypeptide.

In certain embodiments, $X^1$ and $X^2$ are each independently selected from N and CH. In certain embodiments, $X^1$ is N. In certain embodiments, $X^1$ is CH. In certain embodiments, $X^2$ is N. In certain embodiments, $X^2$ is CH. In certain embodiments, $X^1$ and $X^2$ are N. In certain embodiments, $X^1$ and $X^2$ are CH. In certain embodiments, $X^1$ is N and $X^2$ is CH. In certain embodiments, $X^1$ is CH and $X^2$ is N.

In certain embodiments, $Y^1$ and $Y^3$ are each independently selected from N and S. In certain embodiments, $Y^1$ is N. In certain embodiments, $Y^1$ is S. In certain embodiments, $Y^3$ is N. In certain embodiments, $Y^3$ is S. In certain embodiments, $Y^1$ and $Y^3$ are N. In certain embodiments, $Y^1$ and $Y^3$ are S. In certain embodiments, $Y^1$ is N and $Y^3$ is S. In certain embodiments, $Y^1$ is S and $Y^3$ is N.

In certain embodiments, $Y^2$ and $Y^4$ are each independently selected from N, O and S. In certain embodiments, $Y^2$ is N. In certain embodiments, $Y^2$ is O. In certain embodiments, $Y^2$ is S. In certain embodiments, $Y^4$ is N. In certain embodiments, $Y^4$ is O. In certain embodiments, $Y^4$ is S. In certain embodiments, $Y^2$ and $Y^4$ are O.

In certain embodiments, $R^2$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^2$ is hydrogen. In certain embodiments, $R^2$ is alkyl or substituted alkyl. In certain embodiments, $R^2$ is alkenyl or substituted alkenyl. In certain embodiments, $R^2$ is alkynyl or substituted alkynyl. In certain embodiments, $R^2$ is aryl or substituted aryl. In certain embodiments, $R^2$ is heteroaryl or substituted heteroaryl. In certain embodiments, $R^2$ is cycloalkyl or substituted cycloalkyl. In certain embodiments, $R^2$ is heterocyclyl or substituted heterocyclyl.

In certain embodiments, $R^2$ is alkyl, substituted alkyl, aryl or substituted aryl. For example, $R^2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R^2$ is methyl, ethyl, n-propyl, iso-propyl, n-butyl, sec-butyl, isobutyl, t-butyl, or the like. In certain cases, $R^2$ is methyl or t-butyl. In certain embodiments, $R^2$ is methyl, t-butyl, aryl or substituted aryl. In certain embodiments, $R^2$ is methyl, t-butyl or aryl.

In certain embodiments, $R^{10}$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^{10}$ is hydrogen. In certain embodiments, $R^{10}$ is alkyl or substituted alkyl. In certain embodiments, $R^{10}$ is alkenyl or substituted alkenyl. In certain embodiments, $R^{10}$ is alkynyl or substituted alkynyl. In certain embodiments, $R^{10}$ is aryl or substituted aryl. In certain embodiments, $R^{10}$ is heteroaryl or substituted heteroaryl. In certain embodiments, $R^{10}$ is cycloalkyl or substituted cycloalkyl. In certain embodiments, $R^{10}$ is heterocyclyl or substituted heterocyclyl.

In certain embodiments, $R^{10}$ is alkyl, substituted alkyl, aryl or substituted aryl. For example, $R^{10}$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R^{10}$ is methyl, ethyl, n-propyl, iso-propyl, n-butyl, sec-butyl, isobutyl, t-butyl, or the like. In certain cases, $R^{10}$ is methyl or t-butyl. In certain embodiments, $R^{10}$ is methyl, t-butyl, aryl or substituted aryl. In certain embodiments, $R^{10}$ is methyl, t-butyl or aryl.

In certain embodiments, $R^3$ is selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, $R^3$ is alkyl or substituted alkyl. In certain embodiments, $R^3$ is alkenyl or substituted alkenyl. In certain embodiments, $R^3$ is alkynyl or substituted alkynyl. In certain embodiments, $R^3$ is alkoxy or substituted alkoxy. In certain embodiments, $R^3$ is amino or substituted amino. In certain embodiments, $R^3$ is carboxyl or carboxyl ester. In certain embodiments, $R^3$ is acyl amino. In certain embodiments, $R^3$ is alkylamide or substituted alkylamide. In certain embodiments, $R^3$ is aryl or substituted aryl. For example, in some instances, $R^3$ is phenyl or substituted phenyl. In certain embodiments, $R^3$ is heteroaryl or substituted heteroaryl. In certain embodiments, $R^3$ is cycloalkyl or substituted cycloalkyl. In certain embodiments, $R^3$ is heterocyclyl or substituted heterocyclyl.

In certain embodiments, $R^{11}$ is selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, $R^{11}$ is alkyl or substituted alkyl. In certain embodiments, $R^{11}$ is alkenyl or substituted alkenyl. In certain embodiments, $R^{11}$ is alkynyl or substituted alkynyl. In certain embodiments, $R^{11}$ is alkoxy or substituted alkoxy. In certain embodiments, $R^{11}$ is amino or substituted amino. In certain embodiments, $R^{11}$ is carboxyl or carboxyl ester. In certain embodiments, $R^{11}$ is acyl amino. In certain embodiments, $R^{11}$ is alkylamide or substituted alkylamide. In certain embodiments, $R^{11}$ is aryl or substituted aryl. For example, in some instances, $R^{11}$ is phenyl or substituted phenyl. In certain embodiments, $R^{11}$ is heteroaryl or substituted heteroaryl. In certain embodiments, $R^{11}$ is cycloalkyl or substituted cycloalkyl. In certain embodiments, $R^{11}$ is heterocyclyl or substituted heterocyclyl.

In certain embodiments, $W^{1a}$, $W^{1b}$ and $W^2$ are each independently selected from a drug, a detectable label and a polypeptide. In certain embodiments, $W^{1a}$ is a drug or a detectable label. In certain embodiments, $W^{1a}$ is a polypeptide. In certain embodiments, $W^{1b}$ is a drug or a detectable label. In certain embodiments, $W^{1b}$ is a polypeptide. In certain embodiments, $W^2$ is a drug or a detectable label. In certain embodiments, $W^2$ is a polypeptide. For example, $W^2$ may be a polypeptide and $W^{1a}$ and $W^{1b}$ may each be a drug or a detectable label. In these embodiments, two moieties may be conjugated to a single amino acid residue of the polypeptide. For instance, $W^2$ may be a polypeptide and $W^{1a}$ and $W^{1b}$ may each be a drug. In other instances, $W^2$ may be a polypeptide and $W^{1a}$ and $W^{1b}$ may each be a detectable label. In other instances, $W^2$ may be a polypeptide and one of $W^{1a}$ and $W^{1b}$ is a drug and the other is a detectable label.

Other combinations of conjugated moieties are possible. For example, in some cases, $W^{1a}$ may be a polypeptide, $W^{1b}$ may be a drug or a detectable label and $W^2$ may be a drug or a detectable label. In other cases, $W^{1a}$ may be a drug or a detectable label, $W^{1b}$ may be a polypeptide and $W^2$ may be a drug or a detectable label. In other cases, $W^{1a}$ may be a polypeptide, $W^{1b}$ may be a polypeptide and $W^2$ may be a drug or a detectable label. In other cases, $W^{1a}$ may be a polypeptide, $W^{1b}$ may be a drug or a detectable label and $W^2$ may be a polypeptide. In other cases, $W^{1a}$ may be a drug or a detectable label, $W^{1b}$ may be a polypeptide and $W^2$ may be a polypeptide. In other cases, $W^{1a}$, $W^{1b}$ and $W^2$ are each polypeptides. In other cases, $W^{1a}$, $W^{1b}$ and $W^2$ are each independently selected from a drug and a detectable label.

In certain embodiments, one or more of $W^{1a}$, $W^{1b}$ and $W^2$ may include a linker moiety through which the drug, detectable label or polypeptide is conjugated to the compound. For example, the linker moiety may include one or more monomer units, such as ethylene oxide of the formula —($CH_2$—$CH_2$—O)— or —(O—$CH_2$—$CH_2$)—. The number of such units can vary, with the number of such units being from 2 to 10, 2 to 8, 2 to 6, 2 to 4, for example some embodiments include 2 units.

Compounds Useful for Producing Conjugates

The present disclosure provides compounds useful for producing the conjugates described herein. In certain embodiments, the compound may be a coupling moiety useful for conjugation of a polypeptide and a second moiety. For example, the compound may be bound to the polypeptide and also bound to the second moiety, thus indirectly binding the polypeptide and the second moiety together.

In certain instances, the compound may be a pyrazalinone or a pyrazalinone derivative. Embodiments of the compound include a compound of the formula:

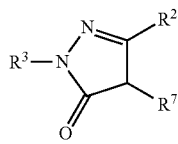

wherein $R^2$ is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^3$ is selected from hydroxyl, alkyl, substituted alkyl, alkenyl, substituted alkenyl, alkynyl, substituted alkynyl, alkoxy, substituted alkoxy, amino, substituted amino, acyl, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, substituted heterocyclyl, and —$R^9W$;

$R^7$ is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester;

$R^9$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl; and W is selected from a drug, a detectable label and a polypeptide.

In certain embodiments, $R^2$ is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^2$ is alkyl or substituted alkyl. In certain embodiments, $R^2$ is alkenyl or substituted alkenyl. In certain embodiments, $R^2$ is alkynyl or substituted alkynyl. In certain embodiments, $R^2$ is aryl or substituted aryl. In certain embodiments, $R^2$ is heteroaryl or substituted heteroaryl. In certain embodiments, $R^2$ is cycloalkyl or substituted cycloalkyl. In certain embodiments, $R^2$ is heterocyclyl or substituted heterocyclyl.

In certain embodiments, $R^2$ is alkyl, substituted alkyl, aryl or substituted aryl. For example, $R^2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R^2$ is methyl, ethyl, n-propyl, iso-propyl, n-butyl, sec-butyl, isobutyl, t-butyl, or the like. In certain cases, $R^2$ is methyl or t-butyl. In certain embodiments, $R^2$ is methyl, t-butyl, aryl or substituted aryl. In certain embodiments, $R^2$ is methyl, t-butyl or aryl. In certain embodiments, $R^2$ is n-propyl or substituted n-propyl. For example, $R^2$ may be n-propyl or n-propyl substituted with one or more groups, such as, but not limited to hydroxyl, amino, halo, cyano, and the like. In some instances, $R^2$ may be n-propyl substituted with a cyano group. In some instances, $R^2$ may be n-propyl substituted with two cyano groups.

In certain embodiments, $R^3$ is selected from hydroxyl, alkyl, substituted alkyl, alkenyl, substituted alkenyl, alkynyl, substituted alkynyl, alkoxy, substituted alkoxy, amino, substituted amino, acyl, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, substituted heterocyclyl, and —$R^9W$. In certain embodiments, $R^3$ is hydroxyl. In certain embodiments, $R^3$ is alkyl or substituted alkyl. In certain embodiments, $R^3$ is alkenyl or substituted alkenyl. In certain embodiments, $R^3$ is alkynyl or substituted alkynyl. In certain embodiments, $R^3$ is alkoxy or substituted alkoxy. In certain embodiments, $R^3$ is amino or substituted amino. In certain embodiments, $R^3$ is acyl, carboxyl or carboxyl ester. In certain embodiments, $R^3$ is acyl amino. In certain embodiments, $R^3$ is alkylamide or substituted alkylamide. In certain embodiments, $R^3$ is aryl or substituted aryl. For example, in some instances, $R^3$ is phenyl or substituted phenyl. In certain embodiments, $R^3$ is heteroaryl or substituted heteroaryl. In certain embodiments, $R^3$ is cycloalkyl or substituted cycloalkyl. In certain embodiments, $R^3$ is heterocyclyl or substituted heterocyclyl.

In certain embodiments, $R^3$ is —$R^9W$. In certain embodiments, W is selected from a drug, a detectable label and a polypeptide. In certain embodiments, W is a drug. In certain embodiments, W is a detectable label. In certain embodiments, W is a polypeptide. In certain embodiments, W may include a linker moiety through which the drug, detectable label or polypeptide is conjugated to the compound. For example, the linker moiety may include one or more monomer units, such as ethylene oxide of the formula —($CH_2$—$CH_2$—O)— or —(O—$CH_2$—$CH_2$)—. The number of such units can vary, with the number of such units being from 2 to 10, 2 to 8, 2 to 6, 2 to 4, for example some embodiments include 2 units. $R^9$ is described in more detail below.

In certain embodiments, $R^3$ is substituted with one or more groups to facilitate coupling of the compound to a second moiety. For instance, $R^3$ may be substituted with one or more reactive groups. In some cases, the reactive group(s) may be configured to react with a corresponding reactive partner on the second moiety (e.g., a drug, a detectable label, or a polypeptide) to facilitate coupling of the compound to the second moiety. For example, in certain embodiments, $R^3$ is substituted with one or more groups each independently selected from alkyl, substituted alkyl, alkoxy, substituted alkoxy, amino, substituted amino, carboxyl, carboxyl ester, aminoacyl, amide, substituted amide, alkylamide, substituted alkylamide, aryl, substituted aryl, heteroaryl, substituted heteroaryl, cycloalkyl, substituted cycloalkyl, heterocyclyl, and substituted heterocyclyl.

In certain embodiments, $R^7$ is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester. In certain embodiments, $R^7$ is hydrogen. In certain embodiments, $R^7$ is halogen (e.g., F, Cl, Br or I). In certain embodiments, $R^7$ is F. In certain embodiments, $R^7$ is Cl. In certain embodiments, $R^7$ is Br. In certain embodiments, $R^7$ is I. In certain embodiments, $R^7$ is cyano. In certain embodiments, $R^7$ is alkyl or substituted alkyl. In certain embodiments, $R^7$ is alkenyl or substituted alkenyl. In certain embodiments, $R^7$ is alkynyl or substituted alkynyl. In certain embodiments, $R^7$ is alkylalkoxy or substituted alkylalkoxy. In certain embodiments, $R^7$ is acyl, carboxyl or carboxyl ester.

In certain embodiments, $R^9$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, $R^9$ is alkyl or substituted alkyl. In certain embodiments, $R^9$ is alkenyl or substituted alkenyl. In certain embodiments, $R^9$ is alkynyl or substituted alkynyl. In certain embodiments, $R^9$ is alkoxy or substituted alkoxy. In certain embodiments, $R^9$ is amino or substituted amino. In certain embodiments, $R^9$ is carboxyl or carboxyl ester. In certain embodiments, $R^9$ is acylamino. In certain embodiments, $R^9$ is alkylamide or substituted alkylamide. In certain embodiments, $R^9$ is aryl or substituted aryl. In certain embodiments, $R^9$ is heteroaryl or substituted heteroaryl. In certain embodiments, $R^9$ is cycloalkyl or substituted cycloalkyl. In certain embodiments, $R^9$ is heterocyclyl or substituted heterocyclyl.

In some instances, $R^2$ may be a substituted alkyl, such as a substituted $C_{1-6}$ alkyl, or a substituted $C_{1-3}$ alkyl. In some instances, $R^2$ is a substituted ethyl group. The substituted alkyl group may be substituted by any of the substituents defined herein. For instance, the substituted alkyl group may be substituted by a thiol group or an acylamino group.

In some instances, the compound may be a compound of the formula described above, where $R^2$ is a substituted ethyl group that is substituted by a thiol group, $R^3$ is an alkyl group (such as a $C_{1-6}$ alkyl, or a $C_{1-3}$ alkyl), and $R^7$ is hydrogen. In these embodiments, the compound may be 3-(2-mercaptoethyl)-1-methyl-1H-pyrazol-5(4H)-one (Compound A4).

In some instances, $R^3$ may be a substituted alkyl, such as a substituted $C_{1-6}$ alkyl, or a substituted $C_{1-3}$ alkyl. In some instances, $R^3$ is a substituted methyl or a substituted ethyl group. The substituted alkyl group may be substituted by any of the substituents defined herein. For example, $R^3$ may be a substituted methyl group. In some instances, the methyl group is substituted with a carboxyl or aminoacyl. In some instances, the methyl group is substituted with an aminoacyl group. In addition, as described herein compounds of the present disclosure may be conjugated to a drug, a detectable label or a polypeptide. For example, as described in the formula above, $R^3$ may be —$R^9W$, where W is a drug, a detectable label or a polypeptide (e.g., a "cargo"). In some instances, the "cargo" may be conjugated to the compounds described herein through an amide bond. For example, the "cargo" may be conjugated to the compound through an amide bond to give a compound of the following formula:

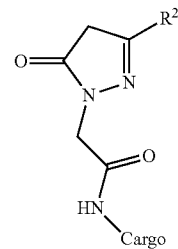

In some instances, when $R^3$ is a substituted alkyl group, the substituted alkyl group may be substituted by a linker moiety. The linker moiety may include one or more monomer units, such as ethylene oxide of the formula —($CH_2$—$CH_2$—O)— or —(O—$CH_2$—$CH_2$)—. The number of such units can vary, with the number of such units being from 2 to 10, 2 to 8, 2 to 6, 2 to 4, for example some embodiments include 2 units. Furthermore, the last ethylene oxide group in the linker group may be further substituted by one or more functional groups as defined herein, such as, for example, alkyl, substituted alkyl, alkenyl, substituted alkenyl, alkynyl, substituted alkynyl, hydroxyl, alkoxy, substituted alkoxy, amino, substituted amino, acyl, carboxyl, carboxyl ester, acylamino, aminoacyl, alkylamide, substituted alkylamide, aryl, substituted aryl, heteroaryl, substituted heteroaryl, cycloalkyl, substituted cycloalkyl, heterocyclyl, or substituted heterocyclyl. In some instances, the last ethylene oxide group in the linker group may be further substituted by a carboxyl, or a protected carboxyl group, such as a perfluorophenyl protected carboxyl group.

For example, specific compounds of the above formula include, but are not limited to, 3-(2-(2-(3-methyl-5-oxo-4, 5-dihydro-1H-pyrazol-1-yl)ethoxy)ethoxy)propanoic acid (Compound 230) and perfluorophenyl 3-(2-(2-(3-methyl-5-oxo-4,5-dihydro-1H-pyrazol-1-yl)ethoxy)ethoxy)propanoate (Compound 240).

In addition, as described herein compounds of the present disclosure may be conjugated to a drug, a detectable label or a polypeptide. For example, as described in the formula above, $R^3$ may be —$R^9W$, where W is a drug, a detectable label or a polypeptide (e.g., a "cargo"). In some instances, the "cargo" may be conjugated to the compounds described herein through an amide bond. For example, the "cargo" may be conjugated to Compound 240 described herein through the formation of an amide bond, resulting in N-"Cargo"-3-(2-(2-(3-methyl-5-oxo-4,5-dihydro-1H-pyrazol-1-yl)ethoxy)ethoxy) propanamide (Compound 250).

In certain embodiments, the compound may be a pyrazalinone derivative. Embodiments of the compound include a compound of the formula:

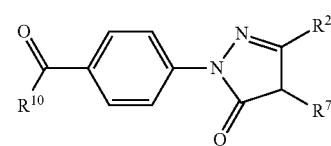

wherein

R² is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

R⁷ is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester;

R¹⁰ is selected from alkyl, substituted alkyl, hydroxyl, alkoxy, substituted alkoxy, amino, substituted amino, carboxyl, carboxyl ester, amide, substituted amide, alkylamide, substituted alkylamide, aryl, substituted aryl, heteroaryl, substituted heteroaryl, cycloalkyl, substituted cycloalkyl, heterocyclyl, substituted heterocyclyl, and —R⁹W;

R⁹ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl; and W is selected from a drug, a detectable label and a polypeptide.

In certain embodiments, R² is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, R² is alkyl or substituted alkyl. In certain embodiments, R² is alkenyl or substituted alkenyl. In certain embodiments, R² is alkynyl or substituted alkynyl. In certain embodiments, R² is aryl or substituted aryl. In certain embodiments, R² is heteroaryl or substituted heteroaryl. In certain embodiments, R² is cycloalkyl or substituted cycloalkyl. In certain embodiments, R² is heterocyclyl or substituted heterocyclyl.

In certain embodiments, R² is alkyl, substituted alkyl, aryl or substituted aryl. For example, R² may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, R² is methyl, ethyl, n-propyl, iso-propyl, n-butyl, sec-butyl, isobutyl, t-butyl, or the like. In certain cases, R² is methyl or t-butyl. In certain embodiments, R² is methyl, t-butyl, aryl or substituted aryl. In certain embodiments, R² is methyl, t-butyl or aryl.

In certain embodiments, R⁷ is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester. In certain embodiments, R⁷ is hydrogen. In certain embodiments, R⁷ is halogen (e.g., F, Cl, Br or I). In certain embodiments, R⁷ is F. In certain embodiments, R⁷ is Cl. In certain embodiments, R⁷ is Br. In certain embodiments, R⁷ is I. In certain embodiments, R⁷ is cyano. In certain embodiments, R⁷ is alkyl or substituted alkyl. In certain embodiments, R⁷ is alkenyl or substituted alkenyl. In certain embodiments, R⁷ is alkynyl or substituted alkynyl. In certain embodiments, R⁷ is alkylalkoxy or substituted alkylalkoxy. In certain embodiments, R⁷ is acyl, carboxyl or carboxyl ester.

In certain embodiments, R¹⁰ is selected from alkyl, substituted alkyl, hydroxyl, alkoxy, substituted alkoxy, amino, substituted amino, carboxyl, carboxyl ester, amide, substituted amide, alkylamide, substituted alkylamide, aryl, heteroaryl, substituted heteroaryl, cycloalkyl, substituted cycloalkyl, substituted heterocyclyl, and —R⁹W. In certain embodiments, R¹⁰ is alkyl or substituted alkyl. In certain embodiments, R¹⁰ is hydroxyl. In certain embodiments, R¹⁰ is alkoxy or substituted alkoxy. In certain embodiments, R¹⁰ is amino or substituted amino. In certain embodiments, R¹⁰ is carboxyl or carboxyl ester. In certain embodiments, R¹⁰ is amide or substituted amide. In certain embodiments, R¹⁰ is alkylamide or substituted alkylamide. In certain embodiments, R¹⁰ is aryl or substituted aryl. In certain embodiments, R¹⁰ is heteroaryl or substituted heteroaryl. In certain embodiments, R¹⁰ is cycloalkyl or substituted cycloalkyl. In certain embodiments, R¹⁰ is heterocyclyl or substituted heterocyclyl.

In certain embodiments, R¹⁰ is —R⁹W. In certain embodiments, W is selected from a drug, a detectable label and a polypeptide. In certain embodiments, W is a drug. In certain embodiments, W is a detectable label. In certain embodiments, W is a polypeptide. In certain embodiments, W may include a linker moiety through which the drug, detectable label or polypeptide is conjugated to the compound. For example, the linker moiety may include one or more monomer units, such as ethylene oxide of the formula —($CH_2$—$CH_2$—O)— or —(O—$CH_2$—$CH_2$)—. The number of such units can vary, with the number of such units being from 2 to 10, 2 to 8, 2 to 6, 2 to 4, for example some embodiments include 2 units. R⁹ is described in more detail below.

In certain embodiments, R⁹ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, R⁹ is alkyl or substituted alkyl. In certain embodiments, R⁹ is alkenyl or substituted alkenyl. In certain embodiments, R⁹ is alkynyl or substituted alkynyl. In certain embodiments, R⁹ is alkoxy or substituted alkoxy. In certain embodiments, R⁹ is amino or substituted amino. In certain embodiments, R⁹ is carboxyl or carboxyl ester. In certain embodiments, R⁹ is acylamino. In certain embodiments, R⁹ is alkylamide or substituted alkylamide. In certain embodiments, R⁹ is aryl or substituted aryl. In certain embodiments, R⁹ is heteroaryl or substituted heteroaryl. In certain embodiments, R⁹ is cycloalkyl or substituted cycloalkyl. In certain embodiments, R⁹ is heterocyclyl or substituted heterocyclyl.

An example of a compound of the above formula includes a compound where R² is methyl, R⁷ is hydrogen, and R¹⁰ is hydroxyl. For instance, the compound may be 4-(3-methyl-5-oxo-4,5-dihydro-1H-pyrazol-1-yl)benzoic acid (Compound 10).

Another example of a compound of the above formula includes a compound where R¹⁰ is amino or substituted amino. In these embodiments, the compound may be a pyrazalinone derivative, such as a compound of the formula:

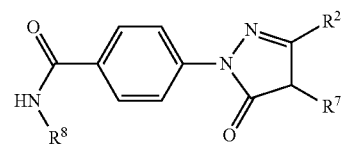

wherein

R² is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^7$ is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester;

$R^8$ is selected from alkyl, substituted alkyl, alkoxy, substituted alkoxy, amino, substituted amino, carboxyl, carboxyl ester, amide, substituted amide, alkylamide, substituted alkylamide, aryl, substituted aryl, heteroaryl, substituted heteroaryl, cycloalkyl, substituted cycloalkyl, heterocyclyl, substituted heterocyclyl, and —$R^9W$;

$R^9$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl; and W is selected from a drug, a detectable label and a polypeptide.

In certain embodiments, $R^2$ is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^2$ is alkyl or substituted alkyl. In certain embodiments, $R^2$ is alkenyl or substituted alkenyl. In certain embodiments, $R^2$ is alkynyl or substituted alkynyl. In certain embodiments, $R^2$ is aryl or substituted aryl. In certain embodiments, $R^2$ is heteroaryl or substituted heteroaryl. In certain embodiments, $R^2$ is cycloalkyl or substituted cycloalkyl. In certain embodiments, $R^2$ is heterocyclyl or substituted heterocyclyl.

In certain embodiments, $R^2$ is alkyl, substituted alkyl, aryl or substituted aryl. For example, $R^2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R^2$ is methyl, ethyl, n-propyl, iso-propyl, n-butyl, sec-butyl, isobutyl, t-butyl, or the like. In certain cases, $R^2$ is methyl or t-butyl. In certain embodiments, $R^2$ is methyl, t-butyl, aryl or substituted aryl. In certain embodiments, $R^2$ is methyl, t-butyl or aryl.

In certain embodiments, $R^7$ is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester. In certain embodiments, $R^7$ is hydrogen. In certain embodiments, $R^7$ is halogen (e.g., F, Cl, Br or I). In certain embodiments, $R^7$ is F. In certain embodiments, $R^7$ is Cl. In certain embodiments, $R^7$ is Br. In certain embodiments, $R^7$ is I. In certain embodiments, $R^7$ is cyano. In certain embodiments, $R^7$ is alkyl or substituted alkyl. In certain embodiments, $R^7$ is alkenyl or substituted alkenyl. In certain embodiments, $R^7$ is alkynyl or substituted alkynyl. In certain embodiments, $R^7$ is alkylalkoxy or substituted alkylalkoxy. In certain embodiments, $R^7$ is acyl, carboxyl or carboxyl ester.

In certain embodiments, $R^8$ is selected from alkyl, substituted alkyl, alkoxy, substituted alkoxy, amino, substituted amino, carboxyl, carboxyl ester, amide, substituted amide, alkylamide, substituted alkylamide, aryl, substituted aryl, heteroaryl, substituted heteroaryl, cycloalkyl, substituted cycloalkyl, heterocyclyl, substituted heterocyclyl, and —$R^9W$. In certain embodiments, $R^8$ is alkyl or substituted alkyl. In certain embodiments, $R^8$ is alkoxy or substituted alkoxy. In certain embodiments, $R^8$ is amino or substituted amino. In certain embodiments, $R^8$ is carboxyl or carboxyl ester. In certain embodiments, $R^8$ is amide or substituted amide. In certain embodiments, $R^8$ is alkylamide or substituted alkylamide. In certain embodiments, $R^8$ is aryl or substituted aryl. In certain embodiments, $R^8$ is heteroaryl or substituted heteroaryl. In certain embodiments, $R^8$ is cycloalkyl or substituted cycloalkyl. In certain embodiments, $R^8$ is heterocyclyl or substituted heterocyclyl.

In certain embodiments, $R^8$ is —$R^9W$. In certain embodiments, W is selected from a drug, a detectable label and a polypeptide. In certain embodiments, W is a drug. In certain embodiments, W is a detectable label. In certain embodiments, W is a polypeptide. In certain embodiments, W may include a linker moiety through which the drug, detectable label or polypeptide is conjugated to the compound. For example, the linker moiety may include one or more monomer units, such as ethylene oxide of the formula —($CH_2$—$CH_2$—O)— or —(O—$CH_2$—$CH_2$)—. The number of such units can vary, with the number of such units being from 2 to 10, 2 to 8, 2 to 6, 2 to 4, for example some embodiments include 2 units. $R^9$ is described in more detail below.

In certain embodiments, $R^9$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, $R^9$ is alkyl or substituted alkyl. In certain embodiments, $R^9$ is alkenyl or substituted alkenyl. In certain embodiments, $R^9$ is alkynyl or substituted alkynyl. In certain embodiments, $R^9$ is alkoxy or substituted alkoxy. In certain embodiments, $R^9$ is amino or substituted amino. In certain embodiments, $R^9$ is carboxyl or carboxyl ester. In certain embodiments, $R^9$ is acylamino. In certain embodiments, $R^9$ is alkylamide or substituted alkylamide. In certain embodiments, $R^9$ is aryl or substituted aryl. In certain embodiments, $R^9$ is heteroaryl or substituted heteroaryl. In certain embodiments, $R^9$ is cycloalkyl or substituted cycloalkyl. In certain embodiments, $R^9$ is heterocyclyl or substituted heterocyclyl.

Additional Compounds

In certain instances, the compound may be a bis-pyrazalinone or a bis-pyrazalinone derivative. Embodiments of the compound include a compound of the formula:

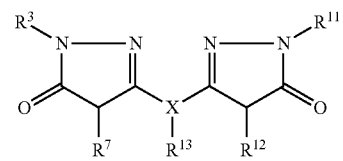

wherein

X is N or CH;

$R^3$ and $R^{11}$ are each independently selected from alkyl, substituted alkyl, alkenyl, substituted alkenyl, alkynyl, substituted alkynyl, alkoxy, substituted alkoxy, amino, substituted amino, acyl, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl, and —$R^9W$;

$R^7$ and $R^{12}$ are each independently selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester;

$R^9$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl;

$R^{13}$ is selected from hydrogen, alkyl, substituted alkyl, alkenyl, substituted alkenyl, alkynyl, substituted alkynyl, alkoxy, substituted alkoxy, amino, substituted amino, acyl, carboxyl, carboxyl ester, acylamino, alkylamide, substituted alkylamide, and —$R^{14}W$;

$R^{14}$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl; and W is selected from a drug, a detectable label and a polypeptide.

In certain embodiments, X is N or CH. In certain embodiments, X is N. In certain embodiments, X is CH.

In certain embodiments, $R^3$ is selected from alkyl, substituted alkyl, alkenyl, substituted alkenyl, alkynyl, substituted alkynyl, alkoxy, substituted alkoxy, amino, substituted amino, acyl, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl, and —$R^9W$. In certain embodiments, $R^3$ is alkyl or substituted alkyl. For instance, $R^3$ may be alkyl, such as $C_{1-6}$ alkyl, including $C_{1-3}$ alkyl. In some instances, $R^3$ is methyl. In certain embodiments, $R^3$ is alkenyl or substituted alkenyl. In certain embodiments, $R^3$ is alkynyl or substituted alkynyl. In certain embodiments, $R^3$ is alkoxy or substituted alkoxy. In certain embodiments, $R^3$ is amino or substituted amino. In certain embodiments, $R^3$ is acyl, carboxyl, carboxyl ester, or acylamino. In certain embodiments, $R^3$ is alkylamide or substituted alkylamide. In certain embodiments, $R^3$ is aryl or substituted aryl. For example, $R^3$ may be aryl, such as phenyl. In certain embodiments, $R^3$ is heteroaryl or substituted heteroaryl. In certain embodiments, $R^3$ is cycloalkyl or substituted cycloalkyl. In certain embodiments, $R^3$ is heterocyclyl or substituted heterocyclyl.

In certain embodiments, $R^3$ is —$R^9W$. In certain embodiments, W is selected from a drug, a detectable label and a polypeptide. In certain embodiments, W is a drug. In certain embodiments, W is a detectable label. In certain embodiments, W is a polypeptide. In certain embodiments, W may include a linker moiety through which the drug, detectable label or polypeptide is conjugated to the compound. For example, the linker moiety may include one or more monomer units, such as ethylene oxide of the formula —($CH_2$—$CH_2$—O)— or —(O—$CH_2$—$CH_2$)—. The number of such units can vary, with the number of such units being from 2 to 10, 2 to 8, 2 to 6, 2 to 4, for example some embodiments include 2 units. $R^9$ is described in more detail below.

In certain embodiments, $R^3$ is substituted with one or more groups to facilitate coupling of the compound to a second moiety. For instance, $R^3$ may be substituted with one or more reactive groups. In some cases, the reactive group(s) may be configured to react with a corresponding reactive partner on the second moiety (e.g., a drug, a detectable label, or a polypeptide) to facilitate coupling of the compound to the second moiety. For example, in certain embodiments, $R^3$ is substituted with one or more groups each independently selected from alkyl, substituted alkyl, alkoxy, substituted alkoxy, amino, substituted amino, carboxyl, carboxyl ester, amide, substituted amide, alkylamide, substituted alkylamide, aryl, substituted aryl, heteroaryl, substituted heteroaryl, cycloalkyl, substituted cycloalkyl, heterocyclyl, and substituted heterocyclyl.

In certain embodiments, $R^{11}$ is selected from alkyl, substituted alkyl, alkenyl, substituted alkenyl, alkynyl, substituted alkynyl, alkoxy, substituted alkoxy, amino, substituted amino, acyl, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl, and —$R^9W$. In certain embodiments, $R^{11}$ is alkyl or substituted alkyl. For instance, $R^{11}$ may be alkyl, such as $C_{1-6}$ alkyl, including $C_{1-3}$ alkyl. In some instances, $R^{11}$ is methyl. In certain embodiments, $R^{11}$ is alkenyl or substituted alkenyl. In certain embodiments, $R^{11}$ is alkynyl or substituted alkynyl. In certain embodiments, $R^{11}$ is alkoxy or substituted alkoxy. In certain embodiments, $R^{11}$ is amino or substituted amino. In certain embodiments, $R^{11}$ is acyl, carboxyl, carboxyl ester, or acylamino. In certain embodiments, $R^{11}$ is alkylamide or substituted alkylamide. In certain embodiments, $R^{11}$ is aryl or substituted aryl. For example, $R^{11}$ may be aryl, such as phenyl. In certain embodiments, $R^{11}$ is heteroaryl or substituted heteroaryl. In certain embodiments, $R^{11}$ is cycloalkyl or substituted cycloalkyl. In certain embodiments, $R^{11}$ is heterocyclyl or substituted heterocyclyl.

In certain embodiments, $R^{11}$ is —$R^9W$. In certain embodiments, W is selected from a drug, a detectable label and a polypeptide. In certain embodiments, W is a drug. In certain embodiments, W is a detectable label. In certain embodiments, W is a polypeptide. In certain embodiments, W may include a linker moiety through which the drug, detectable label or polypeptide is conjugated to the compound. For example, the linker moiety may include one or more monomer units, such as ethylene oxide of the formula —($CH_2$—$CH_2$—O)— or —(O—$CH_2$—$CH_2$)—. The number of such units can vary, with the number of such units being from 2 to 10, 2 to 8, 2 to 6, 2 to 4, for example some embodiments include 2 units. $R^9$ is described in more detail below.

In certain embodiments, $R^{11}$ is substituted with one or more groups to facilitate coupling of the compound to a second moiety. For instance, $R^{11}$ may be substituted with one or more reactive groups. In some cases, the reactive group(s) may be configured to react with a corresponding reactive partner on the second moiety (e.g., a drug, a detectable label, or a polypeptide) to facilitate coupling of the compound to the second moiety. For example, in certain embodiments, $R^{11}$ is substituted with one or more groups each independently selected from alkyl, substituted alkyl, alkoxy, substituted alkoxy, amino, substituted amino, carboxyl, carboxyl ester, amide, substituted amide, alkylamide, substituted alkylamide, aryl, substituted aryl, heteroaryl, substituted heteroaryl, cycloalkyl, substituted cycloalkyl, heterocyclyl, and substituted heterocyclyl.

In certain embodiments, $R^7$ is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester. In certain embodiments, $R^7$ is hydrogen. In certain embodiments, $R^7$ is halogen (e.g., F, Cl, Br or I). In certain embodiments, $R^7$ is F. In certain embodiments, $R^7$ is Cl. In certain embodiments, $R^7$ is Br. In certain embodiments, $R^7$ is I. In certain embodiments, $R^7$ is cyano. In certain embodiments, $R^7$ is alkyl or substituted alkyl. In certain embodiments, $R^7$ is alkenyl or substituted alkenyl. In certain embodiments, $R^7$ is alkynyl or substituted alkynyl. In certain embodiments, $R^7$ is alkylalkoxy or substituted alkylalkoxy. In certain embodiments, $R^7$ is acyl, carboxyl or carboxyl ester.

In certain embodiments, $R^{12}$ is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester. In certain embodiments, $R^{12}$ is hydrogen. In certain embodiments, $R^{12}$ is halogen (e.g., F, Cl, Br or I). In certain embodiments, $R^{12}$ is F. In certain embodiments, $R^{12}$ is Cl. In certain embodiments, $R^{12}$ is Br. In certain embodiments, $R^{12}$ is I. In certain embodiments, $R^{12}$ is cyano. In certain embodiments, $R^{12}$ is alkyl or substituted alkyl. In certain embodiments, $R^{12}$ is alkenyl or substituted alkenyl. In certain embodiments, $R^{12}$ is alkynyl or substituted alkynyl. In certain embodiments, $R^{12}$ is alkylalkoxy or substituted alkylalkoxy. In certain embodiments, $R^{12}$ is acyl, carboxyl or carboxyl ester.

In certain embodiments, $R^9$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, $R^9$ is alkyl or substituted alkyl. In certain embodiments, $R^9$ is alkenyl or substituted alkenyl. In certain embodiments, $R^9$ is alkynyl or substituted alkynyl. In certain embodiments, $R^9$ is alkoxy or substituted alkoxy. In certain embodiments, $R^9$ is amino or substituted amino. In certain embodiments, $R^9$ is carboxyl or carboxyl ester. In certain embodiments, $R^9$ is acylamino. In certain embodiments, $R^9$ is alkylamide or substituted alkylamide. In certain embodiments, $R^9$ is aryl or substituted aryl. In certain embodiments, $R^9$ is heteroaryl or substituted heteroaryl. In certain embodiments, $R^9$ is cycloalkyl or substituted cycloalkyl. In certain embodiments, $R^9$ is heterocyclyl or substituted heterocyclyl.

In certain embodiments, $R^{13}$ is selected from hydrogen, alkyl, substituted alkyl, alkenyl, substituted alkenyl, alkynyl, substituted alkynyl, alkoxy, substituted alkoxy, amino, substituted amino, acyl, carboxyl, carboxyl ester, acylamino, alkylamide, substituted alkylamide, and —$R^{14}W$. In certain embodiments, $R^{13}$ is hydrogen. In certain embodiments, $R^{13}$ is alkyl or substituted alkyl. In certain embodiments, $R^{13}$ is alkenyl or substituted alkenyl. In certain embodiments, $R^{13}$ is alkynyl or substituted alkynyl. In certain embodiments, $R^{13}$ is alkoxy or substituted alkoxy. In certain embodiments, $R^{13}$ is amino or substituted amino. In certain embodiments, $R^{13}$ is acyl, carboxyl, carboxyl ester, or acylamino. In certain embodiments, $R^{13}$ is alkylamide or substituted alkylamide.

In certain embodiments, $R^{13}$ is —$R^{14}W$. In certain embodiments, W is selected from a drug, a detectable label and a polypeptide. In certain embodiments, W is a drug. In certain embodiments, W is a detectable label. In certain embodiments, W is a polypeptide. In certain embodiments, W may include a linker moiety through which the drug, detectable label or polypeptide is conjugated to the compound. For example, the linker moiety may include one or more monomer units, such as ethylene oxide of the formula —($CH_2$—$CH_2$—O)— or —(O—$CH_2$—$CH_2$)—. The number of such units can vary, with the number of such units being from 2 to 10, 2 to 8, 2 to 6, 2 to 4, for example some embodiments include 2 units. $R^{14}$ is described in more detail below.

In certain embodiments, $R^{14}$ is selected from alkyl, substituted alkyl, alkenyl, substituted alkenyl, alkynyl, substituted alkynyl, alkoxy, substituted alkoxy, amino, substituted amino, carboxyl, carboxyl ester, acylamino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, $R^{14}$ is alkyl or substituted alkyl. In certain embodiments, $R^{14}$ is alkenyl or substituted alkenyl. In certain embodiments, $R^{14}$ is alkynyl or substituted alkynyl. In certain embodiments, $R^{14}$ is alkoxy or substituted alkoxy. In certain embodiments, $R^{14}$ is amino or substituted amino. In certain embodiments, $R^{14}$ is carboxyl, carboxyl ester or acylamino. In certain embodiments, $R^{14}$ is alkylamide or substituted alkylamide. In certain embodiments, $R^{14}$ is aryl or substituted aryl. In certain embodiments, $R^{14}$ is heteroaryl or substituted heteroaryl. In certain embodiments, $R^{14}$ is cycloalkyl or substituted cycloalkyl. In certain embodiments, $R^{14}$ is heterocyclyl or substituted heterocyclyl.

In certain embodiments, when X is CH, $R^{13}$ is H. In certain embodiments, when X is CH, $R^{13}$ is alkyl or substituted alkyl. For example, $R^{13}$ may be $C_{1-10}$ alkyl or $C_{1-10}$ substituted alkyl, such as $C_{1-8}$ alkyl or $C_{1-8}$ substituted alkyl, or $C_{1-6}$ alkyl or $C_{1-6}$ substituted alkyl, or $C_{1-4}$ alkyl or $C_{1-4}$ substituted alkyl. For instance, in some cases, the substituted alkyl may be substituted with an acylamino or aminoacyl group.

Target Polypeptides

Any of a wide variety of polypeptides can be modified to be conjugated to a second moiety as described above. Polypeptides suitable for modification include both proteins having a naturally-occurring amino acid sequence, fragments of naturally-occurring polypeptides, and non-naturally occurring polypeptides and fragments thereof.

The following are examples of classes and types of polypeptides which are of interest for modification using the compounds and methods described herein to produce the polypeptide conjugates described herein.

Therapeutic Polypeptides

In certain embodiments, the methods of producing a conjugate are applied to modification of polypeptides that may provide for a therapeutic benefit, such as those polypeptides for which attachment to a moiety can provide for one or more of, for example, an increase in serum half-life, a decrease in an adverse immune response, additional or alternate biological activity or functionality, and the like, or other benefit or reduction of an adverse side effect. Where the therapeutic polypeptide is an antigen for a vaccine, modification can provide for an enhanced immunogenicity of the polypeptide.

Examples of classes of therapeutic proteins include those that are cytokines, chemokines, growth factors, hormones, antibodies, and antigens. Further examples include, but are not limited to, the following: erythropoietin (EPO, e.g., native EPO or synthetic EPO (see, e.g., US 2003/0191291), such as, but not limited to, e.g., PROCRIT®, EPREX®, or EPOGEN® (epoetin-α), ARANESP® (darbepoietin-α), NEORECORMON®, EPOGIN® (epoetin-β), and the like); a growth hormone (e.g., a somatotropin, e.g., GENOTROPIN®, NUTROPIN®, NORDITROPIN®, SAIZEN®, SEROSTIM®, HUMATROPE®, etc.); human growth hormone (hGH); bovine growth hormone (bGH); follicle stimulating hormone (FSH); interferon (e.g., IFN-γ, IFN-α, IFN-β, IFN-ω; IFN-τ, consensus interferon, and the like); insulin (e.g., Novolin, Humulin, Humalog, Lantus, Ultralente, etc.), insulin-like growth factor (e.g., IGF-I, IGF-II); blood factors (e.g., Factor X, tissue plasminogen activator (TPA), and the like, such as, but not limited to, e.g., ACTIVASE® (alteplase) tissue plasminogen activator, NOVOSEVEN® (recombinant human factor VIIa), Factor VIIa, Factor VIII (e.g., KOGENATE®), Factor IX, β-globin, hemoglobin, and the like); colony stimulating factors (e.g., granulocyte-CSF (G-CSF, e.g., NEUPOGEN® (filgrastim)), macrophage-CSF (M-CSF), granulocyte-macrophage-CSF (GM-CSF), Neulasta (pegfilgrastim), granulocyte-monocyte colony stimulating factor, megakaryocyte colony stimulating factor, and the like), transforming growth factors (e.g., TGF-beta, TGF-alpha); interleukins (e.g., IL-1, IL-2 (e.g., Proleukin®), IL-3, IL-4, IL-5, IL-6, IL-7, IL-8, IL-9, IL-12, and the like); a growth factor (e.g., epidermal growth factor (EGF), platelet-derived growth factor (PDGF, e.g., REGRANEX® (beclapermin)), fibroblast growth factors (FGFs, e.g., aFGF, bFGF, such as FIBLAST® (trafermin)), glial cell line-derived growth factor (GDNF), nerve growth factor (NGF), stem cell factor (e.g., STEMGEN® (ancestim)), keratinocyte growth factor, a hepatocyte growth factor, and the like); a soluble receptor (e.g., a TNF-α-binding soluble receptor such as ENBREL® (etanercept), a soluble VEGF receptor, a soluble interleukin receptor, a soluble γ/δ T cell receptor, and the like); an enzyme (e.g., α-glucosidase, CERAZYME® (imiglucarase, β-glucocerebrosidase, CEREDASE® (alglucerase); an enzyme activator (e.g., tissue plasminogen activator); a chemokine (e.g., IP-10, Mig, Groα/IL-8, regulated and normal T cell expressed and secreted (RANTES), MIP-la, MIP-1β, MCP-1, PF-4, and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, galanin, growth hormone-releasing hormone, bombesin, warfarin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, a tissue factor, an insulin-like growth factor, a luteinizing hormone, a follicle stimulating hormone, a macrophage activating factor, tumor necrosis factor, a neutrophil chemotactic factor, a nerve growth factor, a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); and the like. It will be readily appreciated that native forms of the above therapeutic proteins are also of interest as target polypeptides in the present disclosure.

Further examples include antibodies, e.g., polyclonal antibodies, monoclonal antibodies, humanized antibodies, antigen-binding fragments (e.g., F(ab)', Fab, Fv), single chain antibodies, and the like (e.g., RITUXAN® (rituximab); REMICADE® (infliximab) HERCEPTIN® (trastuzumab); HUMIRA™ (adalimumab); XOLAIR™ (omalizumab); BEXXAR® (tositumomab); RAPTIVA™ (efalizumab); ERBITUX™ (cetuximab); and the like). In some instances, antibodies include antibodies that specifically bind to a tumor antigen, an immune cell antigen (e.g., CD4, CD8, and the like), an antigen of a microorganism, particularly a pathogenic microorganism (e.g., a bacterial, viral, fungal, or parasitic antigen), and the like.

In some instances, the methods, conjugates and compounds described herein can be applied to provide for a moiety (e.g., a water-soluble polymer) at a native or engineered site of glycosylation, such as found in hyperglycosylated forms of a therapeutic protein.

The biological activity of a modified target polypeptide can be assayed according to methods known in the art. Modified polypeptides that retain at least one desired pharmacologic activity of the corresponding parent protein are of interest.

Immunogenic Compositions

The methods, conjugates and compounds disclosed herein also find application in production of components of immunogenic compositions (e.g., therapeutic vaccines). For example, the compounds can be used to facilitate attachment of moieties that increase serum half-life of a polypeptide antigen, that increase immunogenicity of the polypeptide, or that link a non-amino acid antigen to a polypeptide carrier. In this regard, the compounds can be used to facilitate modification of microbial antigens (e.g., a bacterial, viral, fungal, or parasitic antigen), tumor antigens, and other antigens which are of interest for administration to a subject to elicit an immune response in the subject. Also of interest is modification of antigens that are useful in eliciting antibodies which can be useful as research tools.

Further examples of polypeptides of interest for modification using the compounds disclosed herein include those that are of interest for detection or functional monitoring in an assay (e.g., as a research tool, in a drug screening assay, and the like). Examples of polypeptides of this type include receptors (e.g., G-protein coupled receptors (GPCRs, including orphan GPCRs)), receptor ligands (including naturally-occurring and synthetic), protein channels (e.g., ion channels (e.g., potassium channels, calcium channels, sodium channels, and the like), and other polypeptides. In some embodiments, modification of cell surface-associated polypeptides, such as transmembrane polypeptides) is of interest, for example where such modification is accomplished while the polypeptide is present in a membrane. Methods for modification of a polypeptide under physiological conditions are described further below.

Methods of Polypeptide Production

In general, the polypeptides described herein may be expressed in prokaryotes or eukaryotes in accordance with conventional ways, depending upon the purpose for expression. Thus, the present invention further provides a host cell, e.g., a genetically modified host cell that comprises a nucleic acid encoding a polypeptide.

Host cells for production (including large scale production) of an unconjugated or modified polypeptide suitable to form a conjugate as described herein can be selected from any of a variety of available host cells. Examples of host cells include those of a prokaryotic or eukaryotic unicellular organism, such as bacteria (e.g., *Escherichia coli* strains, *Bacillus* spp. (e.g., *B. subtilis*), and the like) yeast or fungi (e.g., *S. cerevisiae, Pichia* spp., and the like), and other such host cells can be used. Examples of host cells originally derived from a higher organism such as insects, vertebrates, including mammals, (e.g., CHO, HEK, and the like), may be used as the expression host cells.

Suitable mammalian cell lines include, but are not limited to, HeLa cells (e.g., American Type Culture Collection (ATCC) No. CCL-2), CHO cells (e.g., ATCC Nos. CRL9618 and CRL9096), CHO DG44 cells (Urlaub (1983) *Cell* 33:405), CHO—K1 cells (ATCC CCL-61), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Specific expression systems of interest include bacterial, yeast, insect cell and mammalian cell derived expression systems.

The expressed polypeptide can be recovered by any appropriate means known in the art. Further, any convenient protein purification procedures may be employed, where suitable protein purification methodologies are described in Guide to Protein Purification, (Deuthser ed.) (Academic Press, 1990). For example, a lysate may prepared from a cell comprising the expression vector expressing the desired polypeptide, and purified using high performance liquid chromatography (HPLC), exclusion chromatography, gel electrophoresis, affinity chromatography, and the like.

Methods for Modification of a Polypeptide

In certain embodiments, the polypeptide may be conjugated to a moiety of interest without first modifying the polypeptide. For instance, the polypeptide may include one or more reactive groups suitable for conjugation to the moiety of interest (e.g., a moiety comprising a coupling moiety, such as a pyrazalinone or pyrazalinone derivative as described herein). In other embodiments, the polypeptide may be modified before conjugation to the moiety of interest. Modification of the polypeptide may produce a modified polypeptide that contains one or more reactive groups suitable for conjugation to the moiety of interest.

In some cases, the polypeptide may be modified at one or more amino acid residues to provide one or more reactive groups suitable for conjugation to the moiety of interest (e.g., a moiety comprising a coupling moiety, such as a pyrazalinone or pyrazalinone derivative as described herein). For example, carbonyls introduced into a polypeptide can be selectively reacted with α-nucleophiles, such as aminooxy- and hydrazide-bearing compounds. Chemistries selective for carbonyl functional groups on a protein with enhanced kinetics, site selectivity and conjugate stability may result in improved bioconjugates and provide access to new products and therapeutic targets as disclosed herein.

In certain embodiments, the polypeptide may be modified to include an aldehyde tag. By "aldehyde tag" or "ald-tag" is meant an amino acid sequence that contains an amino acid sequence derived from a sulfatase motif which is capable of being converted, or which has been converted, by action of a formylglycine generating enzyme (FGE) to contain a 2-formylglycine residue (referred to herein as "fGly"). The fGly residue generated by an FGE is often referred to in the literature as a "formylglycine". Stated differently, the term "aldehyde tag" is used herein to refer to an amino acid sequence comprising an "unconverted" sulfatase motif (i.e., a sulfatase motif in which the cysteine or serine residues has not been converted to fGly by an FGE, but is capable of being converted, such as a sulfatase motif with the sequence: L(C/S)TPSR (SEQ ID NO:1)) as well as to an amino acid sequence comprising a "converted" sulfatase motif (i.e., a sulfatase motif in which the cysteine or the serine residue has been converted to fGly by action of an FGE, e.g., L(fGly)TPSR (SEQ ID NO:2)). By "conversion" as used in the context of action of a formylglycine generating enzyme (FGE) on a sulfatase motif refers to biochemical modification of a cysteine or serine residue in a sulfatase motif to a formylglycine (fGly) residue (e.g., Cys to fGly, or Ser to fGly). Additional aspects of aldehyde tags and uses thereof in site-specific protein modification are described in U.S. Pat. No. 7,985,783, the disclosure of which is incorporated herein by reference.

Conversion of a polypeptide to include fGly can be accomplished by cell-based (in vivo) or cell-free methods (in vitro). Similarly, modification of a polypeptide to produce a polypeptide suitable for conjugation (e.g., modification to produce a polypeptide containing a reactive group suitable for conjugation) can be accomplished by cell-based (in vivo) or cell-free methods (in vitro).

Alternatively, isolated, unmodified polypeptides can be isolated following recombinant production in a host cell lacking a suitable enzyme or by synthetic production. The isolated polypeptide may then be contacted with a suitable enzyme under conditions to provide for the desired modification of the polypeptide to include fGly. The polypeptide can be unfolded by methods known in the art (e.g., using heat, adjustment of pH, chaotropic agents, (e.g., urea, and the like), organic solvents (e.g., hydrocarbons: octane, benzene, chloroform), etc.) and the denatured protein contacted with a suitable enzyme. The modified polypeptide can then be refolded under suitable conditions.

In some cases, the modified polypeptide containing the fGly residue may be conjugated to the moiety of interest by reaction of the fGly with a compound as described herein (e.g., a compound containing a coupling moiety, such as a pyrazalinone or pyrazalinone derivative as described herein). For example, an fGly-containing polypeptide may be isolated from a production source (e.g., recombinant host cell production, synthetic production), and contacted with a reactive partner-containing drug or other moiety (e.g., detectable label) under conditions suitable to provide for conjugation of the drug or other moiety to the polypeptide. For example, the reactive partner-containing drug or other moiety may include a reactive moiety (e.g., a pyrazalinone or pyrazalinone derivative as described herein). The pyrazalinone-containing drug or other moiety may be reacted with the polypeptide to produce a polypeptide conjugate as described herein. For example, FIG. 1 shows schematic drawings of polypeptide conjugates according to embodiments of the present disclosure. FIG. 1A shows a reaction scheme for the production of a polypeptide conjugate that includes a cyclic coupling moiety. In FIG. 1A, a polypeptide that includes an fGly is reacted with a cyclic coupling moiety (e.g., a pyrazalinone or pyrazalinone derivative) to produce a polypeptide conjugate that includes the cyclic coupling moiety. FIG. 1B shows a reaction scheme for the production of a polypeptide conjugate that includes an acyclic coupling moiety. In FIG. 1B, a polypeptide that includes an fGly is reacted with an acyclic coupling moiety to produce a polypeptide conjugate that includes the acyclic coupling moiety.

In some cases, the modified polypeptide containing the fGly residue may be conjugated to the moiety of interest by reaction of the fGly with a compound such as, but not limited to, one of the following compounds:

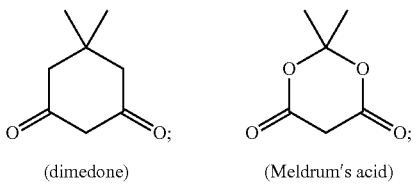

(dimedone)   (Meldrum's acid)

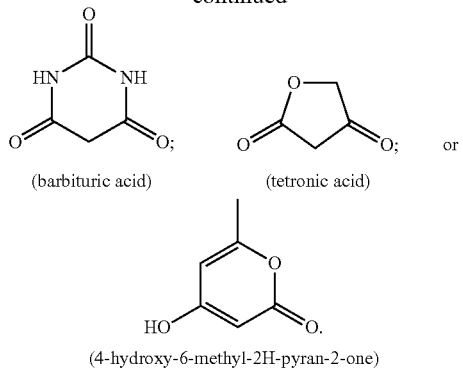

(barbituric acid)   (tetronic acid)

(4-hydroxy-6-methyl-2H-pyran-2-one)

Polypeptide Conjugates

The polypeptides can be subjected to conjugation to provide for attachment of a wide variety of moieties. Examples of moieties of interest include, but are not limited to, a drug, a detectable label, a small molecule, a water-soluble polymer, a peptide, and the like (also referred to a "payload" or "cargo" herein). Thus, the present disclosure provides a polypeptide conjugate as described above.

The moiety of interest is provided as a component of a reactive partner for reaction with a residue of a polypeptide. In certain embodiments, the methods of polypeptide conjugation are compatible with reaction conditions suitable for the polypeptide. For example, the reaction conditions may include a reaction mixture that includes water. In some cases, the reaction mixture may have a pH compatible with the polypeptide, such as, but not limited to, a pH of 4 to 11, or a pH of 5 to 10, or a pH of 6 to 9, or a pH of 6 to 8. In certain instances, the reaction mixture has a pH of 7. In some embodiments, the reaction conditions are performed at a temperature compatible with the polypeptide. For example, the reaction conditions may be at a temperature of 20° C. to 45° C., such as 25° C. to 40° C., or 30° C. to 40° C., or 35° C. to 40° C. In some cases, the reaction conditions are at room temperature (e.g., 25° C.). In some instances, the reaction conditions are at a temperature of 37° C.

Provided the present disclosure, the ordinarily skilled artisan can readily adapt any of a variety of moieties to provide a reactive partner for conjugation to a polypeptide as contemplated herein. The ordinarily skilled artisan will appreciate that factors such as pH and steric hindrance (i.e., the accessibility of the modified amino acid residue to reaction with a reactive partner of interest) are of importance. Modifying reaction conditions to provide for optimal conjugation conditions is well within the skill of the ordinary artisan, and is routine in the art. Where conjugation is conducted with a polypeptide present in or on a living cell, the conditions are selected so as to be physiologically compatible. For example, the pH can be dropped temporarily for a time sufficient to allow for the reaction to occur but within a period tolerated by the cell (e.g., from about 30 min to 1 hour). Physiological conditions for conducting modification of polypeptides on a cell surface can be similar to those used in a ketone-azide reaction in modification of cells bearing cell-surface azides (see, e.g., U.S. Pat. No. 6,570,040).

In certain embodiments, the present disclosure provides a polypeptide conjugate, where the polypeptide is an antibody. As such, embodiments include an antibody conjugated to a moiety of interest, where an antibody conjugated to a moiety of interest is referred to as an "antibody conjugate." An Ig polypeptide generally includes at least an Ig heavy chain constant region or an Ig light chain constant region, and can further include an Ig variable region (e.g., a $V_L$ region and/or a $V_H$ region). Ig heavy chain constant regions include Ig constant regions of any heavy chain isotype, non-naturally occurring Ig heavy chain constant regions (including consensus Ig heavy chain constant regions). An Ig constant region can be modified to be conjugated to a moiety of interest, where the moiety of interest is present in or adjacent a solvent-accessible loop region of the Ig constant region.

In some cases, an antibody conjugate of the present disclosure can include: 1) Ig heavy chain constant region conjugated to one or more moieties of interest, and an Ig light chain constant region conjugated to one or more moieties of interest; 2) an Ig heavy chain constant region conjugated to one or more moieties of interest, and an Ig light chain constant region that is not conjugated to a moiety of interest; or 3) an Ig heavy chain constant region that is not conjugated to a moiety of interest, and an Ig light chain constant region conjugated to one or more moieties of interest. A subject antibody conjugate can also include variable VH and/or VL domains. As described above, the one or more moieties of interest may be conjugated to the Ig heavy chain constant region or the Ig light chain constant region at a single amino acid residue (e.g., one or two moieties of interest conjugated to a single amino acid residue), or conjugated to the Ig heavy chain constant region and/or the Ig light chain constant region at two or more different amino acid residues.

An antibody conjugate of the present disclosure can include, as the conjugated moiety, any of a variety of compounds, as described herein, e.g., a drug (e.g., a peptide drug, a small molecule drug, and the like), a water-soluble polymer, a detectable label, a synthetic peptide, etc.

An antibody conjugate can have any of a variety of antigen-binding specificities, as described above, including, e.g., an antigen present on a cancer cell; an antigen present on an autoimmune cell; an antigen present on a pathogenic microorganism; an antigen present on a virus-infected cell (e.g., a human immunodeficiency virus-infected cell), e.g., CD4 or gp120; an antigen present on a diseased cell; and the like. For example, an antibody conjugate can bind an antigen, as noted above, where the antigen is present on the surface of the cell. An antibody conjugate of the present disclosure can bind antigen with a suitable binding affinity, e.g., from $5\times10^{-6}$ M to $10^{-7}$ M, from $10^{-7}$ M to $5\times10^{-7}$ M, from $5\times10^{-7}$ M to $10^{-8}$ M, from $10^{-8}$ M to $5\times10^{-8}$ M, from $5\times10^{-8}$ M to $10^{-9}$ M, or a binding affinity greater than $10^{-9}$ M.

As non-limiting examples, a subject antibody conjugate can bind an antigen present on a cancer cell (e.g., a tumor-specific antigen; an antigen that is over-expressed on a cancer cell; etc.), and the conjugated moiety can be a cytotoxic compound (e.g., a cytotoxic small molecule, a cytotoxic synthetic peptide, etc.). For example, a subject antibody conjugate can be specific for CD19, where the conjugated moiety is a cytotoxic compound (e.g., a cytotoxic small molecule, a cytotoxic synthetic peptide, etc.). As another example, a subject antibody conjugate can be specific for CD22, where the conjugated moiety can be a cytotoxic compound (e.g., a cytotoxic small molecule, a cytotoxic synthetic peptide, etc.).

As further non-limiting examples, a subject antibody conjugate can bind an antigen present on a cell infected with a virus (e.g., where the antigen is encoded by the virus; where the antigen is expressed on a cell type that is infected by a virus; etc.), and the conjugated moiety can be a viral fusion inhibitor. For example, a subject antibody conjugate can bind CD4, and the conjugated moiety can be a viral fusion inhibitor. As another example, a subject antibody conjugate can bind gp120, and the conjugated moiety can be a viral fusion inhibitor.

Embodiments of the present disclosure also include polypeptide conjugates where the polypeptide is a carrier protein. For example, carrier proteins can be covalently and site-specifically bound to drug to provide a drug-containing scaffold. A carrier protein can be site-specifically conjugated to a covalently bound molecule of interest, such as a drug (e.g., a peptide, a small molecule drug, and the like), detectable label, etc. In certain embodiments, drug-scaffold conjugates can provide for enhanced serum half-life of the drug.

In general a "carrier protein" is a protein that is biologically inert, is susceptible to modification as disclosed herein, and which can provide for solvent-accessible presentation of the moiety of interest conjugated to the carrier protein through a modified amino acid residue in the carrier protein (e.g., through an oxime or hydrazone bond within the converted sulfatase motif of an aldehyde tagged carrier protein) in a physiological environment. "Biologically inert" is meant to indicate the carrier protein exhibits clinically insignificant or no detectable biological activity when administered to the appropriate subject, such as when administered to a human subject. Thus, carrier proteins are biologically inert in that they, for example, are of low immunogenicity, do not exhibit significant or detectable targeting properties (e.g., do not exhibit significant or detectable activity in binding to a specific receptor), and exhibit little or no detectable biological activity that may interfere with activity of the moiety (e.g., drug or detectable label) conjugated to the aldehyde-tagged carrier protein. By "low immunogenicity" is meant that the carrier protein elicits little or no detectable immune response upon administration to a subject, such as a mammalian subject, e.g., a human subject. Carrier proteins can be provided in monomeric or multimeric (e.g., dimeric) forms.

Carrier proteins having a three-dimensional structure when folded that provides for multiple different solvent-accessible sites that are amenable to modification (and thus conjugation to a moiety of interest) are of interest. In general, carrier proteins of interest are those that are of a size and three-dimensional folded structure so as to provide for presentation of the conjugated moiety of interest on solvent accessible surfaces in a manner that is sufficiently spatially separated so as to provide for activity and bioavailability of the conjugated moiety or moieties of interest. The carrier protein may be selected according to a variety of factors including, but not limited to, the moiety (e.g., drug or detectable label) to be conjugated to the carrier protein.

Accordingly, any of a wide variety of polypeptides can be suitable for use as carrier proteins for use in the carrier protein conjugates of the present disclosure. Such carrier proteins can include those having a naturally-occurring amino acid sequence, fragments of naturally-occurring polypeptides, and non-naturally occurring polypeptides and fragments thereof.

Examples of carrier proteins include, but are not limited to, albumin and fragments thereof (e.g., human serum albumin, bovine serum albumin, and the like), transferrin and fragments thereof (e.g. human transferrin), and Fc fragments having reduced binding to a mammalian Fc receptor, particularly a human Fc receptor (e.g., a modified Fc fragment of an antibody (e.g., IgG), such as a mammalian antibody, e.g., a human antibody). Examples of modified Fc fragments having reduced Fc receptor binding are exemplified by the Fc fragments of Herceptin (trastuzumab) and Rituxan (Rituximab), which contain point mutations that provide for reduced Fc receptor binding (see, e.g., Clynes et al., Nature Medicine (2000), 6, 443-446). Alternatively or in addition, the isotype of the Fc fragment can be selected according to a desired level of Fc receptor binding (e.g., use of an Fc fragment of an IgG4 isotype human heavy chain constant region rather than from IgG1 or IgG3. (see, e.g., Fridman FASEB J 1991 September; 5 (12): 2684-90). In general, carrier proteins can be at least about 4 kDa (e.g., about 50 amino acid residues in length), usually at least about 25 kDa, and can be larger in size (e.g., transferrin has a molecular weight of 90 kDa while Fc fragments can have molecular weights of 30 kDa to 50 kDa).

The conjugates described herein can be used for a variety of applications including, but not limited to, visualization using fluorescence or epitope labeling (e.g., electron microscopy using gold particles equipped with reactive groups for conjugation to the compounds and conjugates described herein); protein immobilization (e.g., protein microarray production); protein dynamics and localization studies and applications; and conjugation of proteins with a moiety of interest (e.g., moieties that improve a parent protein's half-life (e.g., poly(ethylene glycol)), targeting moieties (e.g., to enhance delivery to a site of action), and biologically active moieties (e.g., a therapeutic moiety).

The polypeptide conjugate may include a polypeptide conjugated to a moiety or moieties that provide for one or more of a wide variety of functions or features. In general, examples of moieties include, but are not limited to, the following: detectable labels (e.g., fluorescent labels); light-activated dynamic moieties (e.g., azobenzene mediated pore closing, azobenzene mediated structural changes, photo-decaging recognition motifs); water soluble polymers (e.g., PEGylation); purification tags (e.g., to facilitate isolation by affinity chromatography (e.g., attachment of a FLAG epitope); membrane localization domains (e.g., lipids or glycophosphatidylinositol (GPI)-type anchors); immobilization tags (e.g., to facilitate attachment of the polypeptide to a surface, including selective attachment); drugs (e.g., to facilitate drug targeting, e.g., through attachment of the drug to an antibody); targeted delivery moieties, (e.g., ligands for binding to a target receptor (e.g., to facilitate viral attachment, attachment of a targeting protein present on a liposome, etc.)), and the like.

Specific, non-limiting examples are provided below.

Drugs for Conjugation to a Polypeptide

Any of a number of drugs are suitable for use, or can be modified to be rendered suitable for use, as a reactive partner to conjugate to a polypeptide. Examples of drugs include small molecule drugs and peptide drugs. Thus, the present disclosure provides drug-polypeptide conjugates.

"Small molecule drug" as used herein refers to a compound, e.g., an organic compound, which exhibits a pharmaceutical activity of interest and which is generally of a molecular weight of 800 Da or less, or 2000 Da or less, but can encompass molecules of up to 5 kDa and can be as large as 10 kDa. A small inorganic molecule refers to a molecule containing no carbon atoms, while a small organic molecule refers to a compound containing at least one carbon atom.

"Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight.

In some cases, the drug is a cancer chemotherapeutic agent. For example, where the polypeptide is an antibody (or fragment thereof) that has specificity for a tumor cell, the antibody can be modified as described herein to include a modified amino acid, which can be subsequently conjugated to a cancer chemotherapeutic agent. Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used.

Suitable cancer chemotherapeutic agents include dolastatin and active analogs and derivatives thereof; and auristatin and active analogs and derivatives thereof. See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) *Proc. Natl. Acad. Sci. USA* 93:8618-8623); and duocarmycins and active analogs and derivatives thereof (e.g., including the synthetic analogues, KW-2189 and CB 1-TM1).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxon), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; and (9) inhibitors of angiogenesis.

Methods for Modification of Drugs to Contain a Reactive Partner

Drugs to be conjugated to a polypeptide may be modified to incorporate a reactive partner for reaction with the polypeptide. Where the drug is a peptide drug, the reactive moiety (e.g., aminooxy or hydrazide can be positioned at an N-terminal region, the N-terminus, a C-terminal region, the C-terminus, or at a position internal to the peptide. For example, an example of a method involves synthesizing a peptide drug having an aminooxy group. In this example, the peptide is synthesized from a Boc-protected precursor. An amino group of a peptide can react with a compound comprising a carboxylic acid group and oxy-N-Boc group. As an example, the amino group of the peptide reacts with 3-(2,5-dioxopyrrolidin-1-yloxy)propanoic acid. Other variations on the compound comprising a carboxylic acid group and oxy-N-protecting group can include different number of carbons in the alkylene linker and substituents on the alkylene linker. The reaction between the amino group of the peptide and the compound comprising a carboxylic acid group and oxy-N-protecting group occurs through standard peptide coupling chemistry. Examples of peptide coupling reagents that can be used include, but not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP—Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). As a non-limiting example, HOBt and DIC can be used as peptide coupling reagents.

Deprotection to expose the amino-oxy functionality is performed on the peptide comprising an N-protecting group. Deprotection of the N-oxysuccinimide group, for example, occurs according to standard deprotection conditions for a cyclic amide group. Deprotecting conditions can be found in Greene and Wuts, Protective Groups in Organic Chemistry, 3rd Ed., 1999, John Wiley & Sons, NY and Harrison et al. Certain deprotection conditions include a hydrazine reagent, amino reagent, or sodium borohydride. Deprotection of a Boc protecting group can occur with TFA. Other reagents for deprotection include, but are not limited to, hydrazine, methylhydrazine, phenylhydrazine, sodium borohydride, and methylamine. The product and intermediates can be purified by conventional means, such as HPLC purification.

The ordinarily skilled artisan will appreciate that factors such as pH and steric hindrance (i.e., the accessibility of the amino acid residue to reaction with a reactive partner of interest) are of importance, Modifying reaction conditions to provide for optimal conjugation conditions is well within the skill of the ordinary artisan, and is routine in the art. Where conjugation is conducted with a polypeptide present in or on a living cell, the conditions are selected so as to be physiologically compatible. For example, the pH can be dropped temporarily for a time sufficient to allow for the reaction to occur but within a period tolerated by the cell (e.g., from about 30 min to 1 hour). Physiological conditions for conducting modification of polypeptides on a cell surface can be similar to those used in a ketone-azide reaction in modification of cells bearing cell-surface azides (see, e.g., U.S. Pat. No. 6,570,040).

Small molecule compounds containing, or modified to contain, an α-nucleophilic group that serves as a reactive partner with a compound or conjugate disclosed herein are also contemplated for use as drugs in the polypeptide-drug conjugates of the present disclosure. General methods are known in the art for chemical synthetic schemes and conditions useful for synthesizing a compound of interest (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Peptide Drugs

In some cases, a conjugate comprises a covalently linked peptide. Suitable peptides include, but are not limited to, cytotoxic peptides; angiogenic peptides; anti-angiogenic peptides; peptides that activate B cells; peptides that activate T cells; anti-viral peptides; peptides that inhibit viral fusion; peptides that increase production of one or more lymphocyte populations; anti-microbial peptides; growth factors; growth hormone-releasing factors; vasoactive peptides; anti-inflammatory peptides; peptides that regulate glucose metabolism; an anti-thrombotic peptide; an anti-nociceptive peptide; a vasodilator peptide; a platelet aggregation inhibitor; an analgesic; and the like.

In some embodiments, the peptide can be chemically synthesized to include a group reactive with an amino acid residue or a modified amino acid residue of the polypeptide. A suitable synthetic peptide has a length of from 5 amino acids to 100 amino acids, or longer than 100 amino acids; e.g., a suitable peptide has a length of from 5 amino acids (aa) to 10 aa, from 10 aa to 15 aa, from 15 aa to 20 aa, from 20 aa to 25 aa, from 25 aa to 30 aa, from 30 aa to 40 aa, from 40 aa to 50 aa, from 50 aa to 60 aa, from 60 aa to 70 aa, from 70 aa to 80 aa, from 80 aa to 90 aa, or from 90 aa to 100 aa.

In certain embodiments, a peptide can be modified to contain an α-nucleophile-containing moiety (e.g., an aminooxy or hydrazide moiety), e.g., can be reacted with an fGly-containing polypeptide to yield a conjugate in which the polypeptide and peptide are linked by a hydrazone or oxime bond, respectively. Examples of methods of synthesizing a peptide, such that the synthetic peptide comprising a reactive group reactive with an amino acid residue or a modified amino acid residue of the polypeptide, are described above.

Suitable peptides include, but are not limited to, hLF-11 (an 11-amino acid N-terminal fragment of lactoferrin), an anti-microbial peptide; granulysin, an anti-microbial peptide; Plectasin (NZ2114; SAR 215500), an anti-microbial peptide; viral fusion inhibitors such as Fuzeon (enfuvirtide), TRI-1249 (T-1249; see, e.g., Matos et al. (2010) *PLoS One* 5:e9830), TRI-2635 (T-2635; see, e.g., Eggink et al. (2009) *J. Biol. Chem.* 284:26941), T651, and TRI-1144; C5a receptor inhibitors such as PMX-53, JPE-1375, and JSM-7717; POT-4, a human complement factor C3 inhibitor; Pancreate (an INGAP derivative sequence, a HIP-human proislet protein); somatostatin; a somatostatin analog such as DEBIO 8609 (Sanvar), octreotide, octreotide (C2L), octreotide QLT, octreotide LAR, Sandostatin LAR, SomaLAR, Somatuline (lanreotide), see, e.g., Deghenghi et al. (2001) *Endocrine* 14:29; TH9507 (Tesamorelin, a growth hormone-releasing factor); POL7080 (a protegrin analog, an anti-microbial peptide); relaxin; a corticotropin releasing factor agonist such as urotensin, sauvagine, and the like; a heat shock protein derivative such as DiaPep277; a human immunodeficiency virus entry inhibitor; a heat shock protein-20 mimic such as AZX100; a thrombin receptor activating peptide such as TP508 (Chrysalin); a urocortin 2 mimic (e.g., a CRF2 agonist) such as urocortin-2; an immune activator such as Zadaxin (thymalfasin; thymosin-al), see, e.g., Sjogren (2004) *J. Gastroenterol. Hepatol.* 19:S69; a hepatitis C virus (HCV) entry inhibitorE2 peptide such as HCV3; an atrial natriuretic peptide such as HANP (Sun 4936; carperitide); an annexin peptide; a defensin (anti-microbial peptide) such as hBD2-4; a defensin (anti-microbial peptide) such as hBD-3; a defensin (anti-microbial peptide) such as PMX-30063; a histatin (anti-microbial peptide) such as histatin-3, histatin-5, histatin-6, and histatin-9; a histatin (anti-microbial peptide) such as PAC-113; an indolicidin (anti-microbial peptide) such as MX-594AN (Omniganin; CLS001); an indolicidin (anti-microbial peptide) such as Omnigard (MBI-226; CPI-226); an anti-microbial peptide such as an insect cecropin; an anti-microbial peptide such as a lactoferrin (talactoferrin); an LL-37/cathelicidin derivative (an anti-microbial peptide) such as P60.4 (OP-145); a magainin (an anti-microbial peptide) such as Pexiganan (MSI-78; Suponex); a protegrin (an anti-microbial peptide) such as IB-367 (Iseganan); an agan peptide; a beta-natriuretic peptide such as Natrecor, or Noratak (Nesiritide), or ularitide; bivalarudin (Angiomax), a thrombin inhibitor; a C peptide derivative; a calcitonin such as Miacalcin (Fortical); an enkephalin derivative; an erythropoiesis-stimulating peptide such as Hematide; a gap junction modulator such as Danegaptide (ZP1609); a gastrin-releasing peptide; a ghrelin; a glucagon-like peptide; a glucagon-like peptide-2 analog such as ZP1846 or ZP1848; a glucosaminyl muramyl dipeptide such as GMDP; a glycopeptide antibiotic such as Oritavancin; a teicoplanin derivative such as Dalbavancin; a gonadotropin releasing hormone (GnRH) such as Zoladex (Lupon) or Triptorelin; a histone deacetylase (HDAC) inhibitor depsipeptide such as PMO2734 (Irvalec); an integrin such as eptifibatide; an insulin analog such as Humulog; a kahalalide depsipeptide such as PMO2734; a kallikrein inhibitor such as Kalbitor (ecallantide); an antibiotic such as Telavancin; a lipopeptide such as Cubicin or MX-2401; a lutenizing hormone releasing hormone (LHRH) such as goserelin; an LHRH synthetic decapeptide agonist analog such as Treistar (triptorelin pamoate); an LHRH such as Eligard; an M2 protein channel peptide inhibitor; metreleptin; a melanocortin receptor agonist peptide such as bremalanotide/PT-141; a melanocortin; a muramyl tripeptide such as Mepact (mifamurtide); a myelin basic protein peptide such as MBP 8298 (dirucotide); an N-type voltage-gated calcium channel blocker such as Ziconotide (Prialt); a parathyroid hormone peptide; a parathyroid analog such as 768974; a peptide hormone analog such as UGP281; a prostaglandin F2-α receptor inhibitor such as PDC31; a protease inhibitor such as PPL-100; surfaxin; a thrombospondin-1 (TSP-1) mimetic such as CVX-045 or ABT 510; a vasoactive intestinal peptide; vasopressin; a Y2R agonist peptide such as RG7089; obinepeptide; and TM30339.

Detectable Labels

The conjugates, compounds and methods of the present disclosure can be used to conjugate a detectable label to polypeptide. Examples of detectable labels include, but are not limited to, fluorescent molecules (e.g., autofluorescent molecules, molecules that fluoresce upon contact with a reagent, etc.), radioactive labels (e.g., $^{111}$In, $^{125}$I, $^{131}$I, $^{212}$B, $^{90}$Y, $^{186}$Rh, and the like), biotin (e.g., to be detected through reaction of biotin and avidin), fluorescent tags, imaging reagents, and the like. Detectable labels also include peptides or polypeptides that can be detected by antibody binding, e.g., by binding of a detectably labeled antibody or by detection of bound antibody through a sandwich-type assay. Further examples of detectable labels include, but are not limited to, dye labels (e.g., chromophores, fluorophores, such as, but not limited to, Alexa Fluor® fluorescent dyes (e.g., Alexa Fluor® 350, 405, 430, 488, 532, 546, 555, 568, 594, 595, 610, 633, 635, 647, 660, 680, 700, 750, 790, and the like)), biophysical probes (spin labels, nuclear magnetic resonance (NMR) probes), Förster Resonance Energy Transfer (FRET)-type labels (e.g., at least one member of a FRET pair, including at least one member of a fluorophore/quencher pair), Bioluminescence Resonance Energy Transfer (BRET)-type labels (e.g., at least one member of a BRET pair), immunodetectable tags (e.g., FLAG, His(6), and the like), localization tags (e.g., to identify association of a tagged polypeptide at the tissue or molecular cell level (e.g., association with a tissue type, or particular cell membrane), and the like.

Attachment of Moieties for Delivery to a Target Site

Embodiments of the present disclosure also include a polypeptide conjugated to one or more moieties, such as, but not limited to, a drug (e.g., a small molecule drug), toxin, or other molecule for delivery to a target site (e.g., a cell) and which can provide for a pharmacological activity or can serve as a target for delivery of other molecules.

Also contemplated are conjugates that include one of a pair of binding partners (e.g., a ligand, a ligand-binding portion of a receptor, a receptor-binding portion of a ligand, etc.). For example, the conjugate can include a polypeptide that serves as a viral receptor and, upon binding with a viral envelope protein or viral capsid protein, facilitates attachment of virus to the cell surface on which the modified polypeptide is expressed. Alternatively, the conjugate may include an antigen that is specifically bound by an antibody (e.g., monoclonal antibody), to facilitate detection and/or separation of host cells expressing the modified polypeptide.

Attachment of Target Molecules to a Support

The methods can provide for conjugation of a polypeptide to a moiety to facilitate attachment of the polypeptide to a solid substrate (e.g., to facilitate assays), or to a moiety to facilitate easy separation (e.g., a hapten recognized by an antibody bound to a magnetic bead). In some embodiments, the methods are used to provide for attachment of a protein to an array (e.g., chip) in a defined orientation. For example, a polypeptide modified at a selected site (e.g., at or near the N-terminus) can be generated, and the methods, conjugates and compounds used to deliver a moiety to the modified polypeptide. The moiety can then be used as the attachment site for affixing the polypeptide to a support (e.g., solid or semi-solid support, such as a support suitable for use as a microchip in high-throughput assays).

Water-Soluble Polymers

In some cases, a conjugate includes a covalently linked water-soluble polymer. A moiety of particular interest is a water-soluble polymer. A "water-soluble polymer" refers to a polymer that is soluble in water and is usually substantially non-immunogenic, and usually has an atomic molecular weight greater than 1,000 Daltons. The methods, conjugates and compounds described herein can be used to attach one or more water-soluble polymers to a polypeptide. Attachment of a water-soluble polymer (e.g., PEG) to a polypeptide, such as a pharmaceutically active (e.g., therapeutic) polypeptide can be desirable as such modification can increase the therapeutic index by increasing serum half-life as a result of increased proteolytic stability and/or decreased renal clearance. Additionally, attachment of one or more polymers (e.g., PEGylation) can reduce immunogenicity of protein pharmaceuticals.

In some embodiments, the water-soluble polymer has an effective hydrodynamic molecular weight of greater than 5,000 Da, greater than 10,000 Da, greater than 20,000 to 500,000 Da, greater than 40,000 Da to 300,000 Da, greater than 50,000 Da to 70,000 Da, such as greater than 60,000 Da. In some embodiments, the water-soluble polymer has an effective hydrodynamic molecular weight of from 10 kDa to 20 kDa, from 20 kDa to 25 kDa, from 25 kDa to 30 kDa, from 30 kDa to 50 kDa, or from 50 kDa to 100 kDa. By "effective hydrodynamic molecular weight" is intended the effective water-solvated size of a polymer chain as determined by aqueous-based size exclusion chromatography (SEC). When the water-soluble polymer contains polymer chains having polyalkylene oxide repeat units, such as ethylene oxide repeat units, each chain can have an atomic molecular weight of 200 Da to 80,000 Da, or 1,500 Da to 42,000 Da, including 2,000 to 20,000 Da. Unless referred to specifically, molecular weight is intended to refer to atomic molecular weight. Linear, branched, and terminally charged water soluble polymers (e.g., PEG) may be used.

Polymers useful as moieties to be attached to a polypeptide can have a wide range of molecular weights, and polymer subunits. These subunits may include a biological polymer, a synthetic polymer, or a combination thereof. Examples of such water-soluble polymers include: dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylates of starch, polyalklyene glycol and derivatives thereof, including polyethylene glycol, methoxy-polyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrrolidone, aspartamide, and polyoxyethylated polyols, with the dextran and dextran derivatives, dextrine and dextrine derivatives. It will be appreciated that various derivatives of the specifically recited water-soluble polymers are also contemplated.

Water-soluble polymers such as those described above include polyalkylene oxide based polymers, such as polyethylene glycol "PEG" (See. e.g., "Poly(ethylene glycol) Chemistry: Biotechnical and Biomedical Applications", J. M. Harris, Ed., Plenum Press, New York, N.Y. (1992); and "Poly(ethylene glycol) Chemistry and Biological Applications", J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089,261; 5,100,992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,672,662; 5,637,749; 5,643,575; 5,650,388; 5,681,567; 5,686,110; 5,730,990; 5,739,208; 5,756,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966).

Examples of polymers of interest include those containing a polyalkylene oxide, polyamide alkylene oxide, or derivatives thereof, including polyalkylene oxide and polyamide alkylene oxide comprising an ethylene oxide repeat unit of the formula $-(CH_2-CH_2-O)-$. Further examples of polymers of interest include a polyamide having a molecular weight greater than 1,000 Daltons of the formula $-[C(O)-X-C(O)-NH-Y-NH]_n-$ or $-[NH-Y-NH-C(O)-X-C(O)]_n-$, where X and Y are divalent radicals that may be the same or different and may be branched or linear, and n is a discrete integer from 2-100, such as from 2 to 50, and where either or both of X and Y comprises a biocompatible, substantially non-antigenic water-soluble repeat unit that may be linear or branched. Further examples of water-soluble repeat units comprise an ethylene oxide of the formula $-(CH_2-CH_2-O)-$ or $-(O-CH_2-CH_2)-$. The number of such water-soluble repeat units can vary significantly, with the number of such units being from 2 to 500, 2 to 400, 2 to 300, 2 to 200, 2 to 100, for example from 2 to 50. An example of an embodiment is one in which one or both of X and Y is selected from: $-((CH_2)_{n1}-(CH_2-CH_2-O)_{n2}-(CH_2)-$ or $-((CH_2)_{n1}-(O-CH_2-CH_2)_{n2}-(CH_2)_{n-1}-)$, where n1 is 1 to 6, 1 to 5, 1 to 4, or 1 to 3, and where n2 is 2 to 50, 2 to 25, 2 to 15, 2 to 10, 2 to 8, or 2 to 5. A further example of an embodiment is one in which X is $-(CH_2-CH_2)-$, and where Y is $-(CH_2-(CH_2-CH_2-O)_3-CH_2-CH_2-CH_2)-$ or $-(CH_2-CH_2-CH_2-(O-CH_2-CH_2)_3-CH_2)-$.

The polymer can include one or more spacers or linkers. Examples of spacers or linkers include linear or branched moieties comprising one or more repeat units employed in a water-soluble polymer, diamino and or diacid units, natural or unnatural amino acids or derivatives thereof, as well as aliphatic moieties, including alkyl, aryl, heteroalkyl, heteroaryl, alkoxy, and the like, which can contain, for example, up to 18 carbon atoms or even an additional polymer chain.

The polymer moiety, or one or more of the spacers or linkers of the polymer moiety when present, may include polymer chains or units that are biostable or biodegradable. For example, polymers with repeat linkages have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable, e.g., polyurethanes ($-NH-C(O)-O-$)>polyorthoesters (—O—C((OR)(R'))—O—)>polyamides (—C(O)—NH—). Similarly, the linkage systems attaching a water-soluble polymer to a target molecule may be biostable or biodegradable, e.g., from less stable to more stable: carbonate (—O—C(O)—O—)>ester (—C(O)—O—)>urethane (—NH—C(O)—O—)>orthoester (—O—C((OR)(R'))—O—)>amide (—C(O)—NH—). In general, it may be desirable to avoid use of a sulfated polysaccharide, depending on the lability of the sulfate group. In addition, it may be less desirable to use polycarbonates and polyesters. These bonds are provided by way of example, and are not intended to limit the types of bonds employable in the polymer chains or linkage systems of the water-soluble polymers useful in the modified aldehyde tagged polypeptides disclosed herein.

Formulations

The conjugates (including antibody conjugates) of the present disclosure can be formulated in a variety of different ways. In general, where the conjugate is a polypeptide-drug conjugate, the conjugate is formulated in a manner compatible with the drug conjugated to the polypeptide, the condition to be treated, and the route of administration to be used.

The conjugate (e.g., polypeptide-drug conjugate) can be provided in any suitable form, e.g., in the form of a pharmaceutically acceptable salt, and can be formulated for any suitable route of administration, e.g., oral, topical or parenteral administration. Where the conjugate is provided as a liquid injectable (such as in those embodiments where they are administered intravenously or directly into a tissue), the conjugate can be provided as a ready-to-use dosage form, or as a reconstitutable storage-stable powder or liquid composed of pharmaceutically acceptable carriers and excipients.

Methods for formulating conjugates can be adapted from those available in the art. For example, conjugates can be provided in a pharmaceutical composition comprising a therapeutically effective amount of a conjugate and a pharmaceutically acceptable carrier (e.g., saline). The pharmaceutical composition may optionally include other additives (e.g., buffers, stabilizers, preservatives, and the like). In some embodiments, the formulations are suitable for administration to a mammal, such as those that are suitable for administration to a human.

Methods of Treatment

The polypeptide-drug conjugates of the present disclosure find use in treatment of a condition or disease in a subject that is amenable to treatment by administration of the parent drug (i.e., the drug prior to conjugation to the polypeptide). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

In the context of cancer, the term "treating" includes any or all of: reducing growth of a solid tumor, inhibiting replication of cancer cells, reducing overall tumor burden, and ameliorating one or more symptoms associated with a cancer.

The subject to be treated can be one that is in need of therapy, where the host to be treated is one amenable to treatment using the parent drug. Accordingly, a variety of subjects may be amenable to treatment using the polypeptide-drug conjugates disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of polypeptide-drug conjugate administered can be initially determined based on guidance of a dose and/or dosage regimen of the parent drug. In general, the polypeptide-drug conjugates can provide for targeted delivery and/or enhanced serum half-life of the bound drug, thus providing for at least one of reduced dose or reduced administrations in a dosage regimen. Thus, the polypeptide-drug conjugates can provide for reduced dose and/or reduced administration in a dosage regimen relative to the parent drug prior to being conjugated in an polypeptide-drug conjugate of the present disclosure.

Furthermore, as noted above, because the polypeptide-drug conjugates can provide for controlled stoichiometry of drug delivery, dosages of polypeptide-drug conjugates can be calculated based on the number of drug molecules provided on a per polypeptide-drug conjugate basis.

In some embodiments, multiple doses of a polypeptide-drug conjugate are administered. The frequency of administration of a polypeptide-drug conjugate can vary depending on any of a variety of factors, e.g., severity of the symptoms, condition of the subject, etc. For example, in some embodiments, a polypeptide-drug conjugate is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

Methods of Treating Cancer

The present disclosure provides methods for delivering a cancer chemotherapeutic agent to an individual having a cancer. The methods are useful for treating a wide variety of cancers, including carcinomas, sarcomas, leukemias, and lymphomas.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's B cell lymphoma; and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Synthesis of 3-Methyl Pyrazalinone Compounds

3-Methyl pyrazalinone compounds were synthesized as illustrated in Scheme 1, below:

Scheme 1

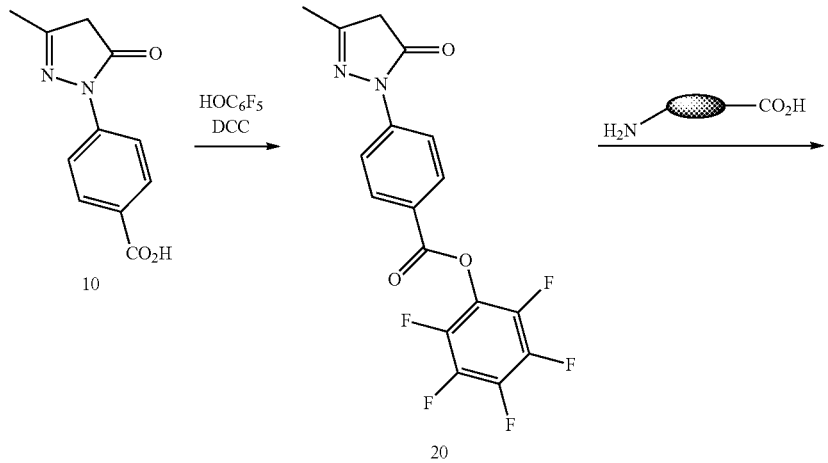

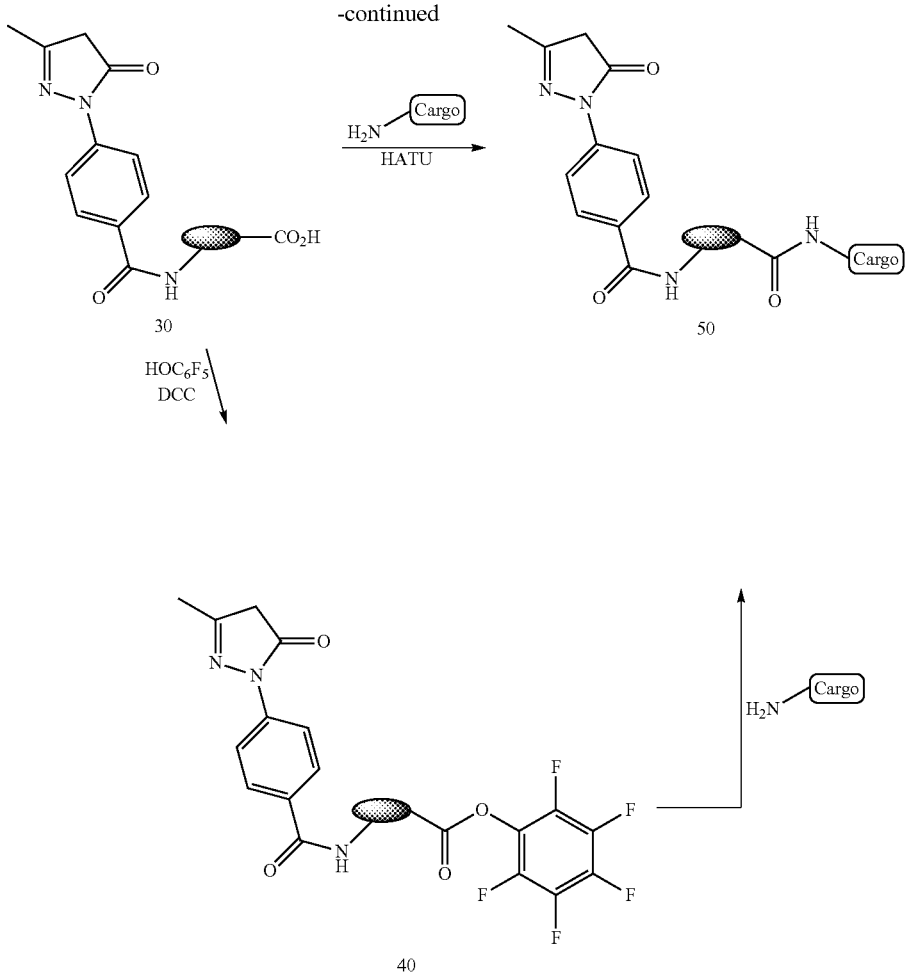

Compound 20 (perfluorophenyl 4-(3-methyl-5-oxo-4,5-dihydro-1H-pyrazol-1-yl)benzoate (Pz-PFP)) was synthesized from Compound 10 as follows. To a solution of 4-(3-methyl-5-oxo-4,5-dihydro-1H-pyrazol-1-yl)benzoic acid (429 mg, 1.97 mmol) in 2 mL ethyl acetate and 12 mL DMF was added pentafluorophenol (725 mg, 3.94 mmol) in 1 mL ethyl acetate and cooled the mixture to 0° C. To this solution was added 405 mg (1.97 mmol) of DCC in 1 mL EtOAc. The solution was stirred at 0° C. for one hour, then allowed to warm to room temperature over 4 hr. The crude reaction mixture was filtered through a PTFE syringe filter and loaded onto 10 g Biotage Silica Gel Samplet, which was chromatographed using a 10%-100% EtOAc:Hex gradient to yield a colorless solid. $^1$H NMR (400 MHz, CDCl$_3$) δ 8.28 (d, J=8.8 Hz, 2H), 8.15 (d, J=8.8 Hz, 2H), 3.52 (s, 2H), 2.27 (s, 3H). $^{19}$F NMR (400 MHz, CDCl$_3$) δ −152.4 (d, J=18.8 Hz), −158.1 (t, J=23.2 Hz), −162.4 (dd, J=23.2, 18.8 Hz). LRMS (ESI) calcd for C$_{17}$H$_9$F$_5$N$_2$O$_3$ [M+H]$^+$: 385.06. found 385.1.

Compound 30 (3-(4-(3-methyl-5-oxo-4,5-dihydro-1H-pyrazol-1-yl)benzamido)-linker-acid) was synthesized from Compound 20 as follows. A 4 mL vial was charged with 0.5 mg (1.36 µmol) Pz-PFP, to which a 200 µL solution of 1 mg (1.24 µmol) H$_2$N-Linker-CO$_2$H in DMA was added, followed by 0.21 mg (2.48 µmol) NaHCO$_3$ dissolved in 16 µL. This solution was stirred overnight. The reaction was acidified to pH 3 with 1M HCl and extracted thrice using DCM. The combined organic was then washed once with Brine and dried over MgSO$_4$. Purification of the crude reaction mixture was performed in two portions using C18 reverse phase HPLC (column type, column size, gradient).

Compound 50 (3-(4-(3-methyl-5-oxo-4,5-dihydro-1H-pyrazol-1-yl)benzamido)-linker-amide-cargo) was synthesized from Compound 30 as follows. A 4 mL vial was charged with 2.0 µmol (1 equiv) of 3-(4-(3-methyl-5-oxo-4,5-dihydro-1H-pyrazol-1-yl)benzamido)-linker acid, to which a 2 equiv of DIPEA and 2.0 µmol of HATU were added, followed by 2.0 µmol of H$_2$N-Cargo in 200 µL DMA. The solution was stirred for 3 hours and then purified by flash chromatography.

Synthesis of 3-(Tert-butyl) Pyrazalinone Compounds 3-(Tert-butyl) pyrazalinone compounds were synthesized as illustrated in Scheme 2, below:

Scheme 2
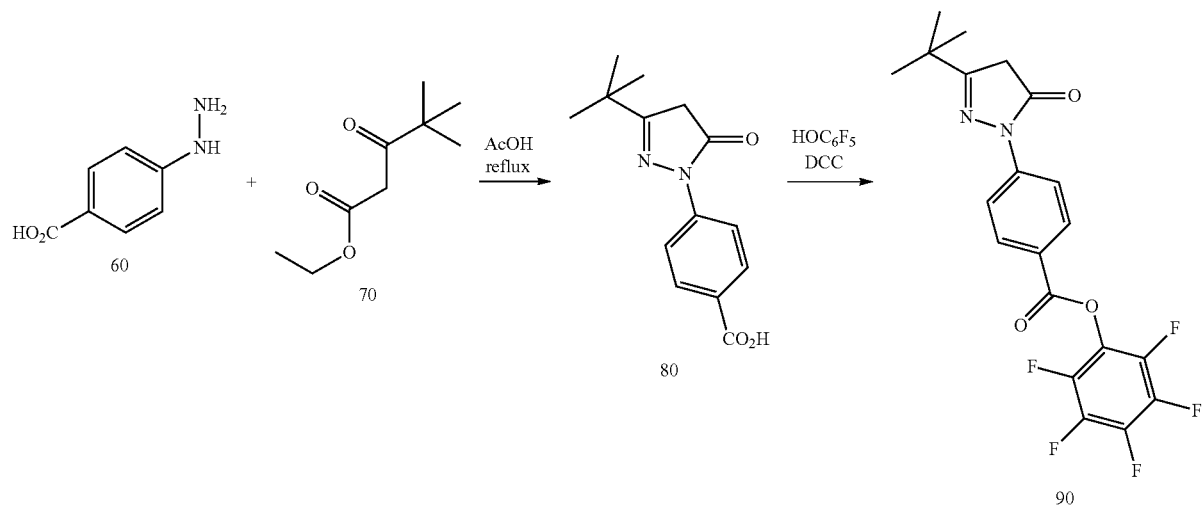
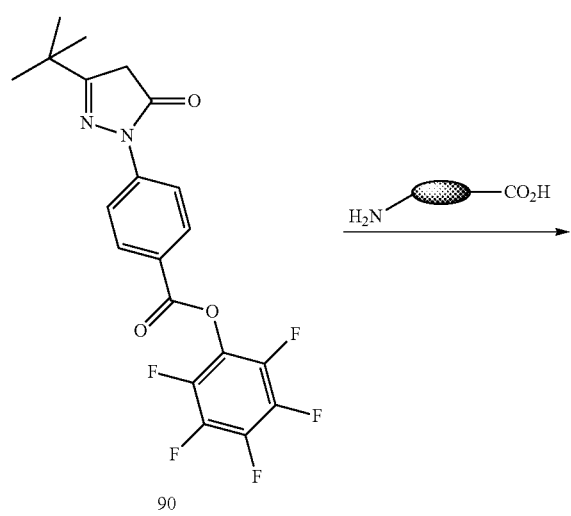
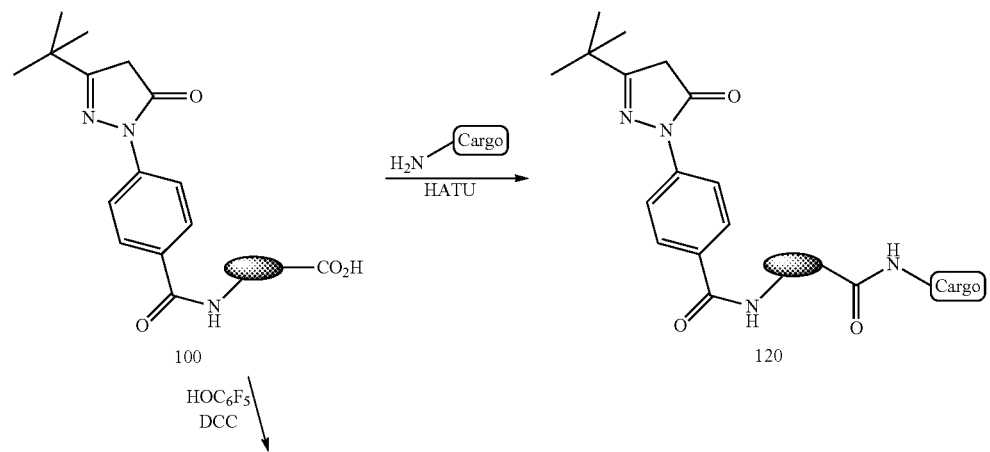

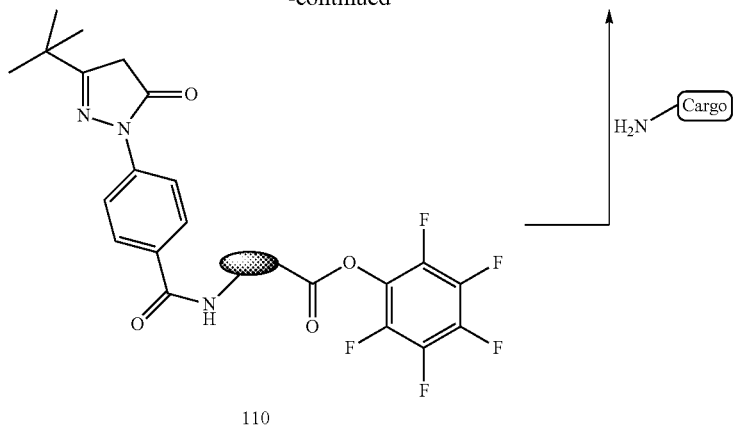

110

Compound 80 (4-(3-(tert-butyl)-5-oxo-4,5-dihydro-1H-pyrazol-1-yl)benzoic acid) was synthesized from Compounds 60 and 70 as follows. A 40 mL vial was charged with 400 mg 4-hydrazine benzoic acid hydrochloride (2.13 mmol, 1 equiv) followed by 5 mL acetic acid and 380 µL (2.13 mmol) ethyl 4,4-dimethyl-3-oxopentanoate and heated to reflux. The reaction was allowed to stir for 16 hr and then cooled to room temperature, upon which yellow crystals formed. The crystals were collected by filtration, washed with cold acetic acid, and pumped on overnight.

Compound 90 (perfluorophenyl 4-(3-(tert-butyl)-5-oxo-4,5-dihydro-1H-pyrazol-1-yl)benzoate) was synthesized from Compound 80 as follows. To a solution of 4-(3-(tert-butyl)-5-oxo-4,5-dihydro-1H-pyrazol-1-yl)benzoic acid (1.97 mmol) in 2 mL ethyl acetate and 12 mL DMF was added pentafluorophenol (3.94 mmol) in 1 mL ethyl acetate and cooled the mixture to 0° C. To this solution was added 405 mg (1.97 mmol) of DCC in 1 mL EtOAc. The solution was stirred at 0° C. for one hour, then allowed to warm to room temperature over 4 hr. The crude reaction mixture was filtered through a PTFE syringe filter and loaded onto 10 g Biotage Silica Gel Samplet, which was chromatographed using a 10%-100% EtOAc:Hex gradient to yield a colorless solid.

Compound 100 (4-(3-(tert-butyl)-5-oxo-4,5-dihydro-1H-pyrazol-1-yl)benzamido)-linker acid) was synthesized from Compound 90 as follows. A 4 mL vial was charged with Perfluorophenyl 4-(3-(tert-butyl)-5-oxo-4,5-dihydro-1H-pyrazol-1-yl)benzoate (2 µmol), to which a 200 µL solution of 1 mg (2 µmol) $H_2N$-Linker-$CO_2H$ in DMA was added, followed by 0.21 mg (3 µmol) $NaHCO_3$ dissolved in 16 µL. This solution was stirred overnight. The reaction was acidified to pH 3 with 1M HCl, and extracted thrice with DCM. The combined organic was then washed once with Brine and dried over $MgSO_4$. Purification of the crude reaction mixture was performed in two portions using C18 reverse phase HPLC (column type, column size, gradient).

Compound 120 (4-(3-(tert-butyl)-5-oxo-4,5-dihydro-1H-pyrazol-1-yl)benzamido)-linker-amide-cargo) was synthesized from Compound 100 as follows. A 4 mL vial was charged with 2.0 µmol (1 equiv) of 4-(3-(tert-butyl)-5-oxo-4,5-dihydro-1H-pyrazol-1-yl)benzamido)-linker acid, to which 2 equiv of DIPEA and 2.0 µmol (1 equiv) of HATU were added, followed by 2.0 µmol of $H_2N$-Cargo in 200 µL DMA. The solution was stirred for 3 hours and then purified by flash chromatography.

Synthesis of 3,4-Dimethyl Pyrazalinone Compounds 3,4-Dimethyl pyrazalinone compounds were synthesized as illustrated in Scheme 3, below:

Scheme 3

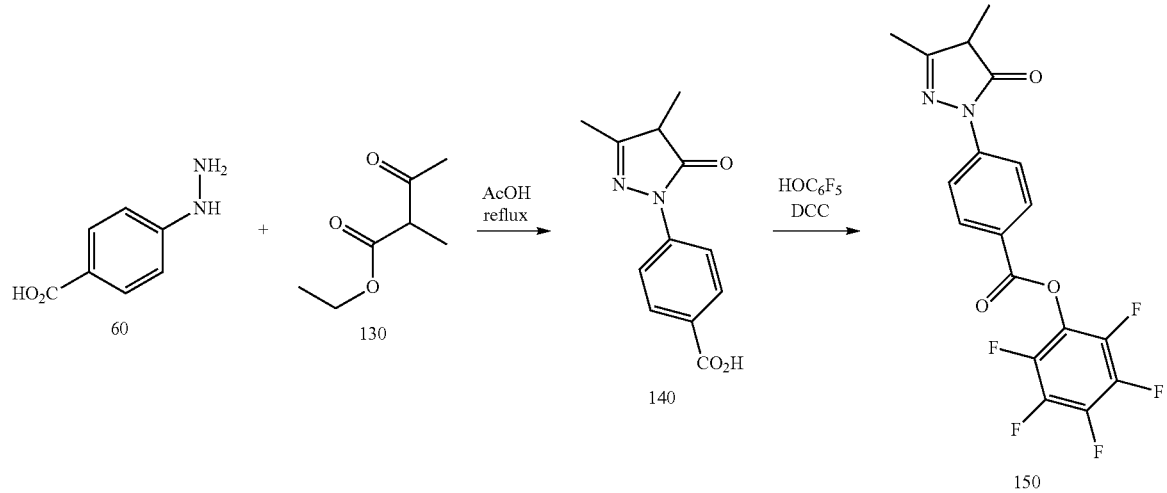

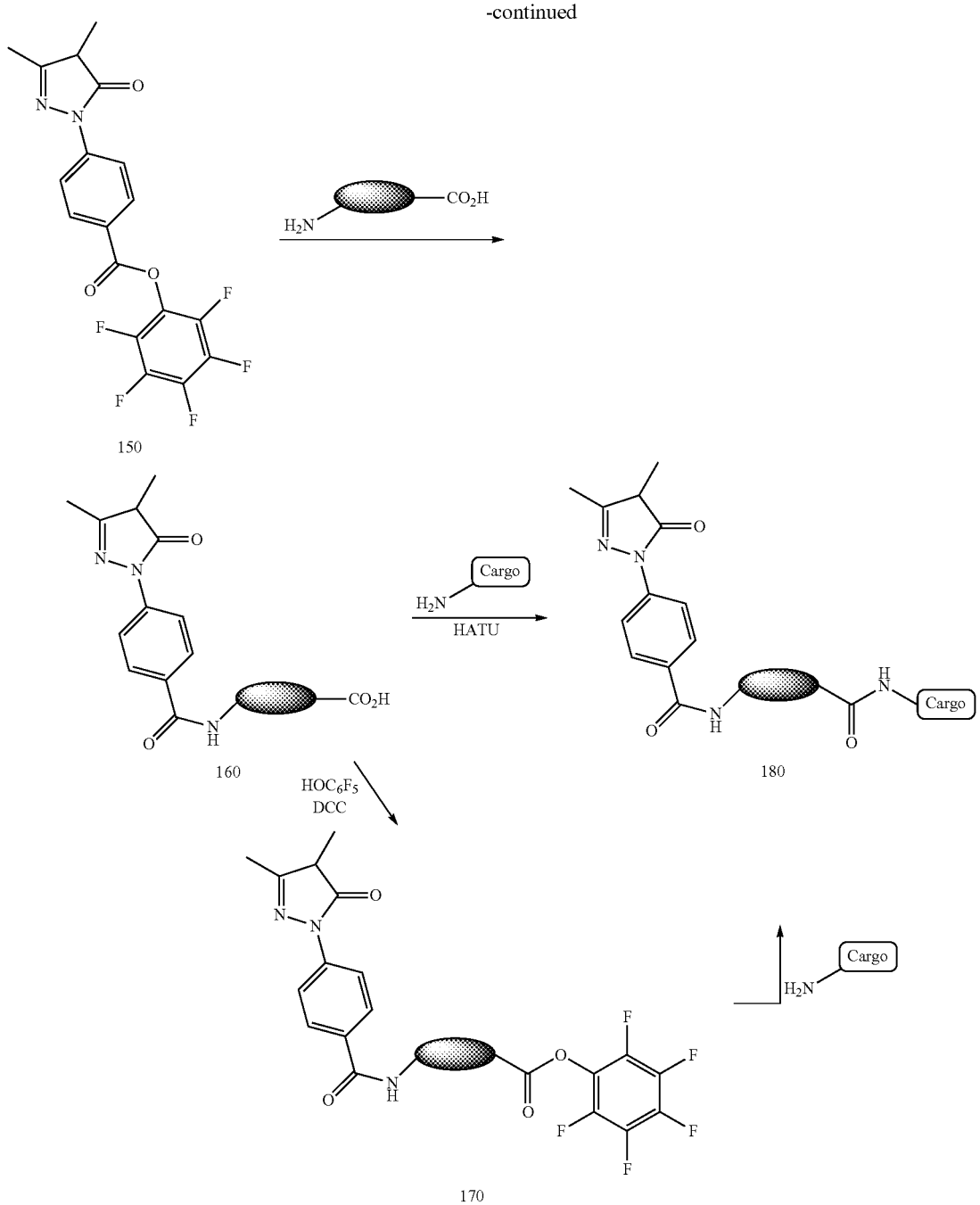

Compound 140 (4-(3,4-dimethyl-5-oxo-4,5-dihydro-1H-pyrazol-1-yl)benzoic acid) was synthesized from Compounds 60 and 130 as follows. A 40 mL vial was charged with 400 mg 4-hydrazine benzoic acid hydrochloride (2.13 mmol, 1 equiv) followed by 5 mL acetic acid and 2.13 mmol of ethyl 2-methyl-3-oxobutanoate and heated to reflux. The reaction was allowed to stir for 16 hr and then cooled to room temperature, upon which pink crystals formed. The crystals were collected by filtration, washed with cold acetic acid, and pumped on overnight.

Compound 150 (perfluorophenyl 4-(3,4-dimethyl-5-oxo-4,5-dihydro-1H-pyrazol-1-yl)benzoate) was synthesized from Compound 140 as follows. To a solution of 4-(3,4-dimethyl-5-oxo-4,5-dihydro-1H-pyrazol-1-yl)benzoic acid (1.97 mmol) in 2 mL ethyl acetate and 12 mL DMF was added pentafluorophenol (3.94 mmol) in 1 mL ethyl acetate and cooled the mixture to 0° C. To this solution was added 405 mg (1.97 mmol) of DCC in 1 mL EtOAc. The solution was stirred at 0° C. for one hour, then allowed to warm to room temperature over 4 hr. The crude reaction mixture was filtered through a PTFE syringe filter and loaded onto 10 g Biotage Silica Gel Samplet, which was chromatographed using a 10%-100% EtOAc:Hex gradient to yield a colorless solid.

Compound 160 (4-(3,4-dimethyl-5-oxo-4,5-dihydro-1H-pyrazol-1-yl)benzamido)-linker acid) was synthesized from Compound 150 as follows. A 4 mL vial was charged with perfluorophenyl 4-(3,4-dimethyl-5-oxo-4,5-dihydro-1H-pyrazol-1-yl)benzoate (2 µmol), to which a 200 µL solution of 2 µmol H$_2$N-Linker-CO$_2$H in DMA was added, followed by 0.21 mg (3 µmol) NaHCO$_3$ dissolved in 16 µL. This solution was stirred overnight. The reaction was acidified to pH 3 with 1M HCl and extracted thrice with DCM. The combined organic was then washed once with Brine and dried over MgSO$_4$. Purification of the crude reaction mixture was performed in two portions using C18 reverse phase HPLC (column type, column size, gradient).

Compound 180 (4-(3,4-dimethyl-5-oxo-4,5-dihydro-1H-pyrazol-1-yl)benzamido)-linker-amide-cargo) was synthesized from Compound 160 as follows. A 4 mL vial was charged with 2.0 µmol (1 equiv) of 4-(3,4-dimethyl-5-oxo-4,5-dihydro-1H-pyrazol-1-yl)benzamido)-linker acid, to which 2 equiv of DIPEA and 2.0 µmol (1 equiv) of HATU in 100 µL DMA were added, followed by 2.0 µmol of H$_2$N-Cargo in 200 µL DMA. The solution was stirred for 3 hours and then purified by flash chromatography.

Synthesis of 3-Methyl Pyrazalinone Compounds

3-Methyl pyrazalinone compounds were synthesized as illustrated in general reaction Scheme 4, below:

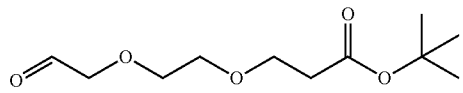

tert-Butyl 3-(2-(2-oxoethoxy)ethoxy)propanoate: To an oven-dried 20 mL vial charged with 1.67 mmol (707 mg) of Dess-Martin Periodinane was added 3.34 mmol (270 µL) pyridine followed by 2 mL DCM and sonicated until homogeneous. To this solution was added 1.39 mmol tert-Butyl 3-(2-(2-hydroxyethoxy)ethoxy)propanoate dissolved in 3 mL DCM and stirred for 3 h, after which 5 mL DCM, 5 mL 10% aqueous Na$_2$S$_2$O$_3$, and 5 mL saturated aqueous NaHCO$_3$ was added. This solution was stirred for 5 min, then extracted 1×5 mL saturated aqueous NaHCO$_3$ followed by 1×5 mL Brine. The organic layer was dried over MgSO$_4$, concentrated by rotary evaporation and chromatographed on silica gel using a 10-100% Ethyl Acetate: Hexanes gradient to yield 291.4 mg of desired product in 90% yield.

Scheme 4

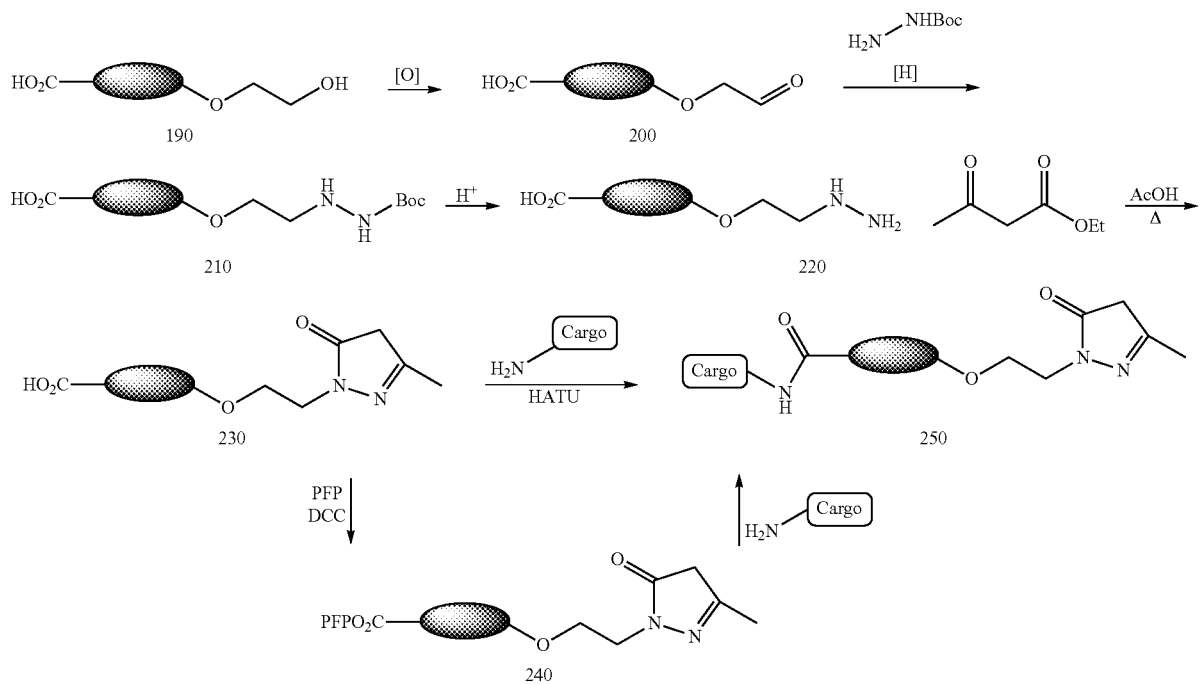

General reaction Scheme 4 was performed according to the reactions described in greater detail as follows:

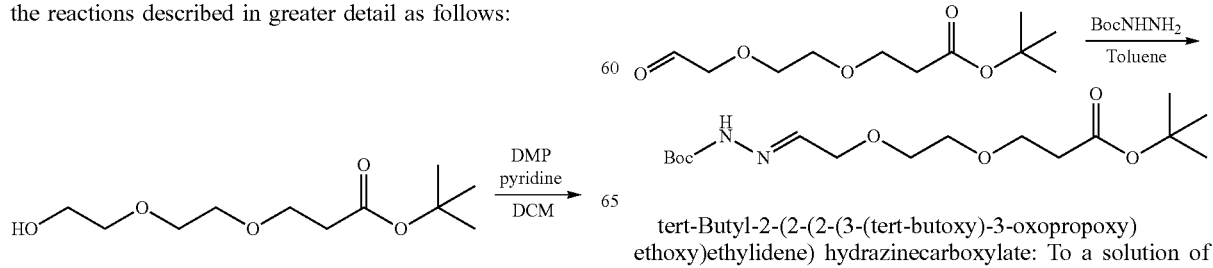

tert-Butyl-2-(2-(2-(3-(tert-butoxy)-3-oxopropoxy)ethoxy)ethylidene) hydrazinecarboxylate: To a solution of tert-butyl 3-(2-(2-oxoethoxy)ethoxy) propanoate (0.659 mmol, 153 mg) in 1 mL toluene was added tert-butyl carbazate (0.659 mmol). The solution was heated until homogeneous and maintained for 48 h. The reaction mixture was concentrated and advanced crude to the subsequent step.

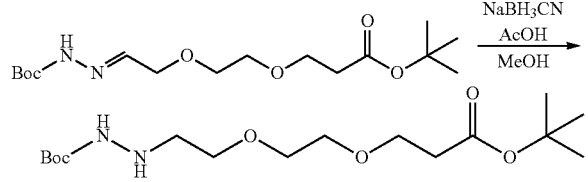

tert-Butyl 2-(2-(2-(3-(tert-butoxy)-3-oxopropoxy)ethoxy) ethyl) hydrazinecarboxylate: To a solution of tert-butyl-2-(2-(2-(3-(tert-butoxy)-3-oxopropoxy)ethoxy)ethylidene) hydrazinecarboxylate (0.659 mmol) and acetic acid (0.659 mmol) in methanol (2 mL) was added 0.725 mmol of NaBH₃CN in 1 mL MeOH and stirred overnight. The reaction was then quenched with 1 mL saturated aqueous NaHCO₃ and extracted with 3×5 mL Ethyl Acetate. The organics were combined and dried over MgSO₄, filtered, concentrated and chromatographed on silica gel using 10%-100% Ethyl Acetate: Hexanes to give the desired product.

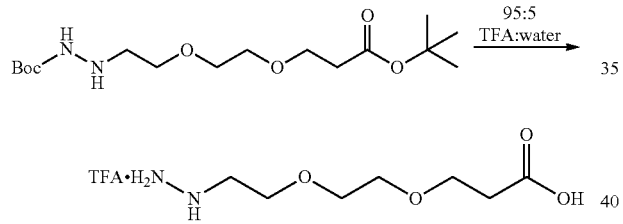

3-(2-(2-Hydrazinylethoxy)ethoxy)propanoic acid: A solution of 95:5 TFA:water was added to a 4 mL vial charged with tert-butyl 2-(2-(2-(3-(tert-butoxy)-3-oxopropoxy) ethoxy)ethyl)hydrazinecarboxylate. The reaction was maintained for 45 min then concentrated en vacuo. This material was used crude in the subsequent step.

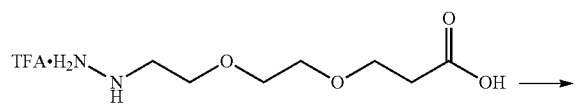

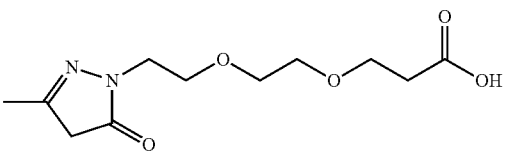

3-(2-(2-(3-methyl-5-oxo-4,5-dihydro-1H-pyrazol-1-yl) ethoxy)ethoxy)propanoic acid: A 40 mL vial was charged with 3-(2-(2-hydrazinylethoxy)ethoxy)propanoic acid by 5 mL acetic acid and ethyl 4,4-dimethyl-3-oxopentanoate and heated to reflux. The reaction was allowed to stir for 16 hr and then cooled to room temperature. The solution was concentrated en vacuo and chromatographed on silica gel using a 10-100% gradient to yield the desired product.

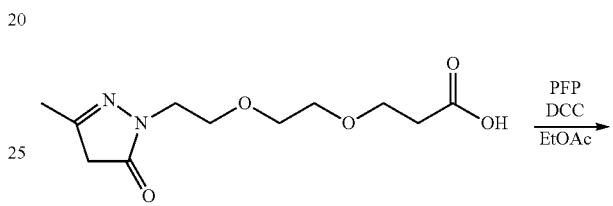

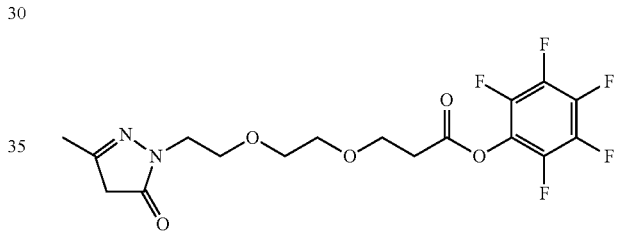

Perfluorophenyl 3-(2-(2-(3-methyl-5-oxo-4,5-dihydro-1H-pyrazol-1-yl)ethoxy)ethoxy)propanoate: To a solution of 3-(2-(2-(3-methyl-5-oxo-4,5-dihydro-1H-pyrazol-1-yl) ethoxy)ethoxy)propanoic acid (2 mmol) in 10 mL ethyl acetate was added pentafluorophenol (4 mmol) in 1 mL ethyl acetate and cooled to 0° C. To this solution was added (2 mmol) of DCC in 1 mL EtOAc. The solution was stirred at 0° C. for one hour, then allowed to warm to room temperature over 4 hr. The crude reaction mixture was filtered through a PTFE syringe filter and loaded onto 10 g Biotage Silica Gel Samplet (Biotage, Charlotte, N.C.), which was chromatographed using a 10%-100% EtOAc:Hex gradient to yield a colorless solid.

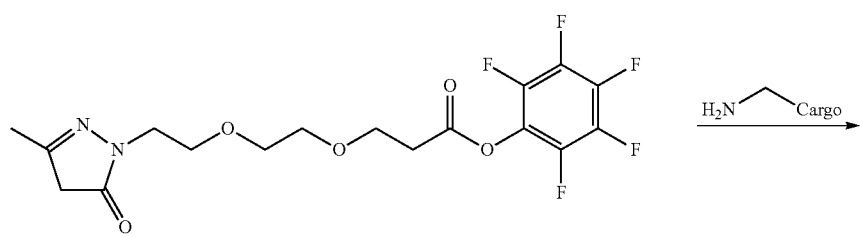

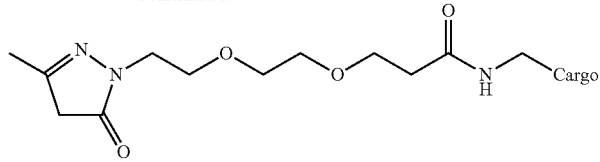

N-"Cargo"-3-(2-(2-(3-methyl-5-oxo-4,5-dihydro-1H-pyrazol-1-yl)ethoxy)ethoxy) propanamide: A 4 mL vial was charged with perfluorophenyl 3-(2-(2-(3-methyl-5-oxo-4,5-dihydro-1H-pyrazol-1-yl)ethoxy)ethoxy)propanoate, to which a 500 µL solution of H₂N-Cargo in DMA was added, followed 2 equivalents of NaHCO₃ dissolved in 50 µL and stirred for 4 h. The crude reaction was purified by silica gel chromatography using a 10-100% Ethyl Acetate:Hexanes gradient to yield the desired product.

Example 1

Experiments were performed to produce a conjugate comprising a fluorescent detectable label and a pyrazalinone coupling moiety according to Scheme 5 below.

Scheme 5

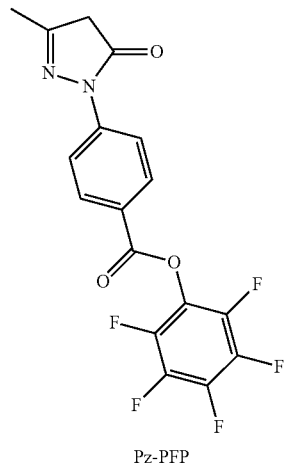

Pz-PFP

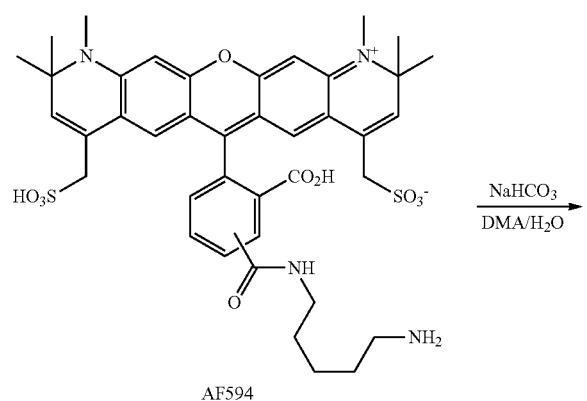

AF594

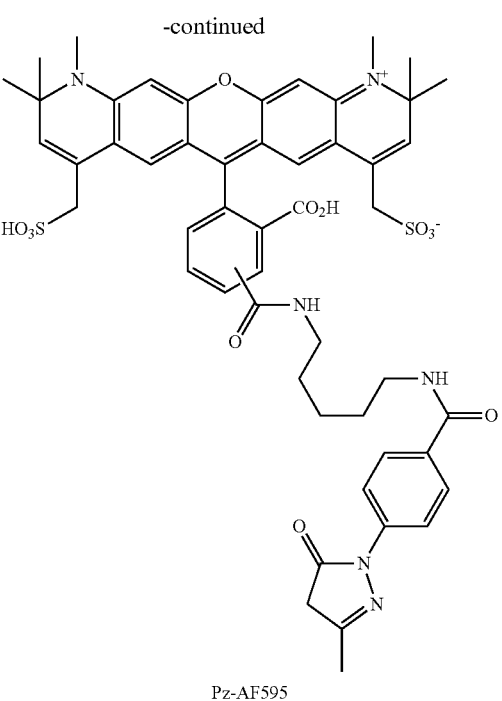

Pz-AF595

A 4 mL vial was charged with 0.5 mg (1.36 µmol) Pz-PFP, to which a 200 µL solution of 1 mg (1.24 µmol) in DMA was added, followed by 0.21 mg (2.48 µmol) NaHCO₃ dissolved in 16 µL. This solution was stirred for 3 days. Purification of the crude reaction mixture was performed in two portions using C18 reverse phase HPLC (Agilent poroshell 120, 4.6 mm×50 mm, 60% AcCN:40% H₂O to 100% AcCN) to yield 0.8 mg of a purple film. LRMS (ESI) calculated for $C_{17}H_9F_5N_2O_3$ [M−H]⁻: 1005.32. found 1005.1.

Example 2

Conjugation of FGly-Containing Peptides with Ligation Reagents

The following reagents were combined and aliquots taken at 1, 2, 4 and 5 hours and the reaction monitored for product formation at 215 nm by C18 RP HPLC:

10 µL of 10 mM H₂N-GPSVFPL(fGly)TPSR—OH (SEQ ID NO:3) in MilliQ water;

either 1×DPBS, pH 7.4 (80 µL) or 100 mM KOAc, pH 4.6 (80 µL); and 50 mM Pz in 1:3 MeCN:MilliQ water (10 µL).

Figure 2:
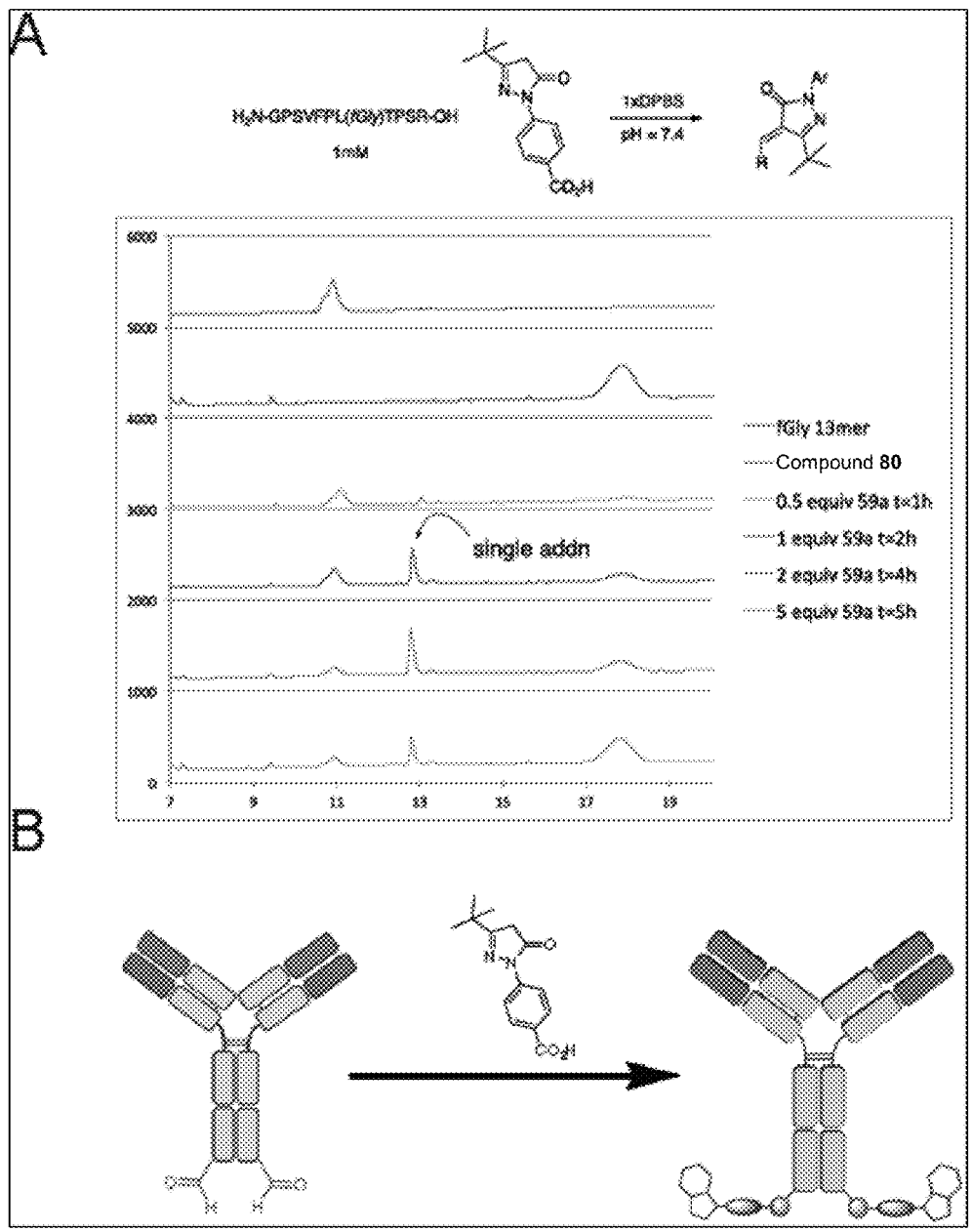
FIG. 2 shows the reactivity of a functionalized compound to a peptide containing an aldehyde-bearing formylglycine (fGly) residue according to embodiments of the present disclosure. Figure (panel A) shows a series of RP HPLC traces including the starting materials (fGly 13 mer and Compound 80) followed by the reaction mixtures at different time points (1, 2, 4, and 5 hours). Figure (panel 2B) is a schematic drawing of an aldehyde-tagged antibody reacting with the functionalized compound.

Results of the conjugation reaction are shown in FIG. 2A. FIG. 2A shows a series of RP HPLC traces including the starting materials (fGly 13 mer and Compound 80) followed by the reaction mixtures at different time points (1, 2, 4, and 5 hours). The peak at 13 min indicates a single addition of the functionalized compound to the polypeptide. FIG. 2B is a schematic drawing of an aldehyde-tagged antibody reacting with the functionalized compound. As shown in FIG. 2B, a single functionalized compound is conjugated to each fGly residue in the aldehyde-tagged antibody.

Example 3

Stoichiometric Variation

The following reagents were combined and aliquots taken at 2 hours and 24 hours to monitor product formation at 215 nm by C18 RP HPLC:

10 mM $H_2N$-GPSVFPL(fGly)TPSR—OH (SEQ ID NO:3) in MilliQ water (8 µL);
1×DPBS (62 µL); and
20 mM Pz-$CO_2H$ in MilliQ water (2 µL).

Figure 3:
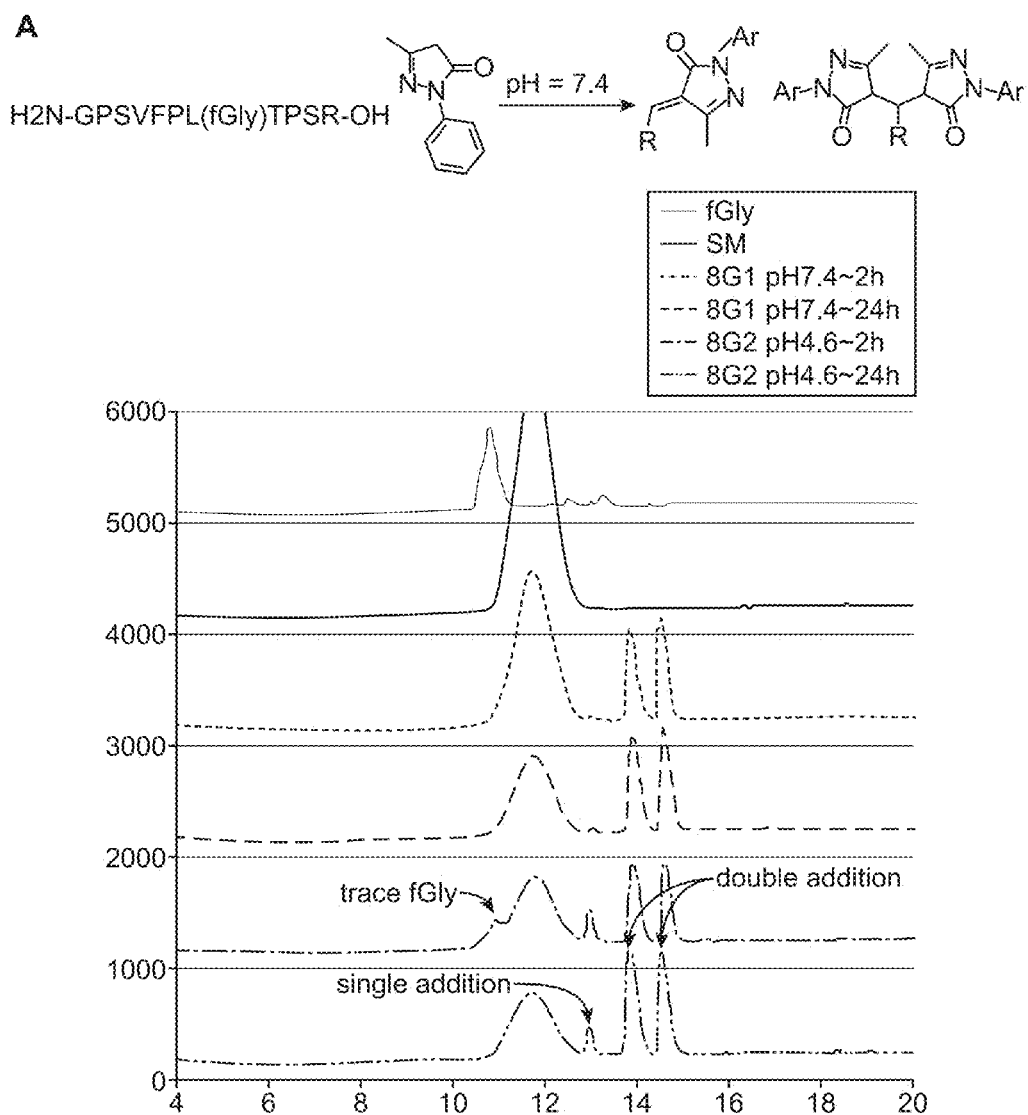
FIG. 3 shows the reactivity of a functionalized compound to a peptide containing an aldehyde-bearing formylglycine (fGly) residue at 2 different pHs according to embodiments of the present disclosure. Figure (panel A) shows a series of RP HPLC traces including the starting materials (fGly 13 mer and starting material coupling compound (SM)) followed by the reaction mixtures at different time points (2 and 24 hours at pH 7.4 and pH 4.6). Figure (panel B) shows the double addition of SM to a 6 mer fGly containing peptide. Figure (panel C) is a schematic drawing of an aldehyde-tagged antibody reacting with the functionalized compound.

Results of the conjugation reaction are shown in FIG. 3A. FIG. 3A shows a series of RP HPLC traces including the starting materials (fGly 13 mer and starting material coupling compound (SM)) followed by the reaction mixtures at different time points (2 and 24 hours at pH 7.4 and pH 4.6). The two peaks at about 14 min indicate a double addition of compound SM to the polypeptide. FIG. 3B shows the conjugation of the coupling compound (SM) to a fGly 6 mer peptide using the same reaction conditions above. The resulting conjugation was monitored by LC-MS/MS and the double addition product was identified as the only product from the reaction. FIG. 3C is a schematic drawing of an aldehyde-tagged antibody reacting with compound SM. As shown in FIG. 3C, two compounds are conjugated to each fGly residue in the aldehyde-tagged antibody.

Example 4

Conjugation of C-Terminally Aldehyde-Tagged Anti-HER2 Antibody with Ligation Reagent In a 1 mL Eppendorf tube, 20 µL of a 6.8 µM solution of an anti-HER2 in 1×DPBS buffer was added to 20 µL of a 0.68 mM solution of Pz in 0.5% MeCN in 1×DPBS. This solution was maintained at 37° C. for 16 h and then reduced, alkylated, and digested with trypsin. Product formation was analyzed by liquid chromatography multiple reaction monitoring mass spectrometry (LC-MRM-MS).

Figure 4A:
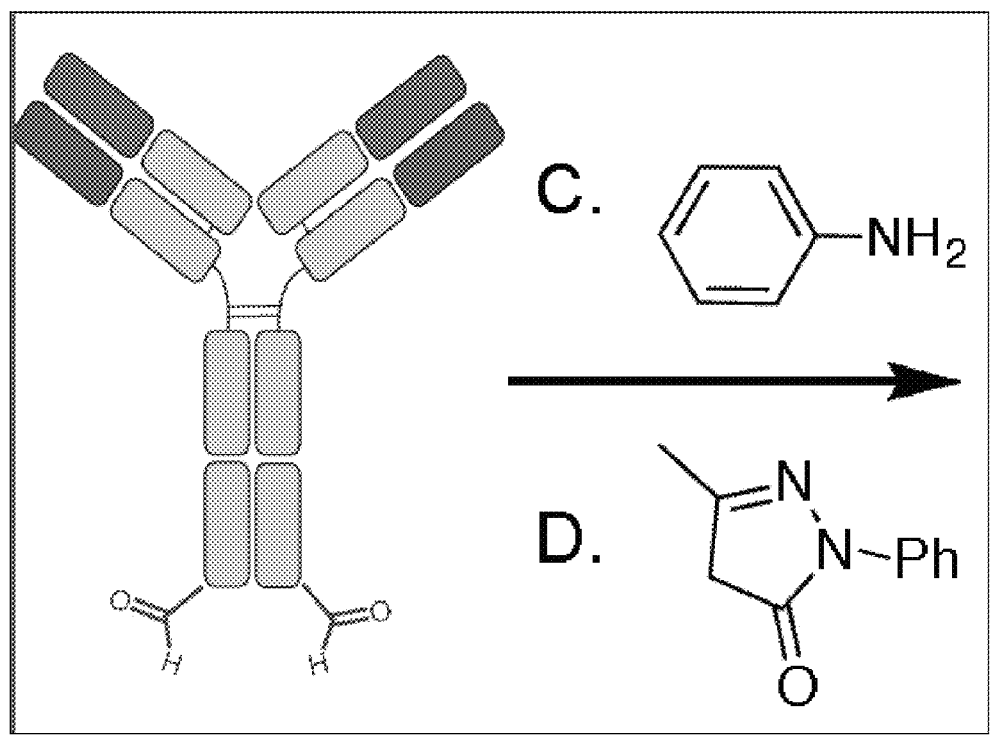
FIGS. 4A and 4B show conjugations to an aldehyde-tagged antibody according to embodiments of the present disclosure.
Figure 4B:
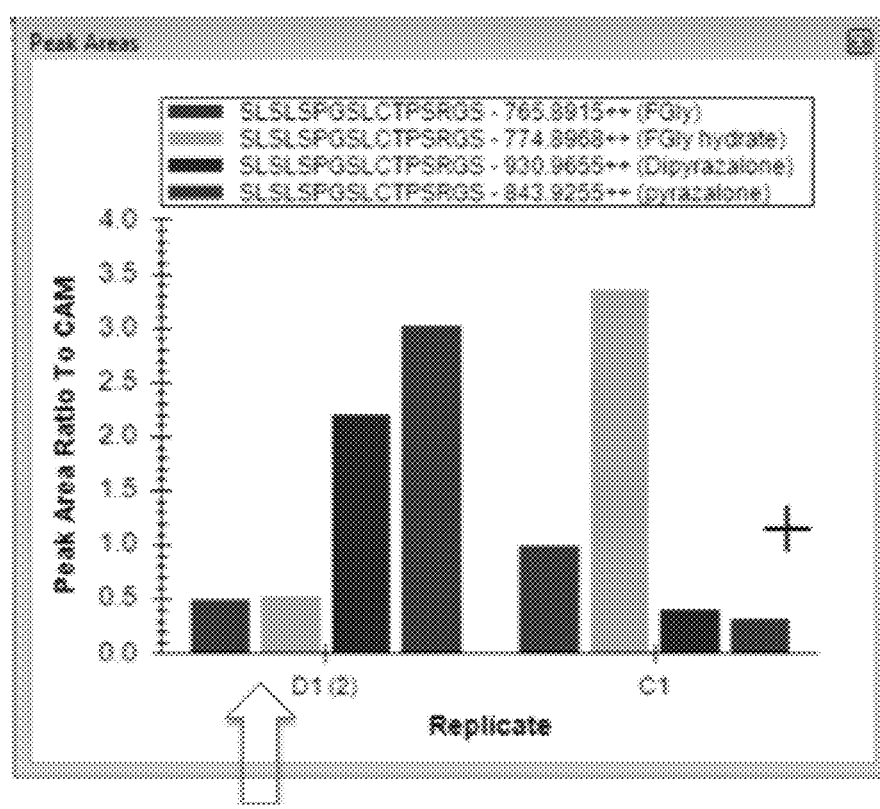

Results are shown in FIG. 4. FIG. 4A shows a schematic showing conjugations carried out with either compound C or compound D. FIG. 4B shows the ratio of starting material and product formation was analyzed by liquid chromatography multiple reaction monitoring mass spectrometry (LC-MRM-MS). The disappearance of starting material using compound D is highlighted by the arrow. Compound C did not significantly react with the antibody under the same reaction conditions.

Example 5

Conjugation of Modified-AF594 to C-Terminally Aldehyde Tagged HER2 with Ligation Reagent The following Pz-AF594 equivalents were added to 1.35 µM anti-HER2: 1, 2, 5, 10, 100, or 200 Pz-AF594 and incubated for 2 hr at 37° C. The samples were then electrophoretically separated SDS-PAGE gel. AF594 fluorescence was detected using an ImageQuant LAS 4000 and total protein was detected using Coomassie stain.

Figure 5:
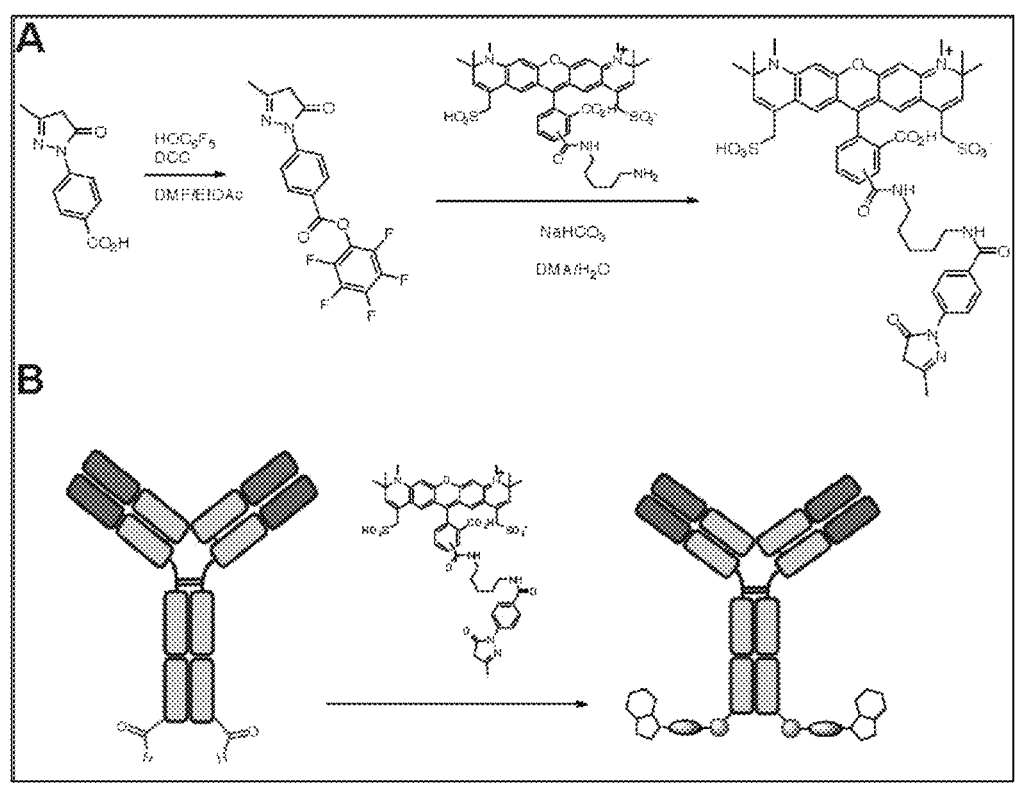
FIG. 5 shows the conjugation of a detectable label to an antibody according to embodiments of the present disclosure. Figure (panel A) shows a reaction scheme for the synthesis of the functionalized detectable label. Figure (panel B) shows a schematic of the conjugation reaction of the functionalized detectable label to the antibody. Figure (panel C) shows an image of an SDS-PAGE gel showing the results of the reaction. SDS-PAGE was used to separate the labeled heavy chain from light chain. The conjugation of the detectable label was determined by fluorescence imaging.

FIG. 5A shows a reaction scheme for the synthesis of the functionalized detectable label. FIG. 5B shows a schematic of the conjugation reaction of the functionalized detectable label to the antibody. Results are shown in FIG. 5C. FIG. 5C shows an image of an SDS-PAGE gel showing the results of the reaction. SDS-PAGE was used to separate the labeled heavy chain from light chain. The conjugation of the detectable label was determined by fluorescence imaging.

Example 6

Stability of Antibody-Detectable Label Conjugate

Figure 6:
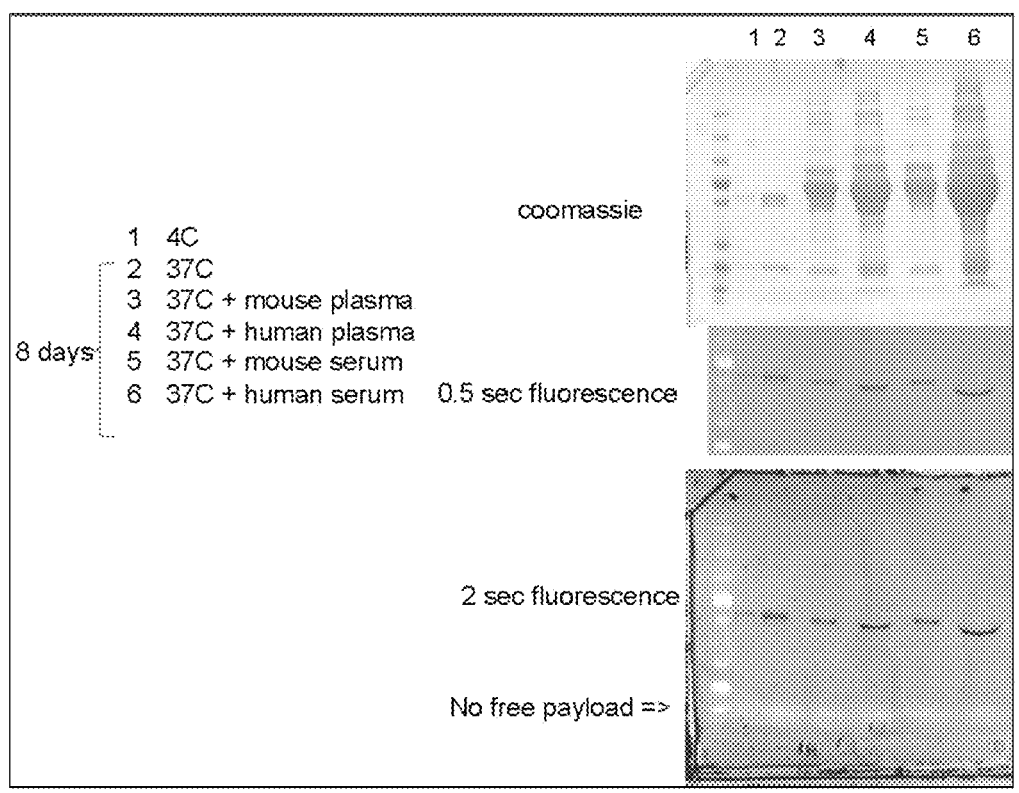
FIG. 6 shows the stability of the antibody-detectable label conjugate. There is no disappearance of conjugate after 8 days at 37° C. in plasma and serum.

Pz-AF594 (151 equivalents) was reacted with 6.6 µM anti-HER2 for 16 hr at 37° C. The unreacted Pz-AF594 was removed from the reaction mixture by size exclusion chromatography. The resulting antibody-fluorophore conjugate was incubated at 4° C. or 37° C. in either plasma or serum (both human and mouse) for 8 days. SDS-PAGE was used to analyze the conjugate. The presence of conjugate was determined by fluorescence imaging at either a 0.5 second exposure or a 2 second exposure. No free dye was observed in either case and the conjugate had not decomposed (see FIG. 6).

Example 7

Pz-Ph-2PEG-Maytansine

Experiments were performed to produce a conjugate comprising a maytansine and a pyrazalinone (Pz) coupling moiety according to Scheme 6 below.

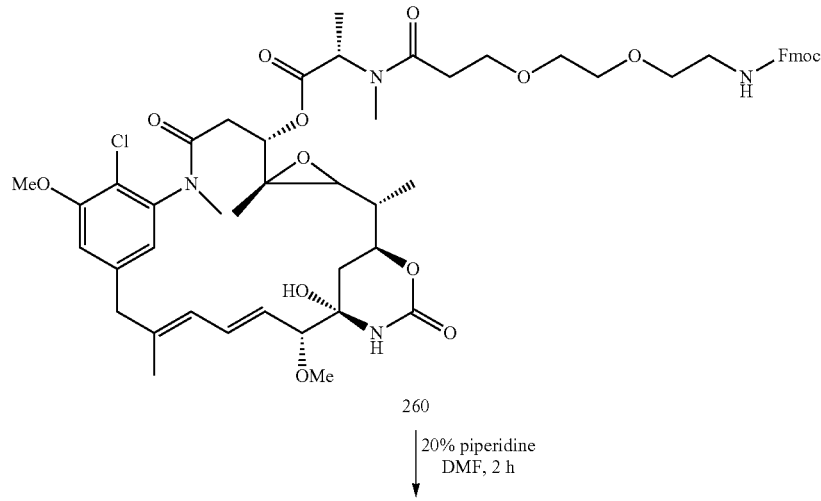

Scheme 6

260

20% piperidine
DMF, 2 h

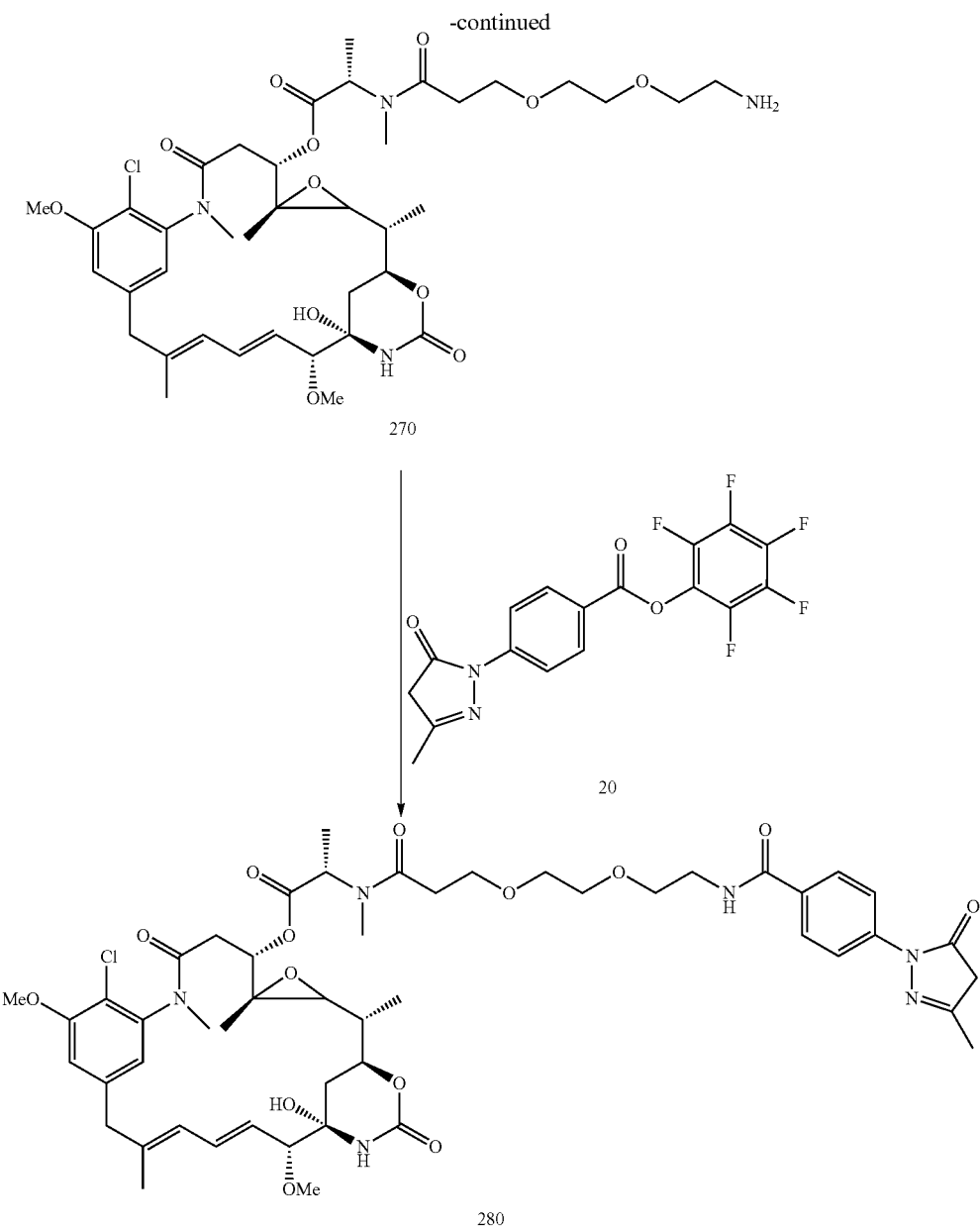

Compound 270 (amino-2PEG-Maytansine) was synthesized from Compound 260 as follows. To a solution of 28.2 μmol Compound 260 (Fmoc-N-2PEG-Maytansine) in 100 μL MA was added 564 μmol piperidine and stirred for 2 h. The crude reaction was purified by flash chromatography (C18) using a step gradient of 1% MeCN:water (10 column volumes) followed by 50% MeCN:water (10 column volumes) to give the product Compound 270 in 22% yield. LRMS (ESI) calculated for $C_{39}H_{57}ClN_4O_{12}$ [M+H]$^+$: 809.3. found 809.3.

Compound 280 (Pz-Ph-2PEG-Maytansine) was synthesized from Compound 270 as follows. An oven-dried 1 mL vial was charged with 6.06 μmol Compound 270 in 120 μL followed by 6.06 μmol Pz-PFP (Compound 20, perfluorophenyl 4-(3-methyl-5-oxo-4,5-dihydro-1H-pyrazol-1-yl) benzoate) in 80 μL and 15.4 μmol NaHCO$_3$ in 21 μL water. The reaction was stirred for 4 h then purified by Reverse Phase HPLC to afford 0.9 mg Compound 280. LRMS (ESI) calculated for $C_{50}H_{65}ClN_6O_{14}$ [M+Na]$^+$: 1031.4. found 1031.5.

Figure 7:
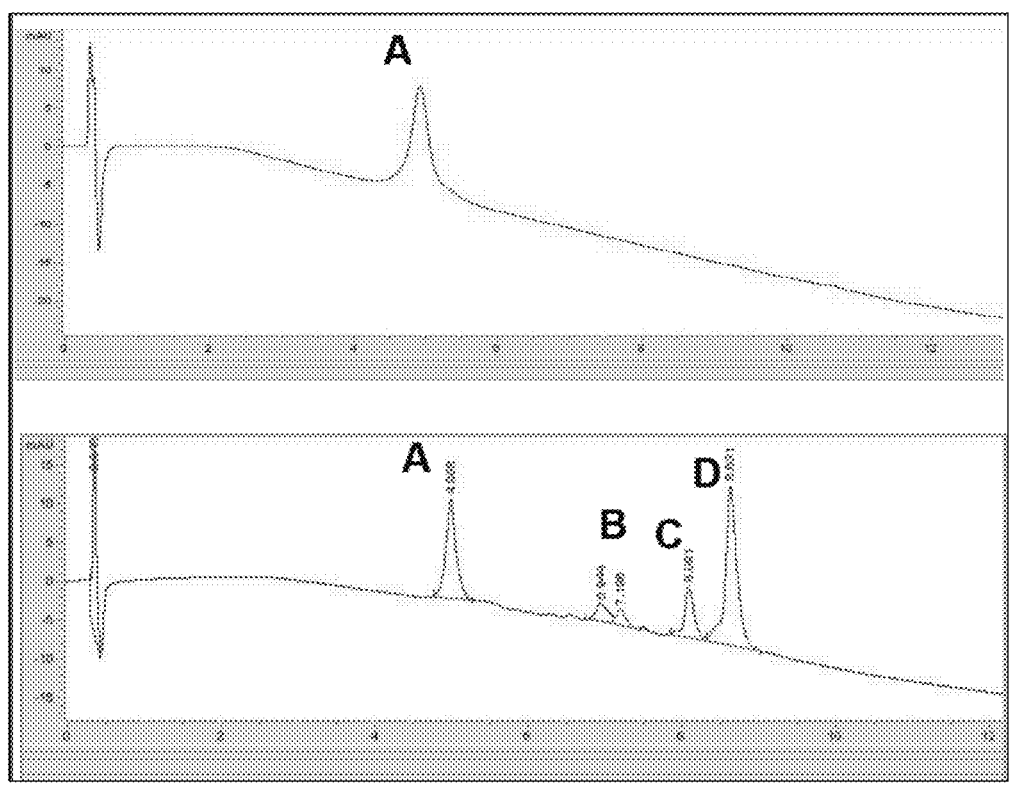
FIG. 7 shows a hydrophobic interaction column (HIC) trace of aldehyde-tagged antibody (A) (FIG. 7, top panel) according to embodiments of the present disclosure. Aldehyde-tagged antibody (A) was reacted with Pz-2PEG-Maytansine in PBS at pH 7, 37° C., with 2.5% DMA. The reaction mixture was analyzed by hydrophobic interaction column (HIC) after 24 hours (FIG. 7, bottom panel). Both the mono-conjugate (B) and di-conjugate (D) protein conjugate were observed.

Aldehyde-tagged antibody (A) was reacted with Pz-Ph-2PEG-Maytansine in PBS at pH 7, 37° C., with 2.5% DMA. The reaction mixture was analyzed by hydrophobic interaction column (HIC) after 24 hours (FIG. 7, bottom panel). Both the mono-conjugate (B) and di-conjugate (D) protein conjugate were observed. FIG. 7 also shows a hydrophobic interaction column (HIC) trace of aldehyde-tagged antibody (A) (FIG. 7, top panel).

Example 8

General Synthetic Routes

Pyrazalinone-cargo (Pz-cargo) constructs of the present disclosure were synthesized according to the following general synthetic routes. For example, a β-ketoester was synthesized from a carboxylic acid derivative, and the desired Pz-cargo construct was subsequently synthesized from the resulting β-ketoester. Examples of the general synthetic routes are shown in Scheme 7 below.

Scheme 7

General Route to β-ketoesters

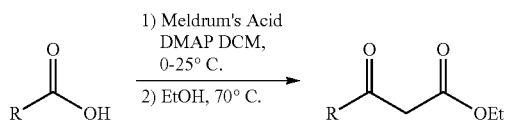

General Route to Pz-cargo Constructs

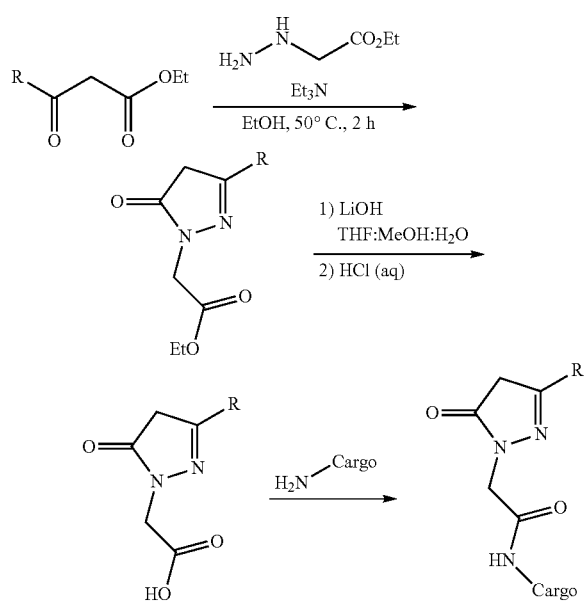

Nucleophilic Trap-Pyrazalinone Coupling Moieties

Nucleophilic trap-pyrazalinone coupling moieties were synthesized according to the reaction schemes shown in Examples 9-14 below. Nucleophilic trap-pyrazainone coupling moieties included thio-Pz, nitro-Pz, amino-Pz, phenol-Pz, alcohol-Pz and furan-Pz coupling moieties, as shown in more detail in Examples 9-14 below.

Example 9

Thio-Pz Coupling Moiety

A thio-Pz nucleophilic trap coupling moiety was synthesized according to Scheme 8 below.

Scheme 8

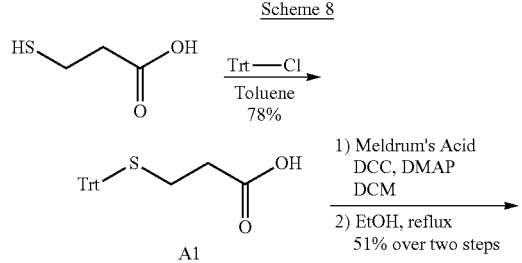

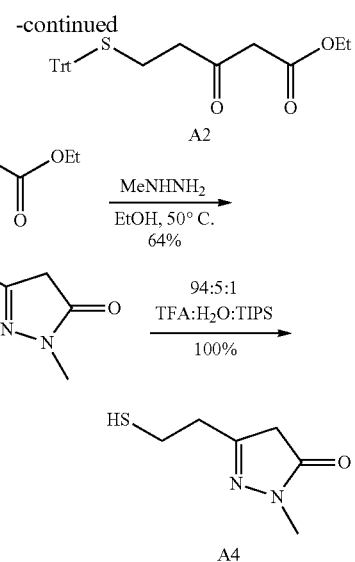

3-(Tritylthio)propranoic acid (A1)—A two-neck 100 mL round bottom flask equipped with a dry tube charged with trityl-chloride (1.927 g, 6.9 mmol) and 6 mL anhydrous toluene. Following dropwise addition of 3-thioproprionic acid (720 uL, 8.3 mmol) the heterogeneous mixture was stirred for 16 h to produce a white precipitate. The precipitate was collected via filtration, washed with cold toluene, and dried under vacuum to produce 1.875 g of the desired product. The product was used with out further purification.

$^1$H NMR (400 MHz, DMSO) 12.24 (s, 1H), 7.25 (m, 15H), 2.28 (t, J=6.8 Hz, 2H), 2.17 (t, J=6.8 Hz, 2H).

Ethyl 3-oxo-5-(tritylthio)pentanoate (A2)—A solution of 3-(tritylthio)propranoic acid (287 mg, 0.824 mmol), Meldrum's acid (118.7 mg, 0.824 mmol), and 4-dimethylaminopyridine in 1.6 mL anhydrous DCM was cooled to 0° C. To this solution was added 0.7 mL N,N'-dicyclohexylcarbodiimide (100 mg, 0.819 mmol) in anhydrous DCM. The reaction was maintained at 0° C. for 30 min, then allowed to warm to room temperature and maintained for 5 h. The reaction was then diluted with 10 mL DCM and transferred to a separatory funnel. The organic phase was washed with 3×10 mL 1M HCl (aq), 3×10 mL brine. The organic phase was collected then dried over MgSO$_4$, filtered and evaporated under reduced pressure. The resultant oil was then dissolved in 10 mL anhydrous ethanol and refluxed for 16 h. The crude reaction was evaporated under reduced pressure and loaded onto a 10 g Biotage Silica Gel Samplet, which was chromatographed using a 33%-100% Hexane:DCM gradient to produce 174.1 mg of the desired product.

$^1$H NMR (400 MHz, CDCl$_3$) 7.43 (app d, J=9.2 Hz, 6H), 7.31 (app t, J=7.2 Hz, 6H), 7.22 (app t, J=7.2 Hz, 3H), 4.17 (t, J=7.2 Hz, 2H), 3.30 (s, 2H), 2.45 (m, 4H), 1.28 (t, J=7.2 Hz, 3H). LRMS (ESI) calcd for C$_{26}$H$_{26}$O$_3$S [M+Na]$^+$: 441. found 441.

1-Methyl-3-(2-(tritylthio)ethyl)-1H-pyrazol-5(4H)-one (A3)—Methylhydrazine (10.8 μL, 0.205 mmol), ethyl 3-oxo-5-(tritylthio)pentanoate (85.6 mg, 0.205 mmol) and 1 mL anhydrous ethanol was heated at 50° C. for 16 h. The crude reaction was chromatographed using a 50-100% hexane:ethyl acetate gradient to produce 52.3 mg of the desired product in 64% yield.

¹H NMR (400 MHz, CDCl₃) 7.44 (app d, J=8 Hz, 6H), 7.31 (m, 6H), 7.24 (m, 3H), 3.26 (s, 2H), 2.97 (s, 2H), 2.43 (t, J=6.4 Hz 2H), 1.28 (t, J=6.4 Hz, 2H).

3-(2-Mercaptoethyl)-1-methyl-1H-pyrazol-5(4H)-one (A4)—To a solution of 1-methyl-3-(2-(tritylthio)ethyl)-1H-pyrazol-5(4H)-one (46.3 mg, 0.116 mmol) in 4 mL DCM was added 0.1 mL water, 0.1 mL triisopropylsilane, and 0.8 mL trifluoroacetic acid. The reaction was stirred 1 h then concentrated in vacuo. The crude mixture was chromatographed using 0-10% methanol:DCM to produce the 20.2 mg of the desired product.

LRMS (ESI) calcd for C6H₁₀N₂OS [M+H]⁺: 159. found 159.

Compound A8 (thio-Pz-2PEG-Maytansine) was synthesized from Compound A2 and Compound 270 (amino-2PEG-Maytansine) according to Scheme 9 below.

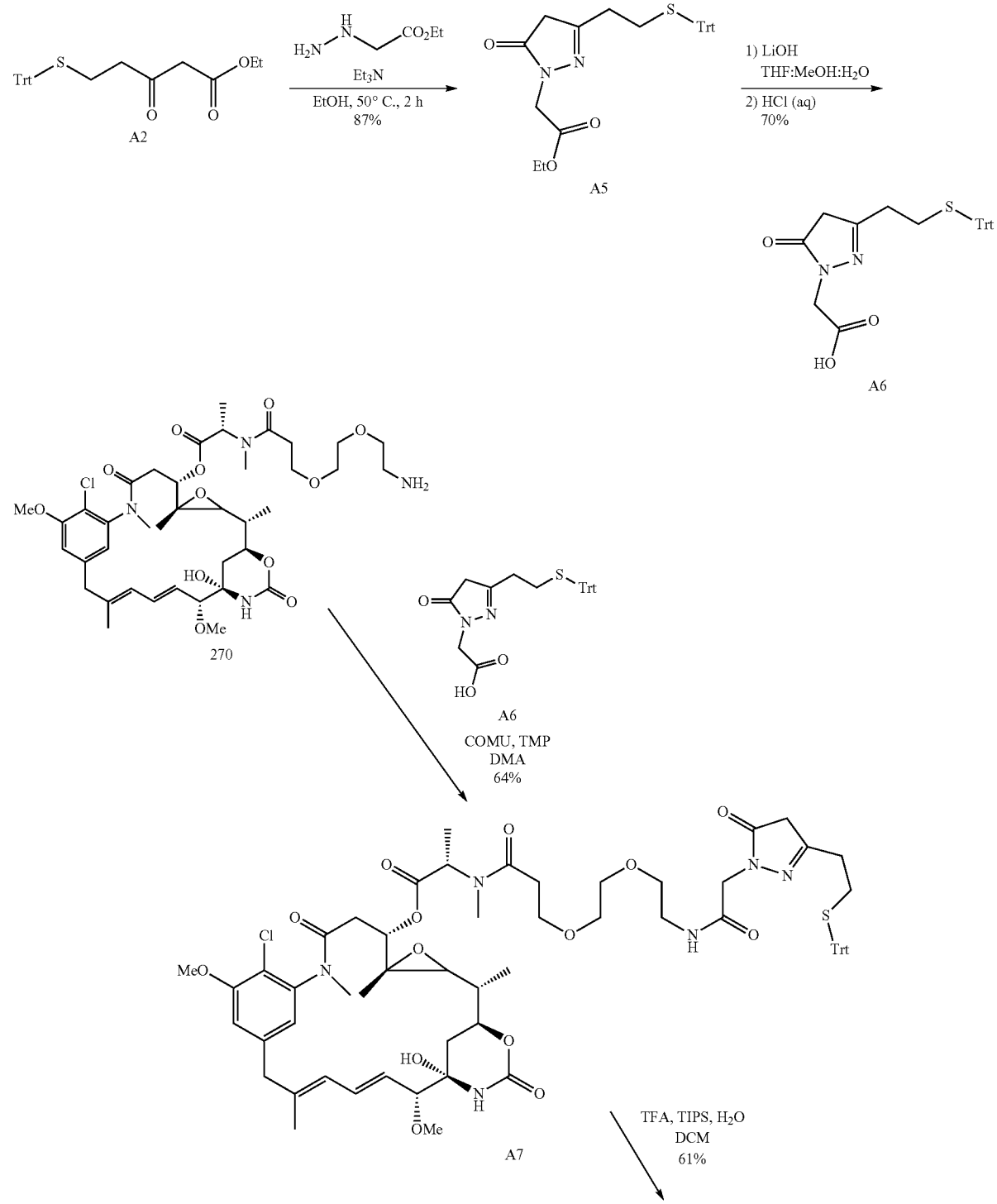

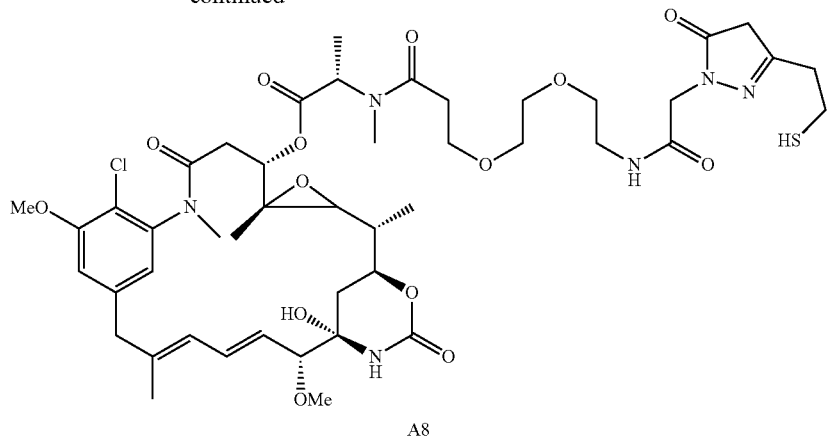

A8

Ethyl 2-(5-oxo-3-(2-(tritylthio)ethyl)-4,5-dihydro-1H-pyrazol-1-yl)acetate (A5)—A solution of ethyl 3-oxo-5-(tritylthio)pentanoate (A2) (499 mg, 1.24 mmol), ethyl 2-hydrazinylacetate (191 mg, 1.23 mmol), triethylamine (17 μL, 0.124 mmol) in 10 mL ethanol was maintained at 50° C. for 2 h. The crude reaction was concentrated in vacuo and chromatographed on silica gel using a 33-60% hexane:ethyl acetate gradient to produce 320.6 mg of the desired product.

$^1$H NMR (400 MHz, CDCl$_3$) 7.44 (app d, J=8 Hz, 6H), 7.31 (m, 6H), 7.24 (m, 3H), 4.40 (s, 2H), 4.21 (q, J=7.2 Hz, 2H), 3.03 (s, 2H), 2.44 (t, J=6.8 Hz, 2H), 2.37 (t, J=6.8 Hz 2H), 1.28 (t, J=7.2 Hz, 2H).

2-(5-Oxo-3-(2-(tritylthio)ethyl)-4,5-dihydro-1H-pyrazol-1-yl)acetic acid (A6) To a solution of ethyl 2-(5-oxo-3-(2-(tritylthio)ethyl)-4,5-dihydro-1H-pyrazol-1-yl)acetate (A5) (97.8 mg, 0.207 mmol) in 1 mL of 2:3:1 THF:MeOH:water was added 10.7 mg of lithium hydroxide. The reaction was maintained for 2 h then partitioned between 40 mL water and 40 mL ethyl ether. The aqueous layer was acidified to pH 2 and washed 3×60 mL with DCM. The organic phases were combined, dried over MgSO$_4$, filtered, and concentrated in vacuo to yield 65.5 mg of the desired product, which was used with out further purification.

$^1$H NMR (400 MHz, DMSO) 7.33 (m, 12H), 7.25 (m, 3H), 5.01 (s, 1H), 4.47 (s, 2H), 2.35 (t, J=7.2 Hz, 2H), 2.28 (t, J=7.2 Hz 2H).

Trt-thioPz-2PEG-Maytansine (A7)—To a 0° C. solution of amino-2PEG-Maytansine (270) (18.5 mg, 0.0229 mmol), 2-(5-oxo-3-(2-(tritylthio)ethyl)-4,5-dihydro-1H-pyrazol-1-yl)acetic acid (A6) (6.8 mg, 0.0153 mmol), 2,4,6-trimethylpyridine (0.0153 mmol) in 100 μL DMF was added 6.8 mg COMU ((1-cyano-2-ethoxy-2-oxoethylidenaminooxy) dimethylamino-morpholino-carbenium). The reaction was maintained at 0° C. for 30 min then warmed to room temperature over 30 min. The resulting reaction mixture was diluted with 10 mL EtOAc then transferred to a separatory funnel. The organic phase was washed 3×10 mL 1M HCl, 3×10 mL saturated NaHCO$_3$, and 3×10 mL brine. The organic phase was dried over MgSO$_4$, filtered and concentrated in vacuo. The crude reaction was chromatographed on silica gel using a 5-12% methanol:DCM gradient to yield 8.8 mg of the desired product.

LRMS (ESI) calcd for C$_{65}$H$_{79}$ClN$_6$O$_{14}$S [M+Na]$^+$: 1257.5. found 1257.5.

Thio-Pz-2PEG-Maytansine (A8)—Trt-thioPz-2PEG-Maytansine (A7) (8.8 mg) was dissolved in 400 μL DCM and cooled to 0° C. To this solution was added 10 μL triisopropylsilane, 10 μL water, and 80 μL trifluoroacetic acid. The reaction was maintained at 0° C. for 1 h. The crude reaction was purified by reverse phase chromatography using a 5-67% MeCN:water gradient to yield 4 mg of the desired product.

LRMS (ESI) calcd for C$_{46}$H$_{65}$ClN$_6$O$_{14}$S [M−H]$^-$: 991.4. found 991.1.

Example 10

Nitro-Pz Coupling Moiety

A nitro-Pz nucleophilic trap coupling moiety was synthesized according to Scheme 10 below.

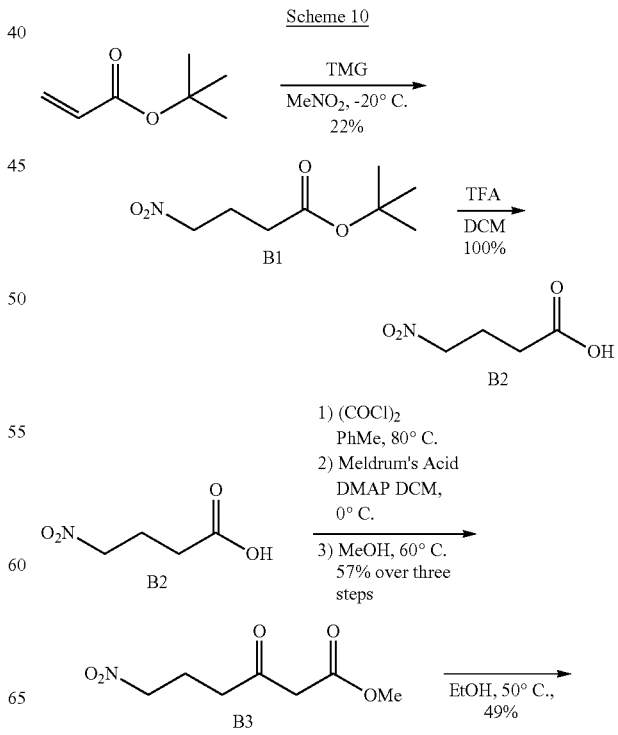

Scheme 10

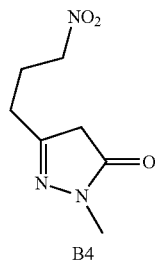

Tert-butyl 4-nitrobutanoate (B1)—A solution of tert-butyl acrylate (4.4 mL, 30 mmol) in 50 mL nitromethane was cooled to −20° C. To this solution was added 0.6 mL of 1,1,3,3-tetramethylguanidine (TMG) and allowed to stir at −20° C. for 3 h. The reaction was diluted with 175 mL DCM, transferred to a separatory funnel and washed 5×100 mL brine. The organic phase was dried over MgSO$_4$, filtered and concentrated in vacuo. The crude product was purified by vacuum distillation (190 mtorr, 65° C.) to yield 1.27 g of the desired product.

$^1$H NMR (400 MHz, CDCl$_3$) 4.84 (t, J=6.8 Hz, 2H), 2.41 (t, J=6.8 Hz, 2H), 2.29 (tt, J=6.8, 6.8 Hz, 2H), 1.47 (s, 9H).

4-Nitrobutanoic acid (B2)—To a solution of tert-butyl 4-nitrobutanoate (B1) in 2 mL DCM was added 1 mL trifluoroacetic acid and allowed to stir for 3 h. Toluene (4 mL) was added to the reaction mixture, which was then concentrated in vacuo. This was repeated twice.

$^1$H NMR (400 MHz, CDCl$_3$) 4.52 (t, J=6.8 Hz, 2H), 2.57 (t, J=6.8 Hz, 2H), 2.33 (tt, J=6.8, 6.8 Hz, 2H).

Methyl 6-nitro-3-oxohexanoate (B3)—A solution of 4-nitrobutanoic acid (233 mg, 1.75 mmol) (B2), 2254, oxalyl chloride and 5 mL toluene was heated at 80° C. for 19 h and then concentrated in vacuo. The crude reaction mixture was azeotroped 3×5 mL toluene. The resultant oil was dissolved in 1.6 mL anhydrous DCM and added dropwise over 20 min to a 0° C. solution of Meldrum's acid (199 mg) and 4-dimethylaminopyridine (323 mg). Upon addition, the solution was allowed to warm to room temperature and maintained for 90 min. The reaction mixture was diluted with 60 mL DCM and washed 3×40 mL 1M HCl and 2×40 mL brine. The organic phase was dried over MgSO$_4$, filtered and concentrated in vacuo. The resulting oil was then dissolved in 10 mL methanol and heated at 65° C. for 16 h. The reaction mixture was then concentrated in vacuo and chromatographed on silica gel using a 33-100% hexane: ethyl acetate gradient to yield 189 mg of the desired product.

$^1$H NMR (400 MHz, CDCl$_3$) 4.46 (t, J=6.8 Hz, 2H), 3.76 (s, 3H), 3.49 (s, 2H), 2.76 (t, J=6.8 Hz, 2H), 2.32 (tt, J=6.8, 6.8 Hz, 2H).

1-Methyl-3-(3-nitropropyl)-1H-pyrazol-5(4H)-one (B4)—A solution of 189 mg methyl 6-nitro-3-oxohexanoate (B3) and 57.8 μL methylhydrazine in 3 mL ethanol was stirred at 50° C. for 5 h. The reaction was concentrated in vacuo and choromatographed on silica gel using a 0-100% ethyl acetate:acetonitrile gradient to yield 91 mg of the desired product.

$^1$H NMR (400 MHz, CDCl$_3$) 4.54 (t, J=6.8 Hz, 2H), 3.62 (s, 3H), 3.21 (s, 2H), 2.54 (t, J=6.8 Hz, 2H), 2.38 (tt, J=6.8, 6.8 Hz, 2H). LRMS (ESI) calcd for C$_7$H$_{11}$N$_3$O$_3$ [M+H]$^+$: 186. found 186.

Example 11

Amino-Pz Coupling Moiety

An amino-Pz nucleophilic trap coupling moiety was synthesized according to Scheme 11 below.

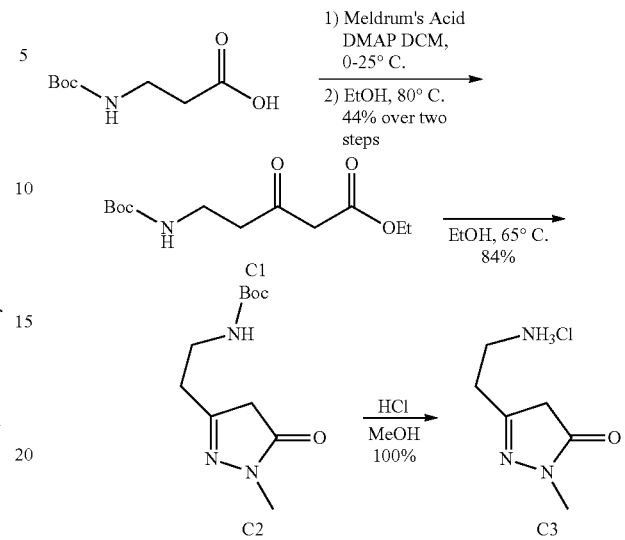

Ethyl 5-((tert-butoxycarbonyl)amino)-3-oxopentanoate (C1)—A solution of N-Boc-aminoproprionic acid (480 mg, 2.54 mmol), Meldrum's acid (2.54 mmol), 4-dimethylaminopyridine (DMAP) (2.79 mmol) in 5 mL anhydrous DCM was cooled to 0° C. To this solution was added N,N'-dicyclohexylcarbodiimide (2.79 mmol) in 2 mL anhydrous DCM. The solution was maintained at 0° C. for 3 h, diluted with 40 mL DCM and transferred to a separatory funnel. The organic phase was washed 2×15 mL 1M HCl, 2×15 mL brine, dried over MgSO$_4$, filtered and concentrated in vacuo. The crude reaction was then dissolved in 7 mL ethanol and heated at 80° C. for 16 h. The reaction mixture was concentrated in vacuo and then chromatographed on silica gel using a 0-90% ethyl acetate:hexanes gradient to yield 287.5 mg of the desired product.

$^1$H NMR (400 MHz, CDCl$_3$) 4.99 (bs, 1H), 4.22 (q, J=7.2 Hz, 2H), 3.46 (s, 2H), 3.39 (app q, J=6 Hz, 2H), 2.79 (t, J=6 Hz, 2H), 1.44 (s, 9H), 1.30 (t, J=7.2 Hz, 3H).

Tert-butyl (2-(1-methyl-5-oxo-4,5-dihydro-1H-pyrazol-3-yl)ethyl)carbamate (C2)—A solution of 287.5 mg of ethyl 5-((tert-butoxycarbonyl)amino)-3-oxopentanoate (C1) and 58.3 μL of methylhydrazine in 1 mL ethanol was heated at 65° C. for 5 h. The reaction was concentrated in vacuo and chromatographed on silica gel using a 0-15% methanol: DCM gradient to yield 223.8 mg of the desired product.

$^1$H NMR (400 MHz, CDCl$_3$) 4.89 (bs, 1H), 3.44 (app q, J=6.4 Hz, 2H), 3.29 (s, 3H), 3.24 (s, 2H), 2.57 (t, J=6.4 Hz, 2H), 1.44 (s, 9H). LRMS (ESI) calcd for C$_{11}$H$_{19}$N$_3$O$_3$ [M+H]$^+$: 242. found 242.

3-(2-aminoethyl)-1-methyl-1H-pyrazol-5(4H)-one.hydrogen chloride (C3)—To a solution of 77.7 mg tert-butyl (2-(1-methyl-5-oxo-4,5-dihydro-1H-pyrazol-3-yl)ethyl)carbamate (C2) in 1 mL methanol was added 0.8 mL 3M methanolic HCl. The reaction was maintained for 18 h, afterwhich the reaction was concentrated in vacuo to yield 73.5 mg of the desired product as its HCl salt.

$^1$H NMR (400 MHz, d$_3$-MeOD) 3.77 (s, 3H), 3.32 (t, J=7.6 Hz, 2H), 3.10 (t, J=7.6 Hz, 2H). LRMS (ESI) calcd for C$_6$H$_{11}$N$_3$O [M+H]$^+$: 142. found 142.

Example 12

Phenol-Pz Coupling Moiety

A phenol-Pz nucleophilic trap coupling moiety was synthesized according to Scheme 12 below.

Scheme 12

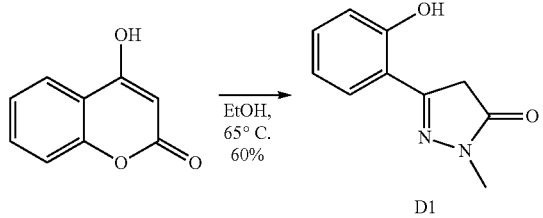

D1

3-(2-Hydroxyphenyl)-1-methyl-1H-pyrazol-5(4H)-one (D1)—Methylhydrazine (165 µL, 3.15 mmol) and 4-hydroxycoumarin (170 mg, 1.05 mmol) in 4 mL ethanol were heated to 70° C. for 48 h. After cooling to room temperature 200 µL acetic acid was added and the mixture was concentrated in vacuo. The crude reaction was purified by silica gel chromatography using a 0-100% DCM:ethyl acetate gradient to afford 120 mg of the desired product.

$^1$H NMR (400 MHz, CDCl$_3$) 10.01 (s, 1H) 7.35 (app td, J=8.4, 1.6 Hz, 1H), 7.19 (app dd, J=7.8, 1.6 Hz, 1H), 7.04 (app dd, J=8.2, 0.8 Hz, 1H), 6.95 (app td, J=8, 1.2 Hz, 1H), 3.71 (s, 2H), 3.43 (s, 3H). LRMS (ESI) calcd for C$_{10}$H$_{10}$N$_2$O$_2$ [M+H]$^+$: 191. found 191.

Example 13

Alcohol-Pz Coupling Moiety

An alcohol-Pz nucleophilic trap coupling moiety was synthesized according to Scheme 13 below.

Scheme 13

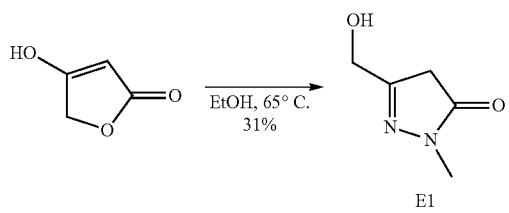

E1

3-(Hydroxymethyl)-1-methyl-1H-pyrazol-5(4H)-one (E1)—A solution of methylhydrazine (1.16 mmol) and tetronic acid (1.16 mmol, 115.5 mg) was heated to 75° C. in 1 mL ethanol for 20 h. Crystals formed upon cooling to room temperature. The crystals were collected, washed with cold ethanol, and dried to yield 45.5 mg of the desired product.

$^1$H NMR (400 MHz, CDCl$_3$) 4.83 (s, 2H), 4.58 (s, 1H), 3.17 (s, 3H). LRMS (ESI) calcd for C$_5$H$_8$N$_2$O$_2$ [M+H]$^+$: 129. found 129.

Example 14

Furan-Pz Coupling Moiety

A furan-Pz nucleophilic trap coupling moiety was synthesized according to Scheme 14 below.

Scheme 14

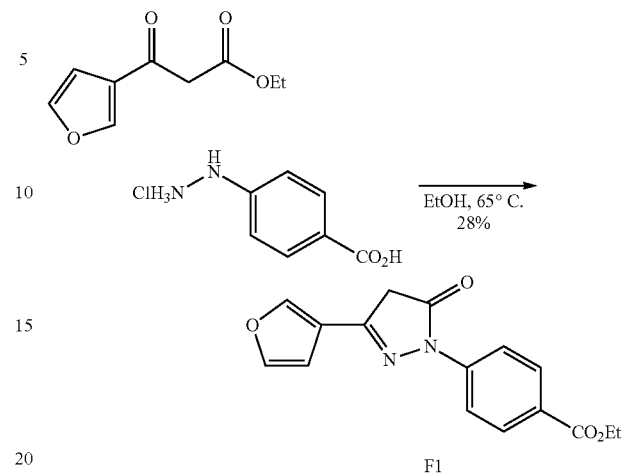

F1

Ethyl 4-(3-(furan-3-yl)-5-oxo-4,5-dihydro-1H-pyrazol-1-yl)benzoate (F1)—A solution of ethyl 3-(furan-3-yl)-3-oxo-propanoate (1.46 mmol) and 4-hydrazinobenzoic acid hydrogen chloride was refluxed in 5.5 mL ethanol for 20 h. Upon cooling to room temperature, the reaction mixture was concentrated in vacuo and purified via silica gel chromatography using a 3-60% ethyl acetate:hexane gradient to yield 122.4 mg of product.

$^1$H NMR (400 MHz, CDCl$_3$) 8.10 (m, 4H), 7.97 (dd, J=1.6, 0.8 Hz, 1H), 7.55 (dd, J=2.0, 1.6 Hz, 1H), 6.90 (dd, J=2.0, 0.8 Hz, 1H), 4.40 (q, J=7.2 Hz, 2H), 3.78 (s, 2H), 1.43 (t, J=7.2 Hz, 3H). LRMS (ESI) calcd for C$_{16}$H$_{14}$N$_2$O$_4$ [M+H]$^+$: 299. found 299.

Electrophilic Trap-Pyrazalinone Coupling Moieties

Electrophilic trap-pyrazalinone coupling moieties were synthesized according to the reaction schemes shown in Examples 15 and 16 below. Electrophilic trap-pyrazainone coupling moieties included EtO$_2$C-Pz and MeO$_2$C—CH$_2$-Pz coupling moieties, as shown in more detail in Examples 15-16 below.

Example 15

EtO$_2$C-Pz Coupling Moiety

An ethyl ester-pyrazalinone (EtO$_2$C-Pz) electrophilic trap coupling moiety was synthesized according to Scheme 15 below.

Scheme 15

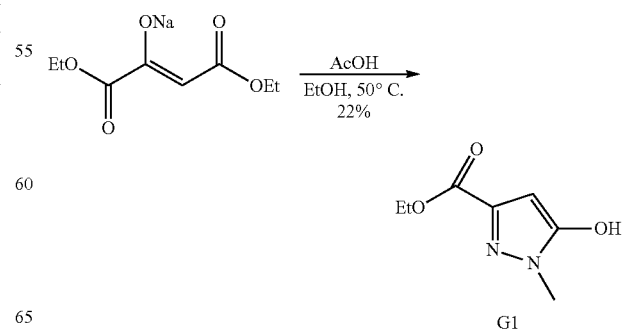

G1

Ethyl 1-methyl-5-oxo-4,5-dihydro-1H-pyrazole-3-carboxylate (G1)—A solution of 165 µL methylhydrazine, 660 mg sodium diethyl oxaloacetate, 179 µL acetic acid and 6 mL ethanol were heated at 50° C. for 20 h. The reaction was cooled to room temperature, concentrated in vacuo and purified by silica gel chromatography using 3% methanol:DCM to yield 120 mg of the desired product.

$^1$H NMR (400 MHz, CDCl$_3$) 5.97 (s, 1H), 4.34 (q, J=7.2 Hz, 2H), 3.72 (s, 3H), 1.32 (t, J=7.2 Hz, 3H). LRMS (ESI) calcd for C$_7$H$_{10}$N$_2$O$_3$ [M+H]$^+$: 171. found 171.

Example 16

MeO$_2$C—CH$_2$-Pz Coupling Moiety

A methyl acetate-pyrazalinone (MeO$_2$C—CH$_2$-Pz) electrophilic trap coupling moiety was synthesized according to Scheme 16 below.

Scheme 16

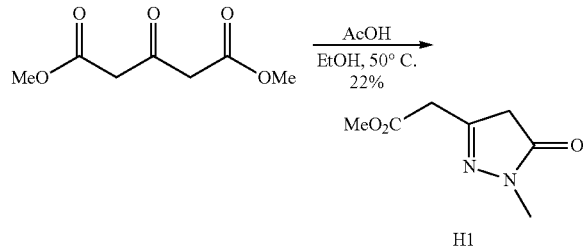

Methyl 2-(1-methyl-5-oxo-4,5-dihydro-1H-pyrazol-3-yl)acetate (H1)—A solution of 338 µL dimethyl hydrazine, 1.12 g dimethyl-1,3-acetonedicarboxylate in 12 mL ethanol was heated at 50° C. for 20 h. The reaction was cooled to room temperature, concentrated in vacuo and purified by silica gel chromatography using 5% methanol:DCM to yield 796 mg of the desired product.

$^1$H NMR (400 MHz, CDCl$_3$) 3.77 (s, 3H), 3.50 (s, 2H), 3.89 (s, 2H), 3.32 (s, 3H). LRMS (ESI) calcd for C$_7$H$_{10}$N$_2$O$_3$ [M+H]$^+$: 171. found 171.

Conjugation of Pyrazalinone Coupling Moieties to fGly-Containing Peptides

Experiments were performed to conjugate fGly-containing peptides to pyrazalinone coupling moieties described above according to embodiments of the present disclosure.

Example 17

Conjugation of FGly-Containing Peptide with Thio-Pz Coupling Moiety

The following reagents were combined and aliquots taken at 3 and 15 hours and the reaction monitored for product formation at 215 nm by C18 RP HPLC:
  70 µL MilliQ water,
  10 µL 10×DPBS,
  10 µL 50 mM Compound A4 in DMA,
  10 µL 1 mM H$_2$N-GPSVFPL(fGly)TPSR—OH (SEQ ID NO:3).

Products (I2, I3, and I4) were isolated via HPLC and analyzed on a 4000 QTRAP using an LC-MS/MS method. Precursor and product ions indicated the formation of the desired product.

Figure 8A:
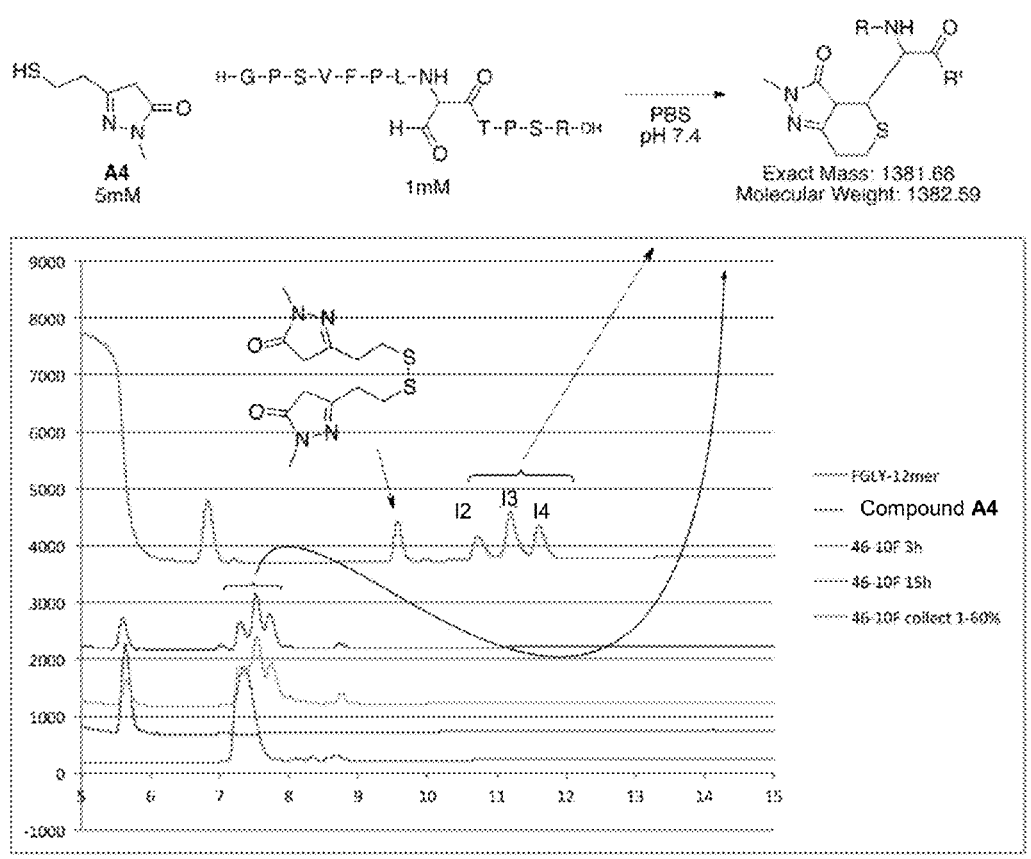
FIG. 8A shows a series of RP HPLC traces including the starting materials (fGly 12 mer and Compound A4) followed by the reaction mixtures at different time points (3 and 15 hours).
Figure 8B:
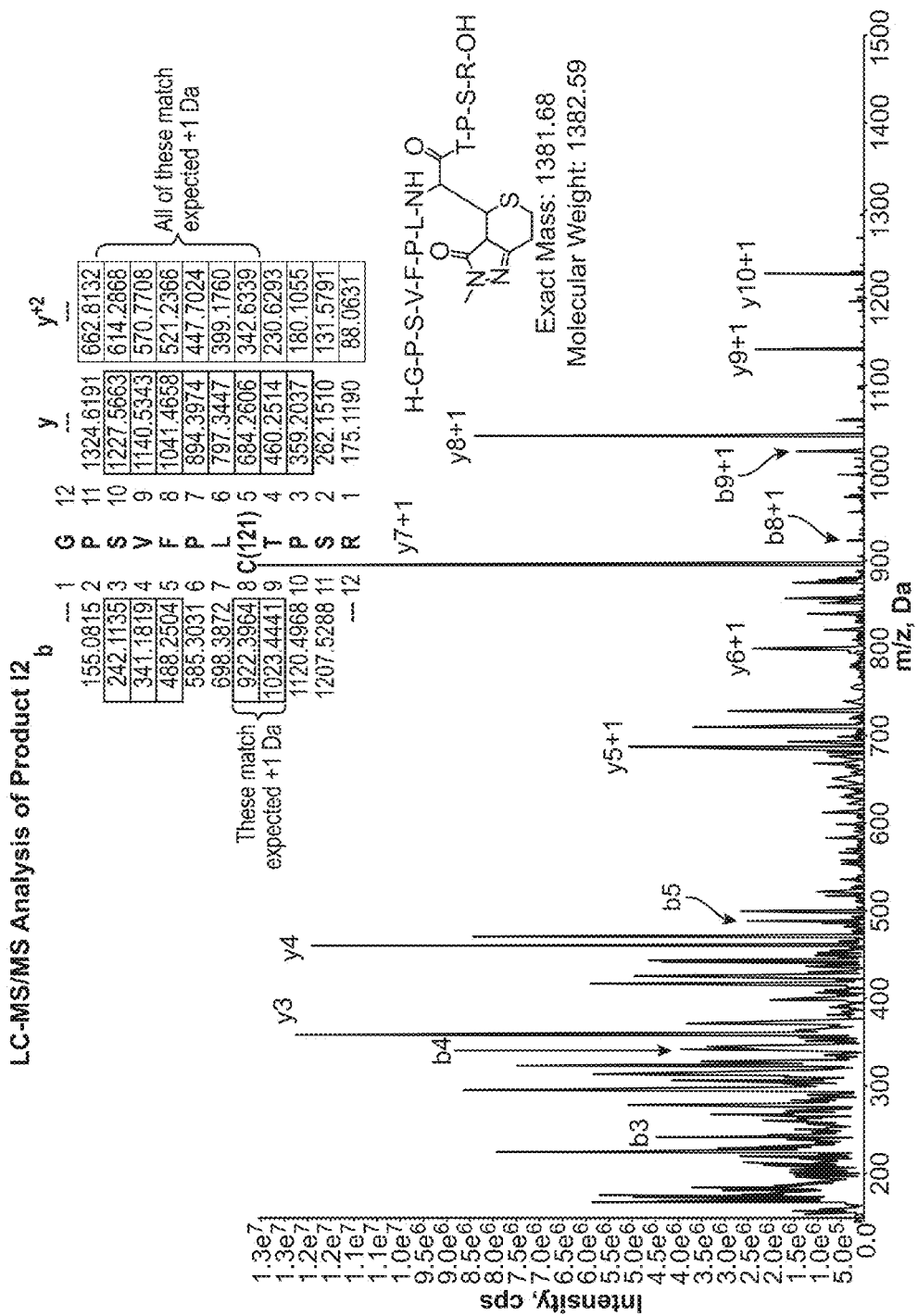
FIG. 8B is a LC-MS/MS analysis of Product I2 from the conjugation reaction.
Figure 8C:
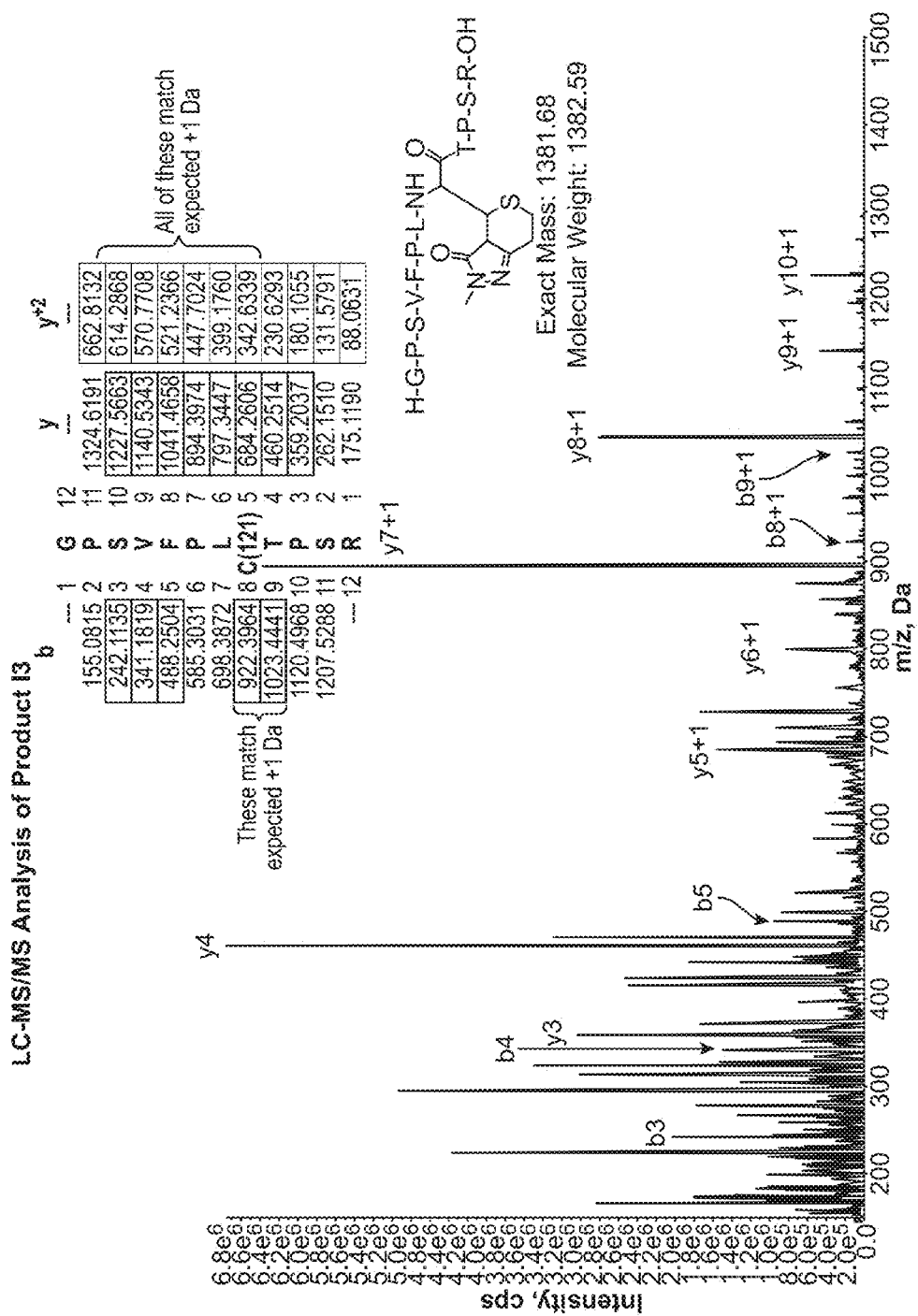
FIG. 8C is a LC-MS/MS analysis of Product I3 from the conjugation reaction.
Figure 8D:
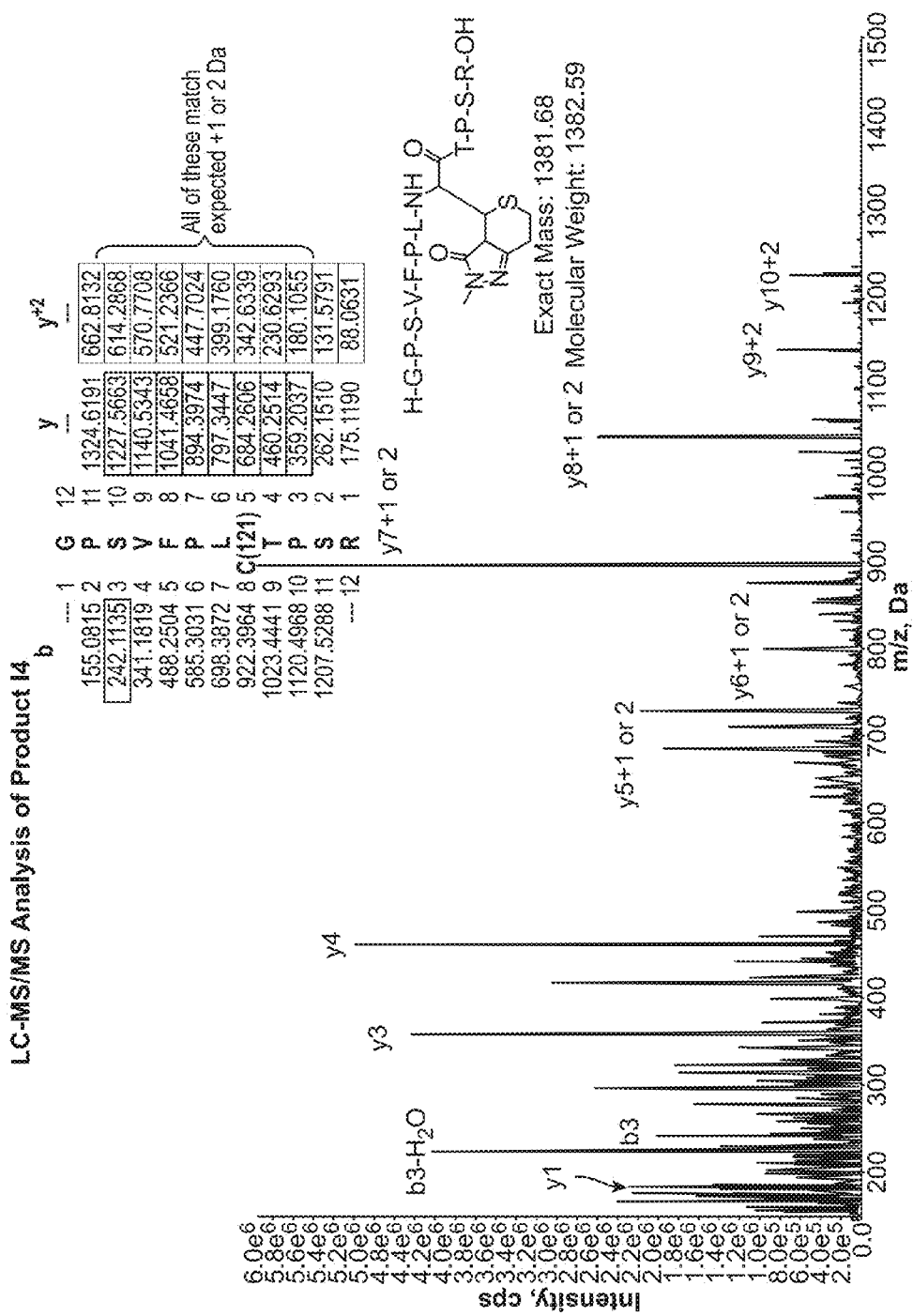
FIG. 8D is a LC-MS/MS analysis of Product I4 from the conjugation reaction.

Results of the conjugation reaction are shown in FIGS. 8A-8D. FIG. 8A shows a series of RP HPLC traces including the starting materials (fGly 12 mer and Compound A4) followed by the reaction mixtures at different time points (3 and 15 hours). FIG. 8B is a LC-MS/MS analysis of Product I2 from the conjugation reaction. FIG. 8C is a LC-MS/MS analysis of Product I3 from the conjugation reaction. FIG. 8D is a LC-MS/MS analysis of Product I4 from the conjugation reaction.

Example 18

Conjugation of FGly-Containing Peptide with Amino-Pz Coupling Moiety

The following reagents were combined and aliquots taken at 4 and 16 hours and the reaction monitored for product formation at 215 nm by C18 RP HPLC:
  70 µL MilliQ water,
  10 µL 10×DPBS,
  10 µL 50 mM Compound C3 in DMA,
  10 µL 1 mM H$_2$N-GPSVFPL(fGly)TPSR—OH (SEQ ID NO:3).

Products were isolated via HPLC and analyzed by ESI-MS. Both products were identified to be the double addition product C4 with the major ion being [M+3]/3$^+$, in addition to the parent ion being present [M+H]$^+$.

LRMS (ESI) calcd for C$_{68}$H$_{107}$N$_{21}$O$_{18}$ [M+H]$^+$: 1506.8. found 1506.8; calcd for C$_{68}$H$_{107}$N$_{21}$O$_{18}$ [M+3]/3$^+$: 502.9. found 503.0.

Figure 9A:
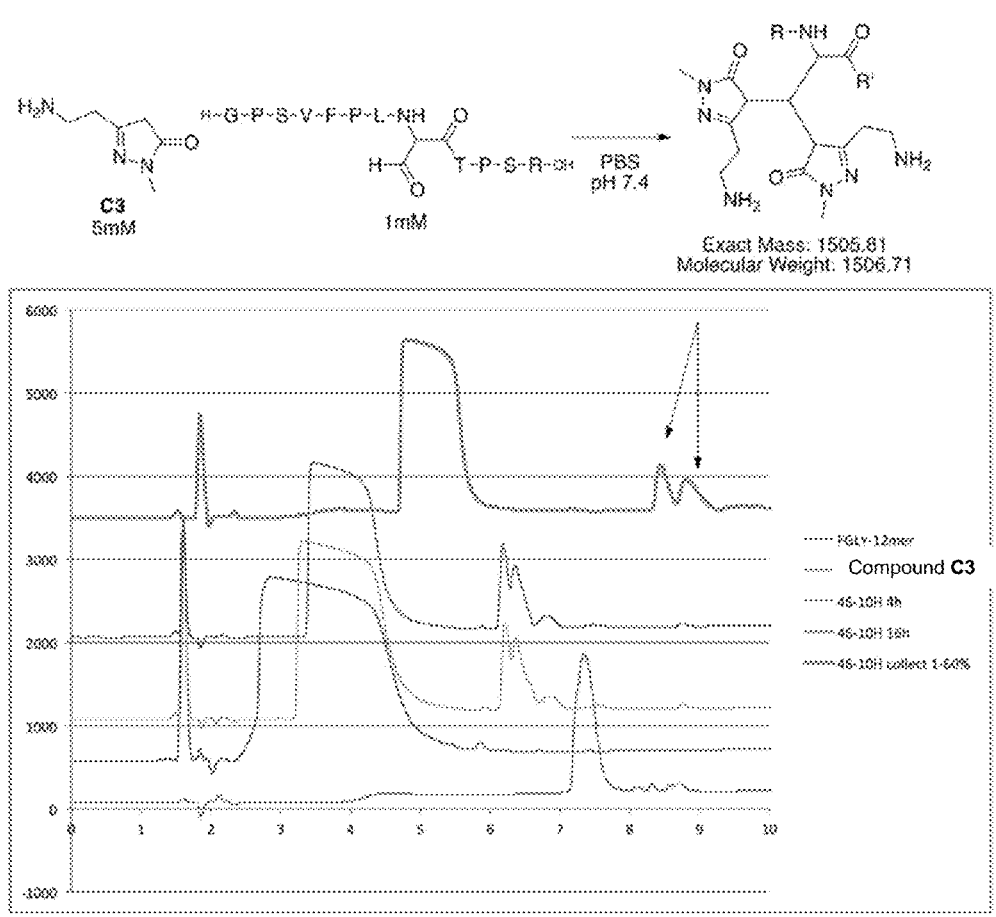
FIG. 9A shows a series of RP HPLC traces including the starting materials (fGly 12 mer and Compound C3) followed by the reaction mixtures at different time points (4 and 16 hours).
Figure 9B:
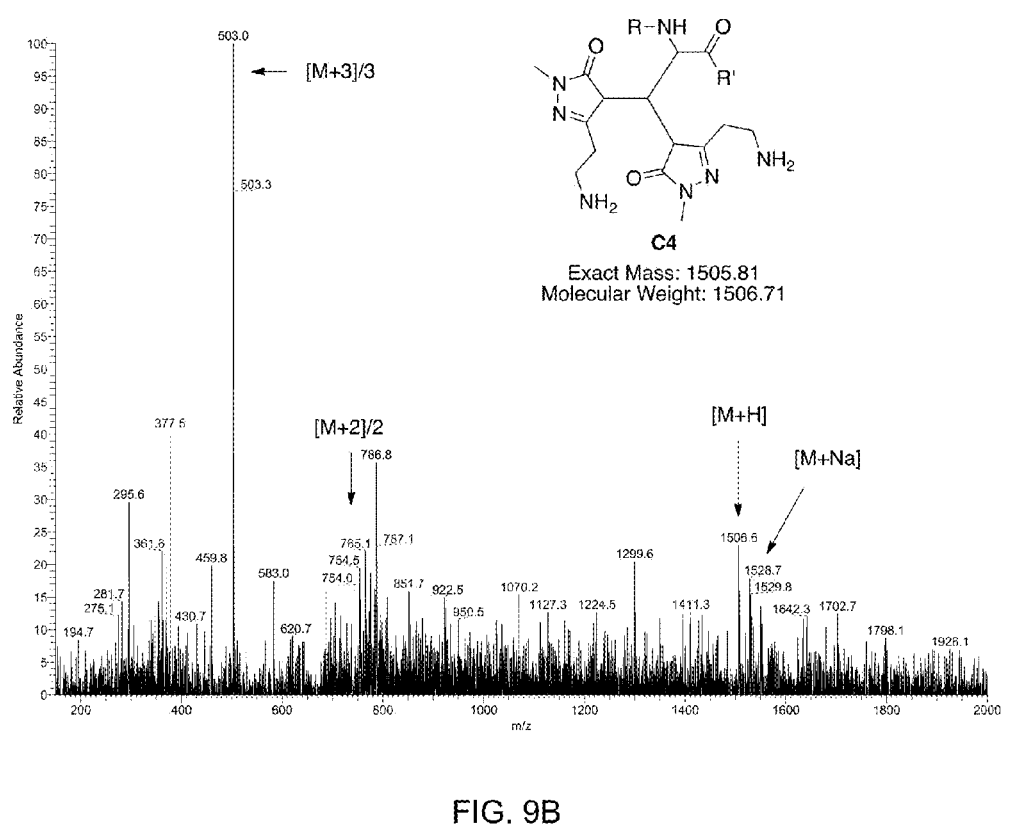
Figure 9C:
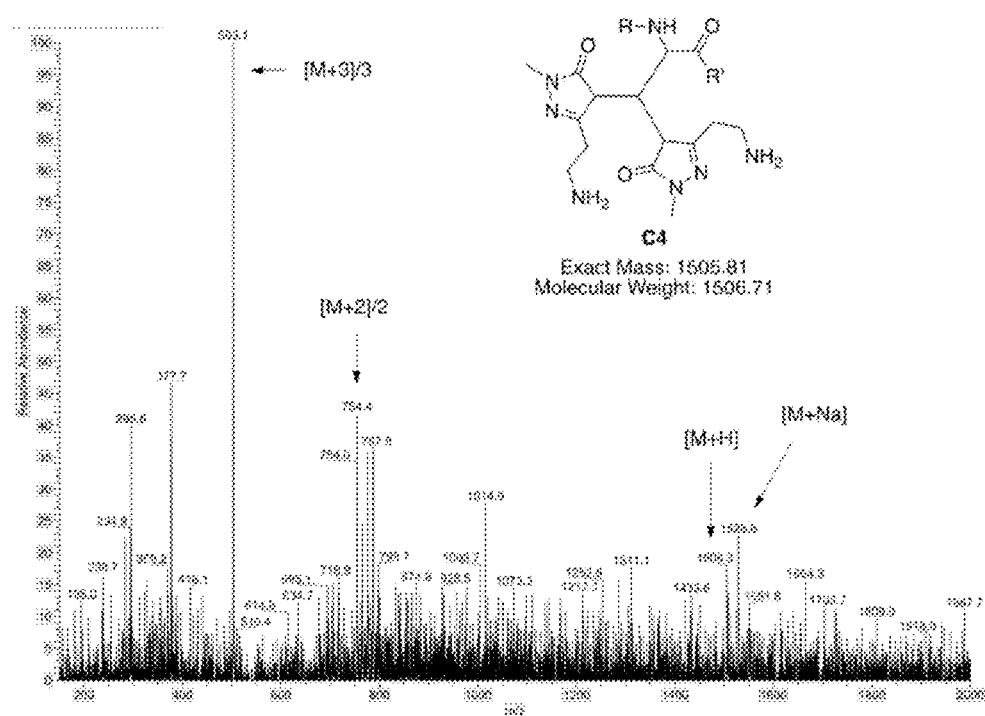

Results of the conjugation reaction are shown in FIGS. 9A-9C. FIG. 9A shows a series of RP HPLC traces including the starting materials (fGly 12 mer and Compound C3) followed by the reaction mixtures at different time points (4 and 16 hours). FIGS. 9B and 9C are LC-MS/MS analyses of Product C4 from the conjugation reaction.

Example 19

Conjugation of FGly-Containing Peptide with Phenol-Pz Coupling Moiety

The following reagents were combined and aliquots taken over time and the reaction monitored for product formation at 215 nm by C18 RP HPLC:
  70 µL MilliQ water,
  10 µL 10×DPBS or 10 µL 500 mM Phosphate Buffer (pH 8.5),
  10 µL 50 mM Compound D1 in DMA,
  10 µL 1 mM H$_2$N-GPSVFPL(fGly)TPSR—OH (SEQ ID NO:3).

Products were isolated via HPLC and analyzed by ESI-MS. The products were identified to be the double addition product and the single addition product. The major ion for the double addition was [M+2]/2$^+$, in addition to the parent ion being present [M+H]$^+$, while the major ion for the single addition was [M+H+Na]/2$^+$, in addition to the parent ion being present [M+H]$^+$.

Figure 10A:
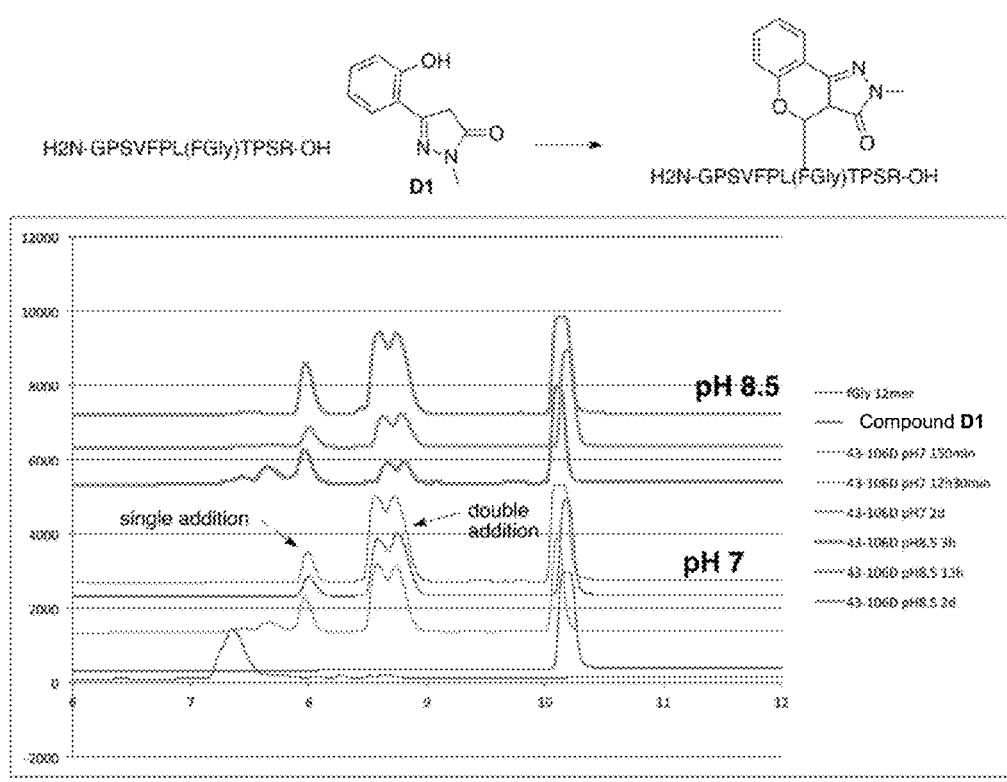
FIG. 10A shows a series of RP HPLC traces including the starting materials (fGly 12 mer and Compound D1) followed by the reaction mixtures over time.
Figure 10B:
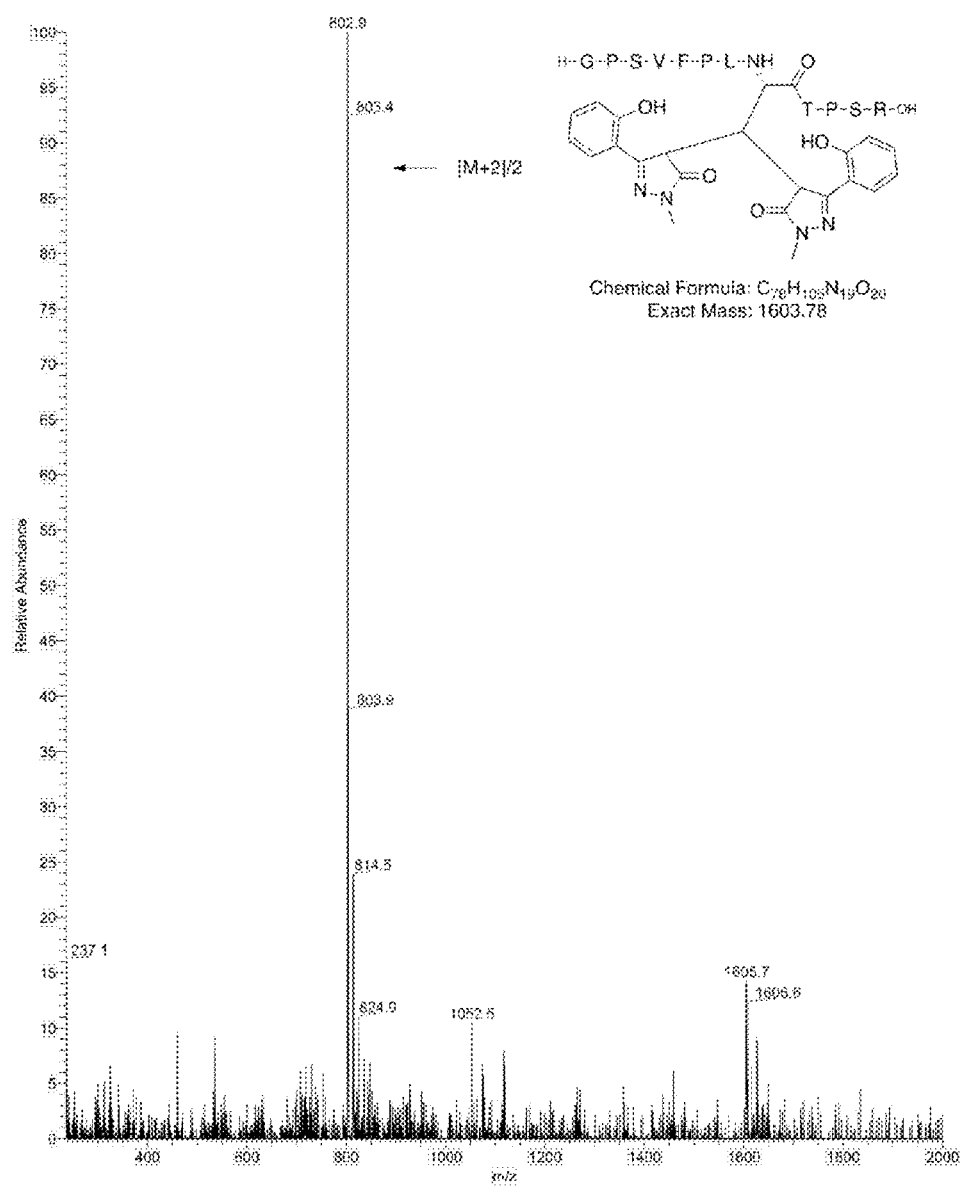
FIGS. 10B and 10C are LC-MS/MS analyses of the double addition product from the conjugation reaction.
Figure 10C:
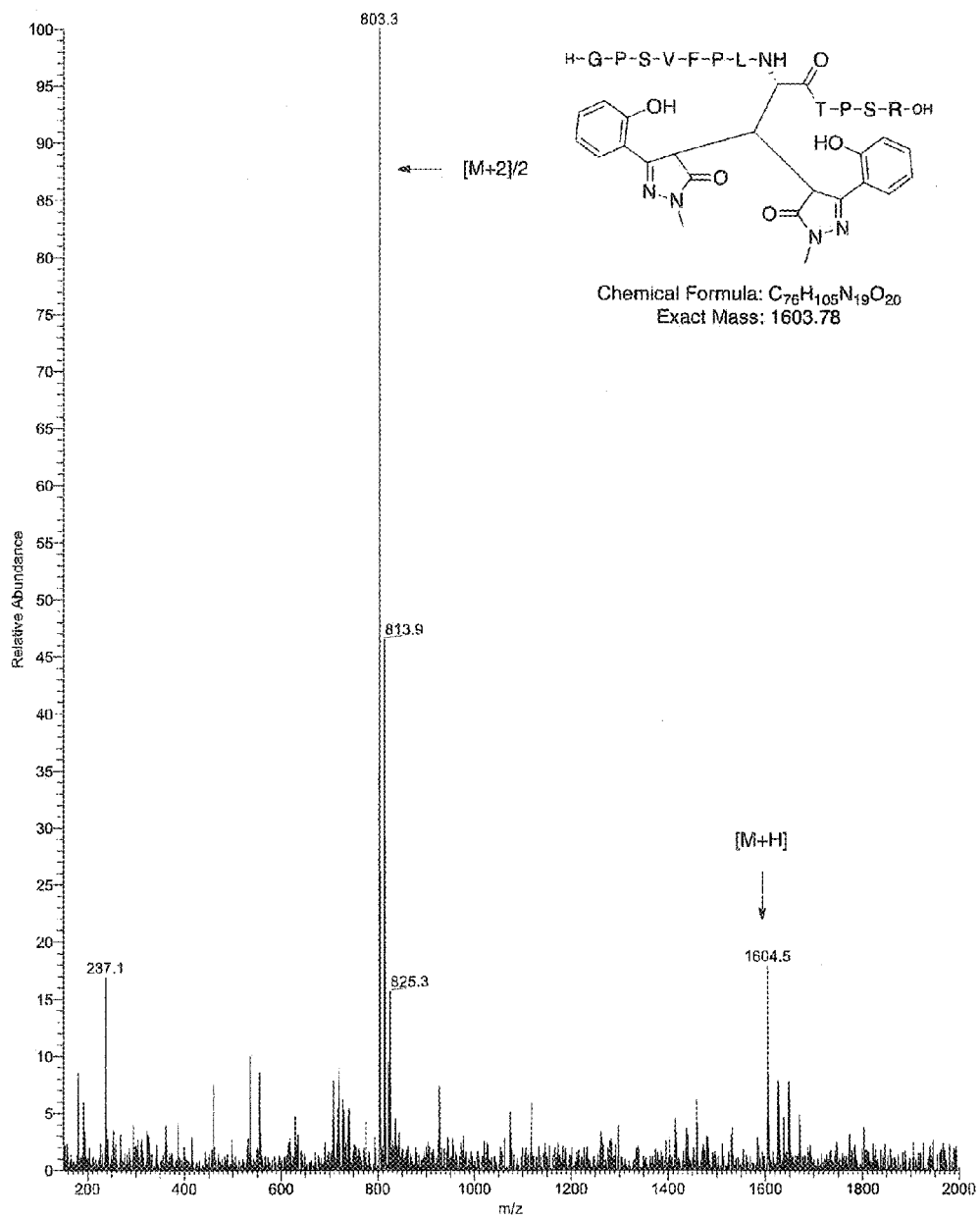
Figure 10D:
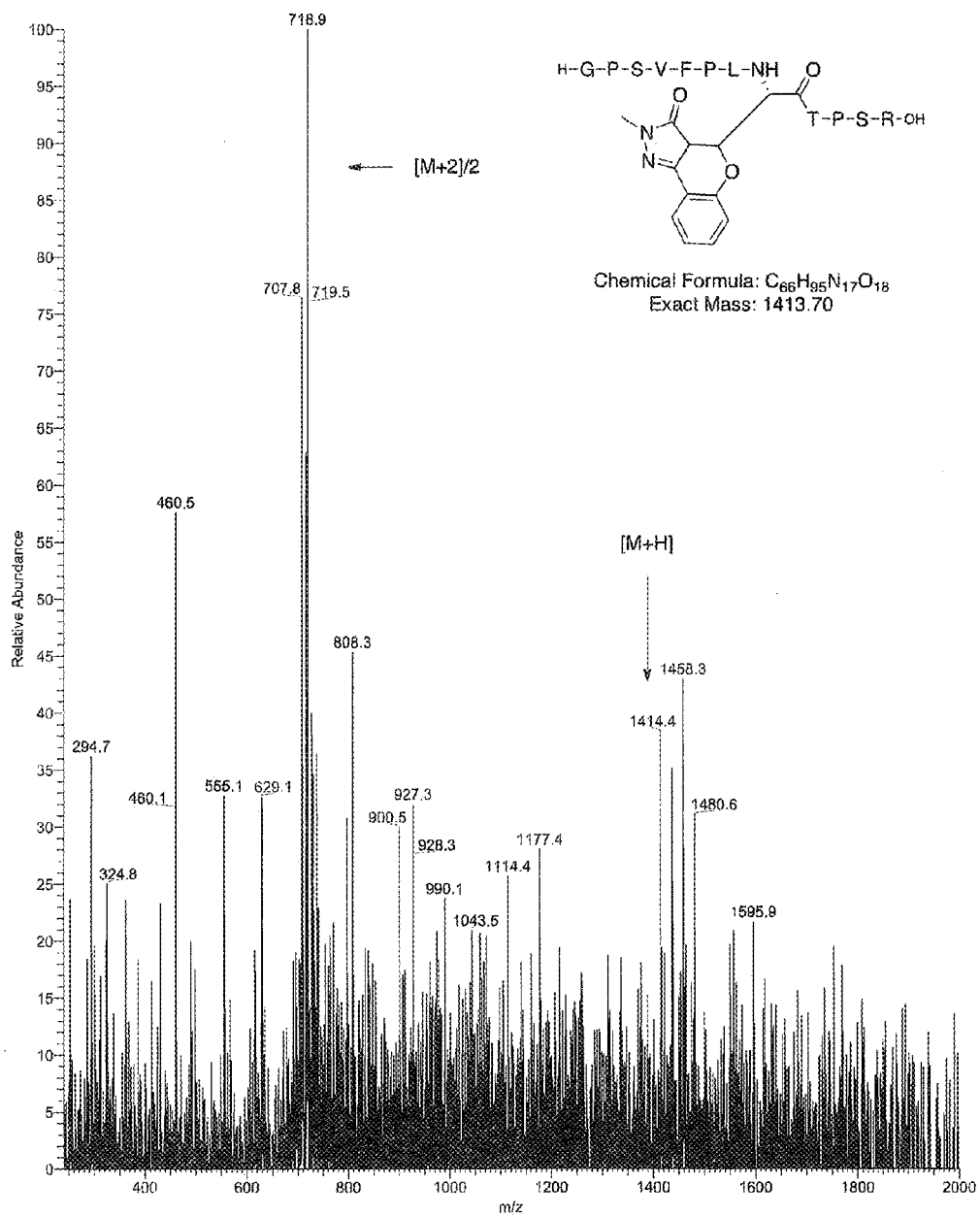
FIG. 10D is a LC-MS/MS analysis of the single addition product from the conjugation reaction.

Results of the conjugation reaction are shown in FIGS. 10A-10D. FIG. 10A shows a series of RP HPLC traces including the starting materials (fGly 12 mer and Compound D1) followed by the reaction mixtures over time. FIGS. 10B and 10C are LC-MS/MS analyses of the double addition product from the conjugation reaction. FIG. 10D is a LC-MS/MS analysis of the single addition product from the conjugation reaction.

Double Addition Product

LRMS (ESI) calcd for $C_{76}H_{105}N_{19}O_{20}$ [M+H]$^+$: 1604.8. found 1605.7; calcd for $C_{76}H_{105}N_{19}O_{20}$ [M+2]/2$^+$: 802.9. found 802.9.

Single Addition Product

LRMS (ESI) calcd for $C_{66}H_{95}N_{17}O_{18}$ [M+H]$^+$: 1414.7. found 1414.4; calcd for $C_{66}H_{95}N_{17}O_{18}$ [M+H+Na]/2$^+$: 718.9. found 718.9.

Example 20

Conjugation of FGly-Containing Peptide with EtO$_2$C-Pz Coupling Moiety

The following reagents were combined and aliquots taken at 0.5, 5 and 10 hours and the reaction monitored for product formation at 215 nm by C18 RP HPLC:

70 μL MilliQ water,

10 μL 10×DPBS,

10 μL 50 mM Compound G1 in DMA,

10 μL 1 mM H$_2$N-GPSVFPL(fGly)TPSR—OH (SEQ ID NO:3).

Products were isolated via HPLC and analyzed by ESI-MS. The major product was identified to be the double addition product. The major ion for the double addition was the parent ion.

LRMS (ESI) calcd for $C_{70}H_{105}N_{19}O_{22}$ [M+H]$^+$: 1564.8. found 1564.7.

Figure 11A:
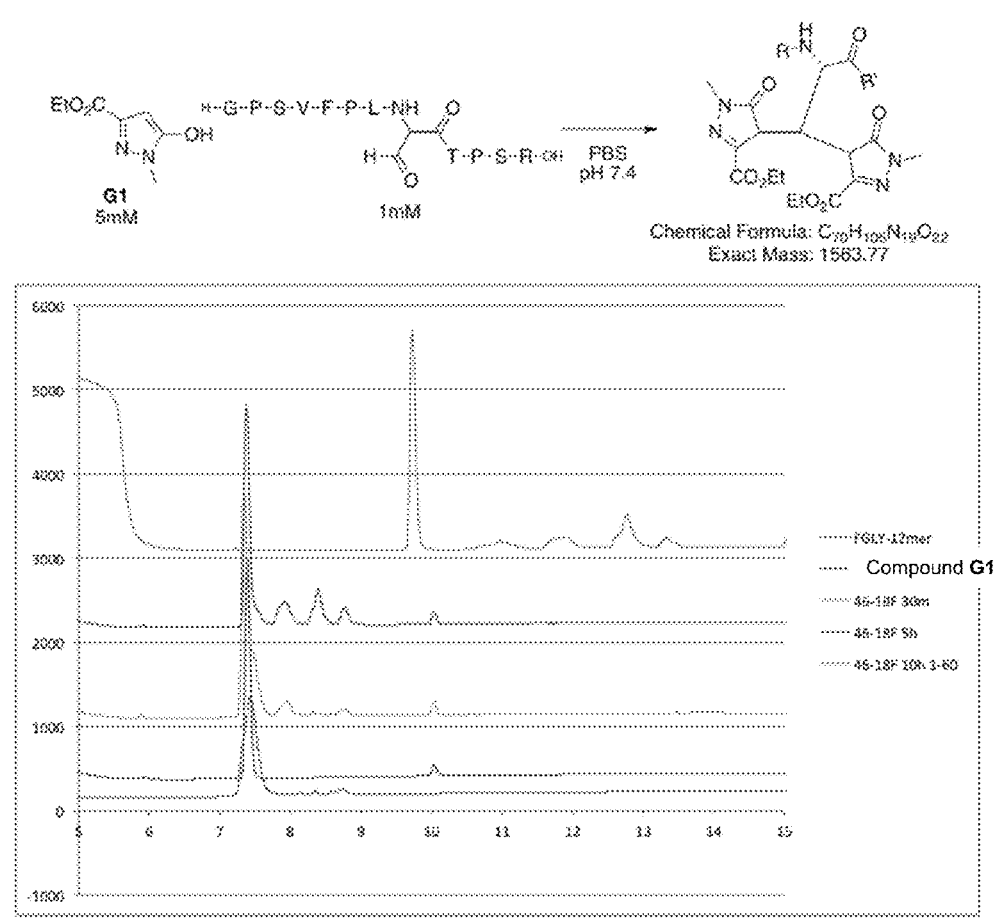
FIG. 11A shows a series of RP HPLC traces including the starting materials (fGly 12 mer and Compound G1) followed by the reaction mixtures at 0.5, 5 and 10 hours.
Figure 11B:
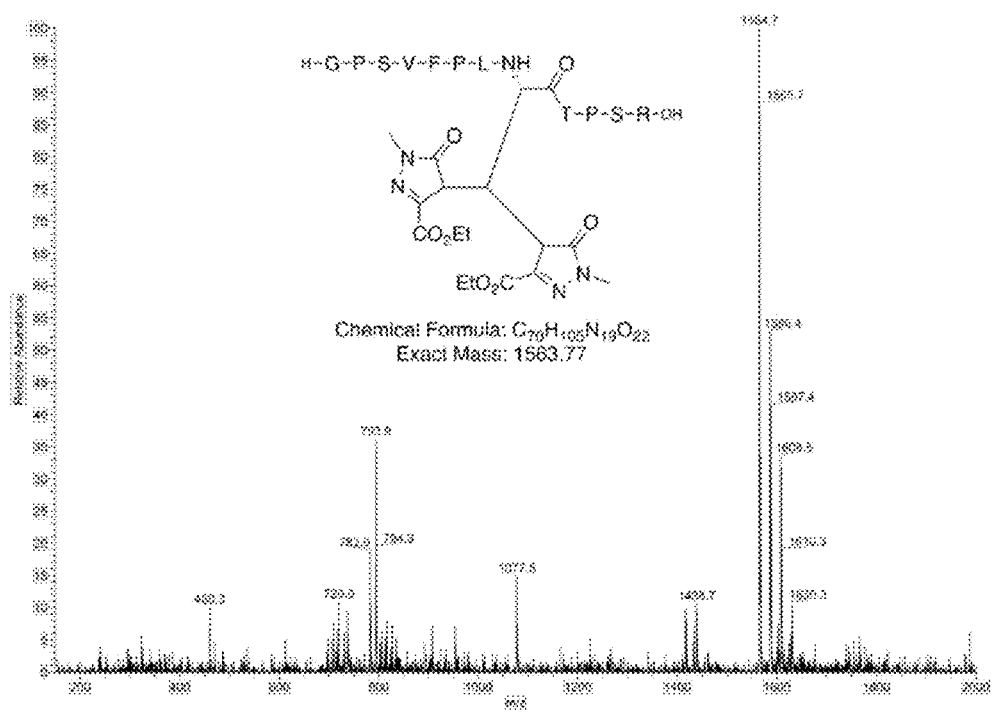
FIG. 11B is a LC-MS/MS analysis of the double addition product from the conjugation reaction.

Results of the conjugation reaction are shown in FIGS. 11A and 11B. FIG. 11A shows a series of RP HPLC traces including the starting materials (fGly 12 mer and Compound G1) followed by the reaction mixtures at 0.5, 5 and 10 hours. FIG. 11B is a LC-MS/MS analysis of the double addition product from the conjugation reaction.

Example 21

Conjugation of Fgly-Containing Peptide with MeO$_2$C—CH$_2$-Pz Coupling Moiety

The following reagents were combined and aliquots taken at 1, 5.5 and 10 hours and the reaction monitored for product formation at 215 nm by C18 RP HPLC:

70 μL MilliQ water,

10 μL 10×DPBS,

10 μL 50 mM Compound H1 in DMA,

10 μL 1 mM H$_2$N-GPSVFPL(fGly)TPSR—OH (SEQ ID NO:3).

Products were isolated via HPLC and analyzed by ESI-MS. The major product was identified to be the double addition product. The major ion for the double addition was the parent ion.

LRMS (ESI) calcd for $C_{70}H_{105}N_{19}O_{22}$ [M+H]$^+$: 1564.8. found 1564.7.

Figure 12A:
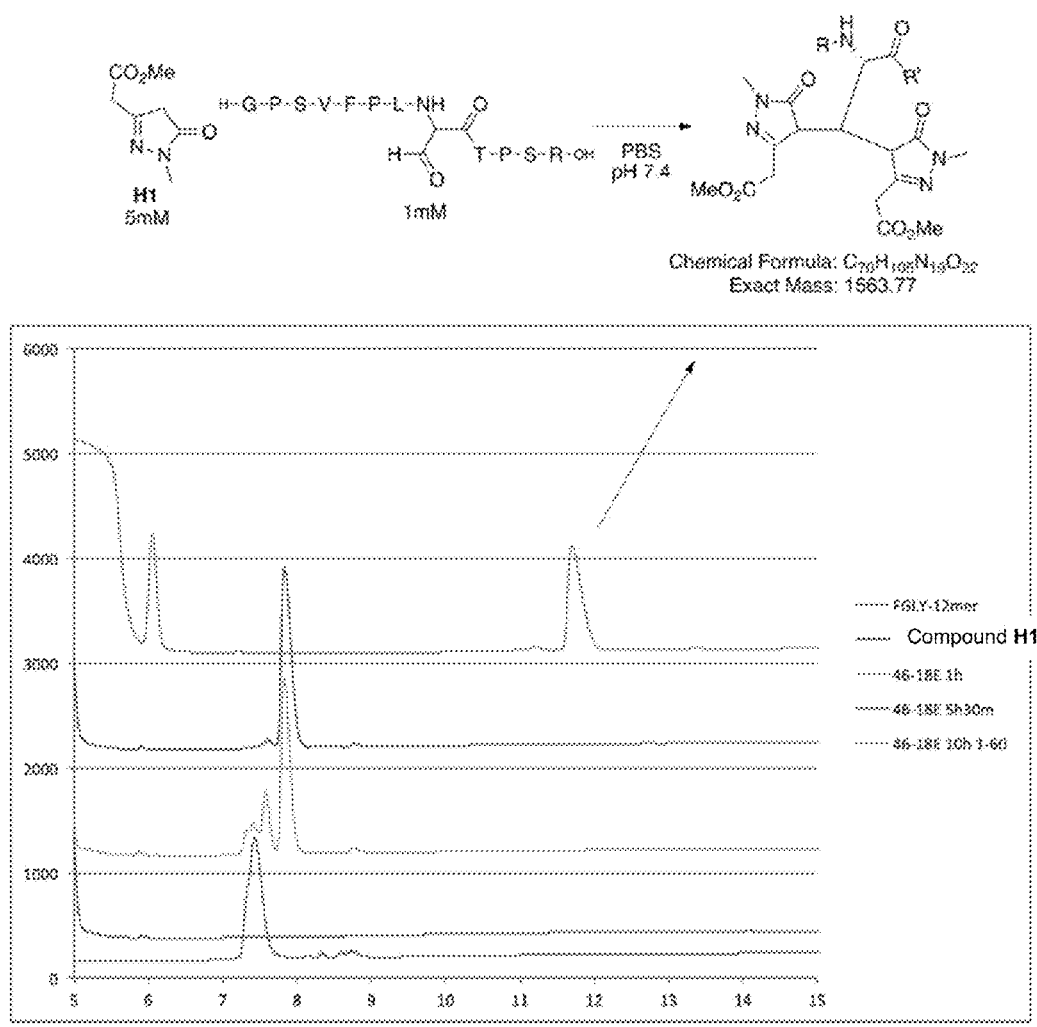
FIG. 12A shows a series of RP HPLC traces including the starting materials (fGly 12 mer and Compound H1) followed by the reaction mixtures at 1, 5.5 and 10 hours.
Figure 12B:
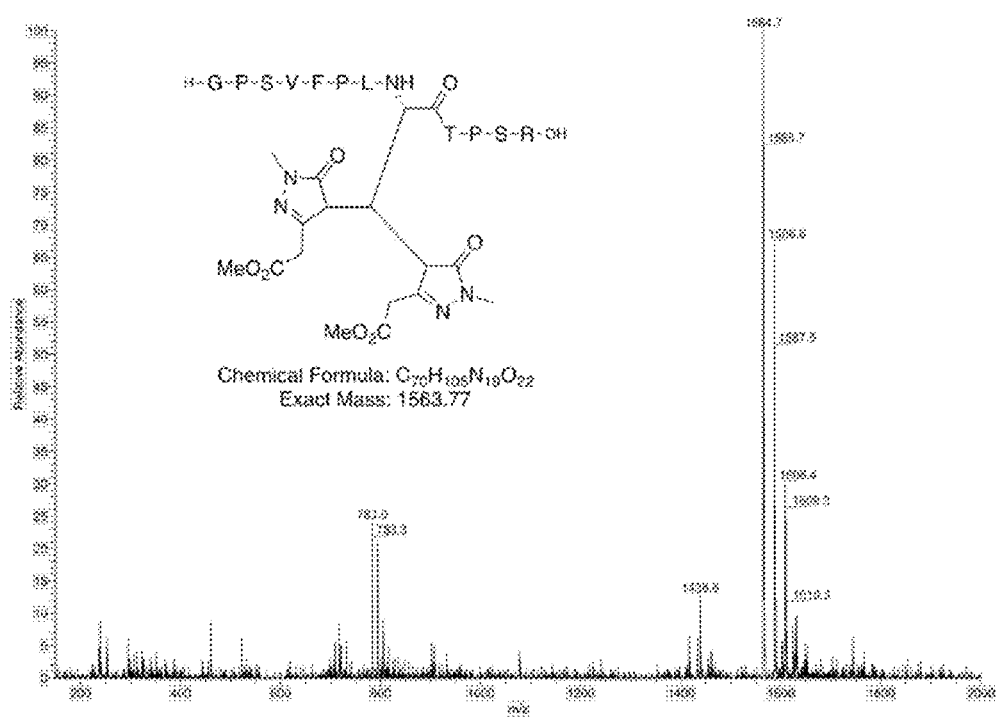
FIG. 12B is a LC-MS/MS analysis of the double addition product from the conjugation reaction.

Results of the conjugation reaction are shown in FIGS. 12A and 12B. FIG. 12A shows a series of RP HPLC traces including the starting materials (fGly 12 mer and Compound H1) followed by the reaction mixtures at 1, 5.5 and 10 hours. FIG. 12B is a LC-MS/MS analysis of the double addition product from the conjugation reaction.

Conjugation of Nucleophiles to fGly-Containing Peptides

Control experiments were performed for the conjugation of fGly-containing peptides to various nucleophiles as described in more detail in the following examples.

Example 22

Conjugation of FGly-Containing Peptide with Dimedone

The following reagents were combined and aliquots taken at 1.5, 11.5 and 48 hours and the reaction monitored for product formation at 215 nm by C18 RP HPLC:

70 μL MilliQ water,

10 μL 10×DPBS,

10 μL 50 mM dimedone in DMA,

10 μL 1 mM H$_2$N-GPSVFPL(fGly)TPSR—OH (SEQ ID NO:3).

Products were isolated via HPLC and analyzed by ESI-MS. The major product was identified to be the double addition product.

LRMS (ESI) calcd for $C_{72}H_{109}N_{15}O_{20}$ [M+H]$^+$: 1504.8. found 1504.7.

Figure 13A:
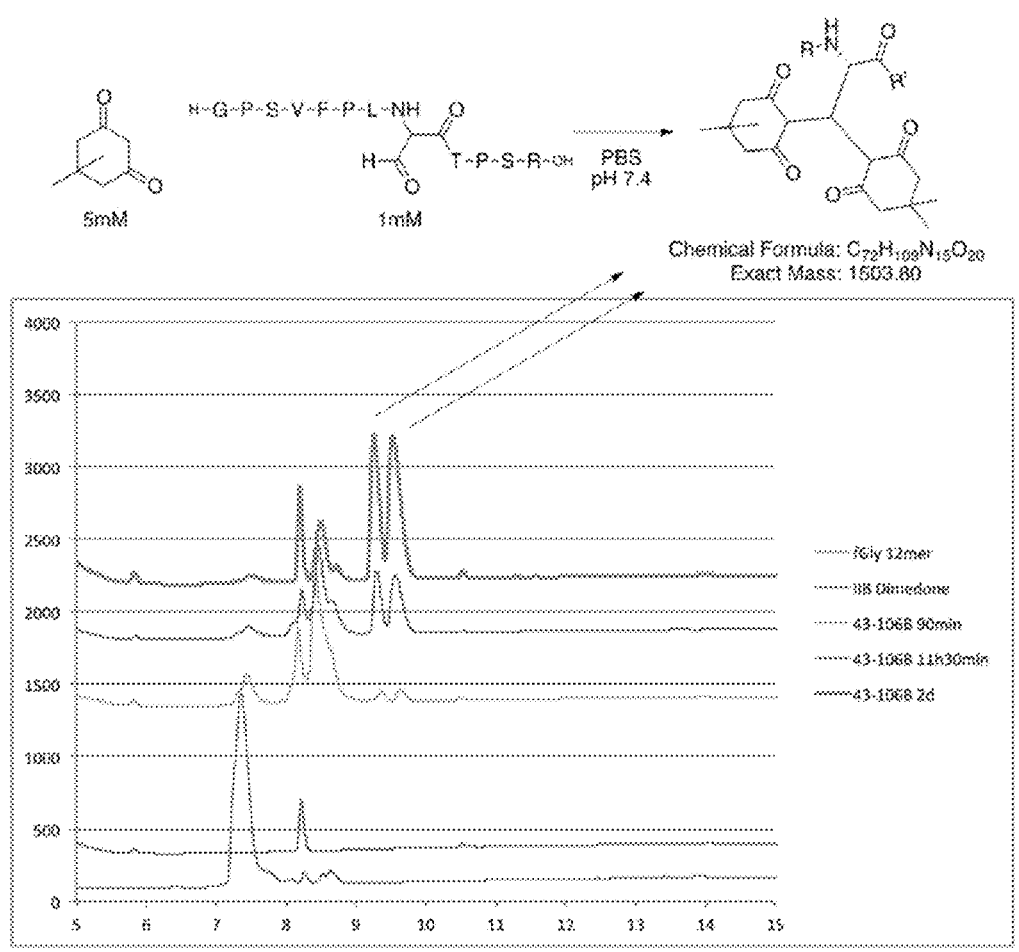
FIG. 13A shows a series of RP HPLC traces including the starting materials (fGly 12 mer and dimedone) followed by the reaction mixtures at different time points (1.5, 11.5 and 48 hours).
Figure 13B:
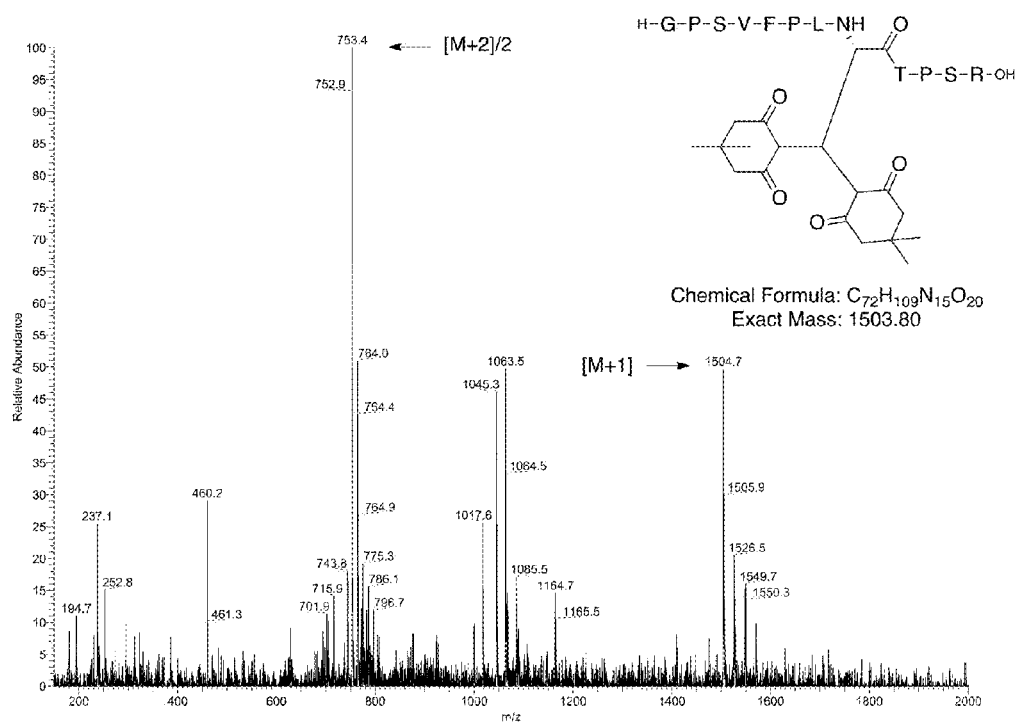
FIG. 13B is a LC-MS/MS analysis of the double addition product from the conjugation reaction.

Results of the conjugation reaction are shown in FIGS. 13A and 13B. FIG. 13A shows a series of RP HPLC traces including the starting materials (fGly 12 mer and dimedone) followed by the reaction mixtures at different time points (1.5, 11.5 and 48 hours). FIG. 13B is a LC-MS/MS analysis of the double addition product from the conjugation reaction.

Example 23

Conjugation of FGly-Containing Peptide with Meldrum's Acid

The following reagents were combined and aliquots taken at 2 and 14 hours and the reaction monitored for product formation at 215 nm by C18 RP HPLC:

70 μL MilliQ water,

10 μL 10×DPBS or 10 μL 500 mM Phosphate Buffer (pH 8.5),

10 μL 50 mM Meldrum's acid in DMA,

10 μL 1 mM H$_2$N-GPSVFPL(fGly)TPSR—OH (SEQ ID NO:3).

Products were isolated via HPLC and analyzed by ESI-MS. The major product was identified to be the single addition product.

LRMS (ESI) calcd for $C_{62}H_{93}N_{15}O_{20}$ [M+H]$^+$: 1368.7. found 1368.5.

Figure 14A:
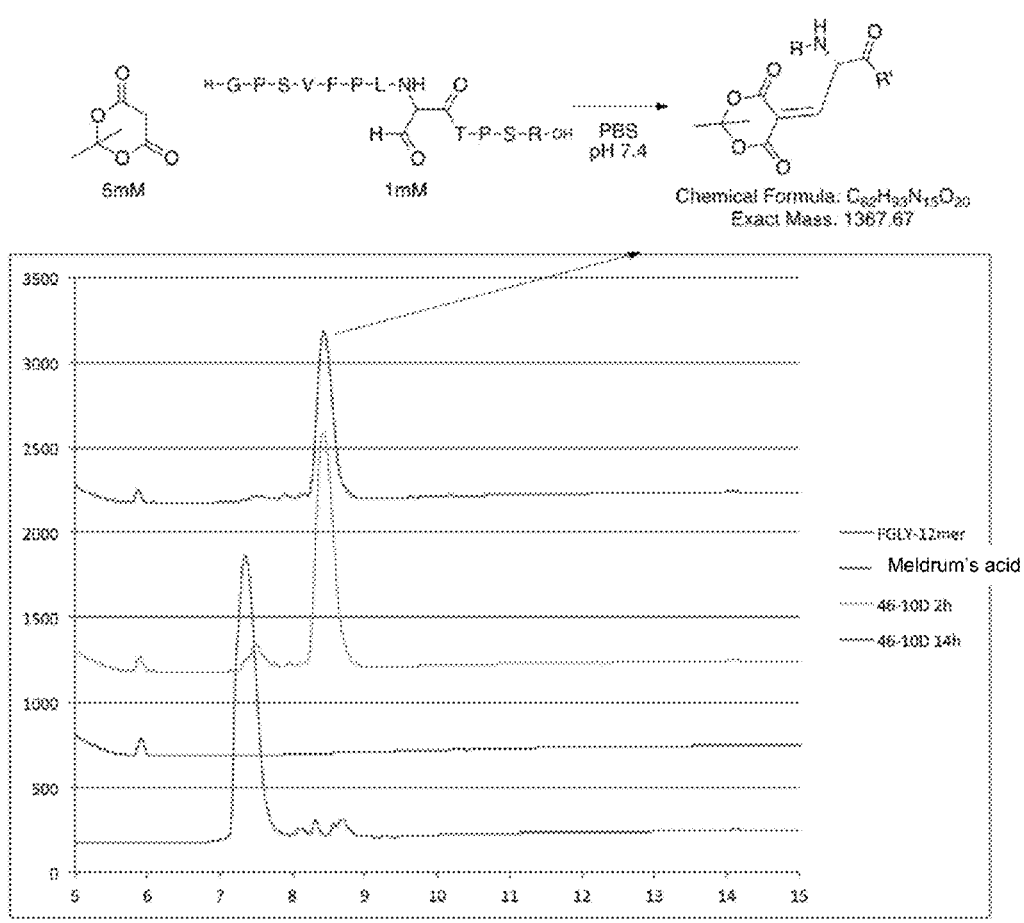
FIG. 14A shows a series of RP HPLC traces including the starting materials (fGly 12 mer and Meldrum's acid) followed by the reaction mixtures at different time points (2 and 14 hours).
Figure 14B:
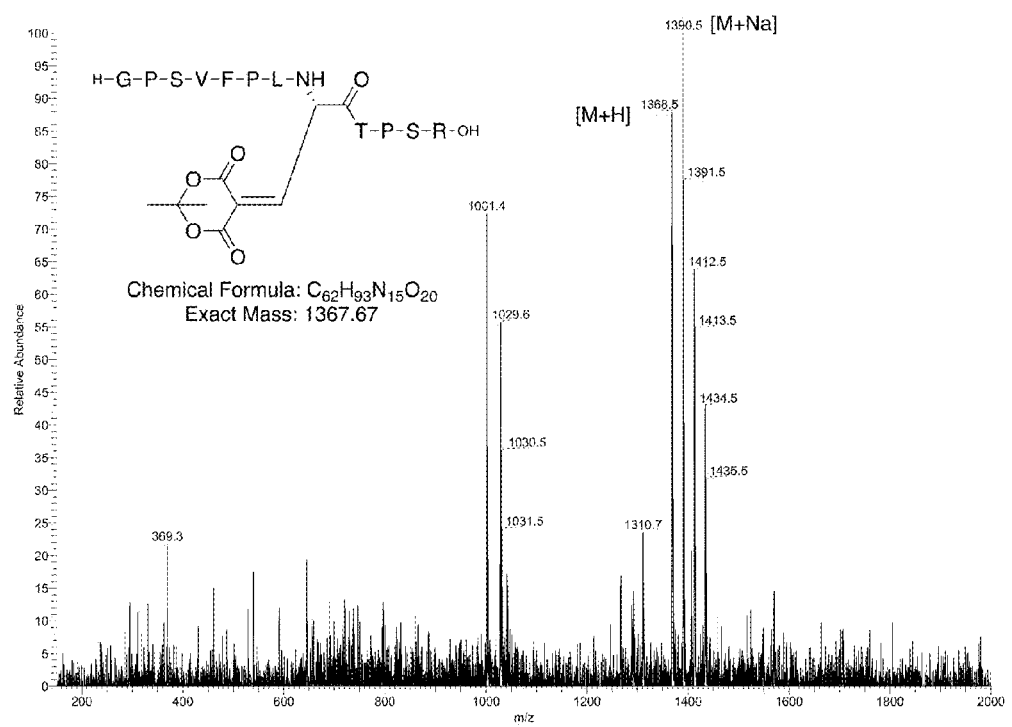
FIG. 14B is a LC-MS/MS analysis of the single addition product from the conjugation reaction.

Results of the conjugation reaction are shown in FIGS. 14A and 14B. FIG. 14A shows a series of RP HPLC traces including the starting materials (fGly 12 mer and Meldrum's acid) followed by the reaction mixtures at different time points (2 and 14 hours). FIG. 14B is a LC-MS/MS analysis of the single addition product from the conjugation reaction.

Example 24

Conjugation of FGly-Containing Peptide with Barbituric Acid

The following reagents were combined and aliquots taken at 2, 6.5 and 10 hours and the reaction monitored for product formation at 215 nm by C18 RP HPLC:

70 μL MilliQ water,

10 μL 10×DPBS or 10 μL 500 mM Phosphate Buffer (pH 8.5),

10 µL 50 mM barbituric acid in DMA,
10 µL 1 mM H$_2$N-GPSVFPL(fGly)TPSR—OH (SEQ ID NO:3).

Products were isolated via HPLC and analyzed by ESI-MS. All products were identified to be single addition products.

LRMS (ESI) calcd for C$_{62}$H$_{93}$N$_{15}$O$_{20}$ [M+H]$^+$: 1352.7. found 1352.5.

Figure 15A:
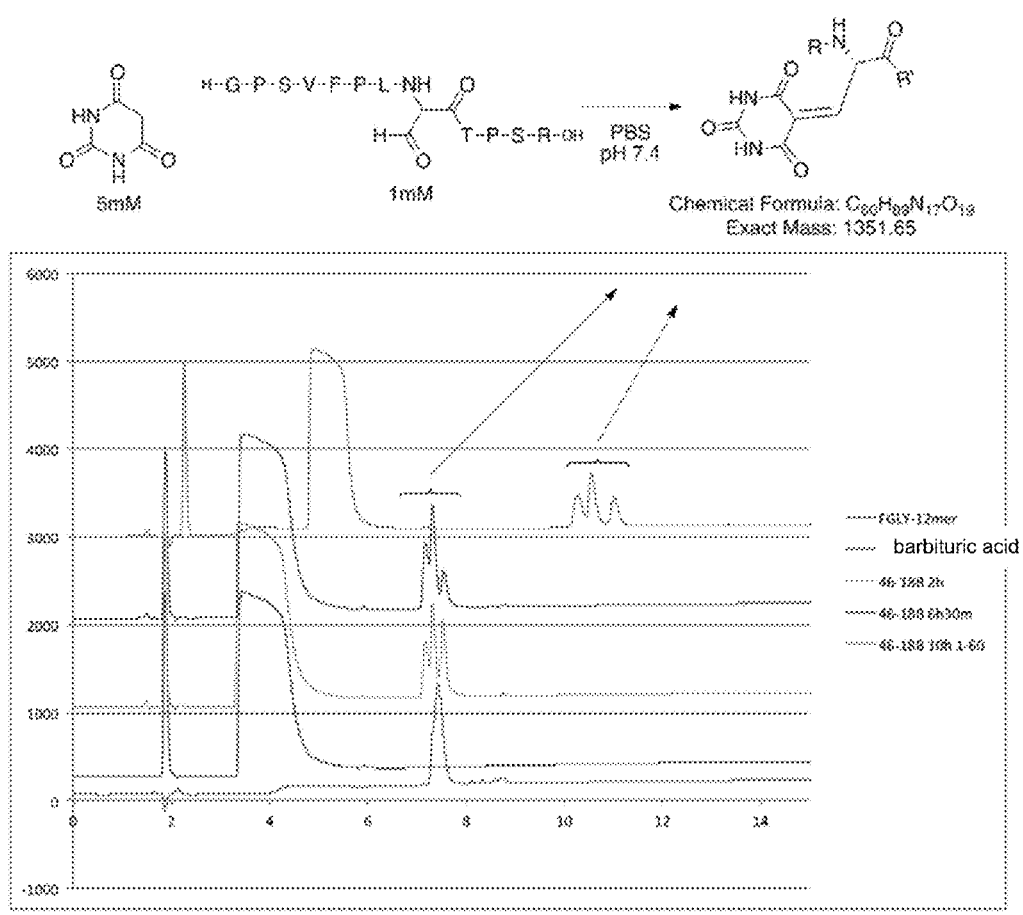
FIG. 15A shows a series of RP HPLC traces including the starting materials (fGly 12 mer and barbituric acid) followed by the reaction mixtures at different time points (2, 6.5 and 10 hours).
Figure 15B:
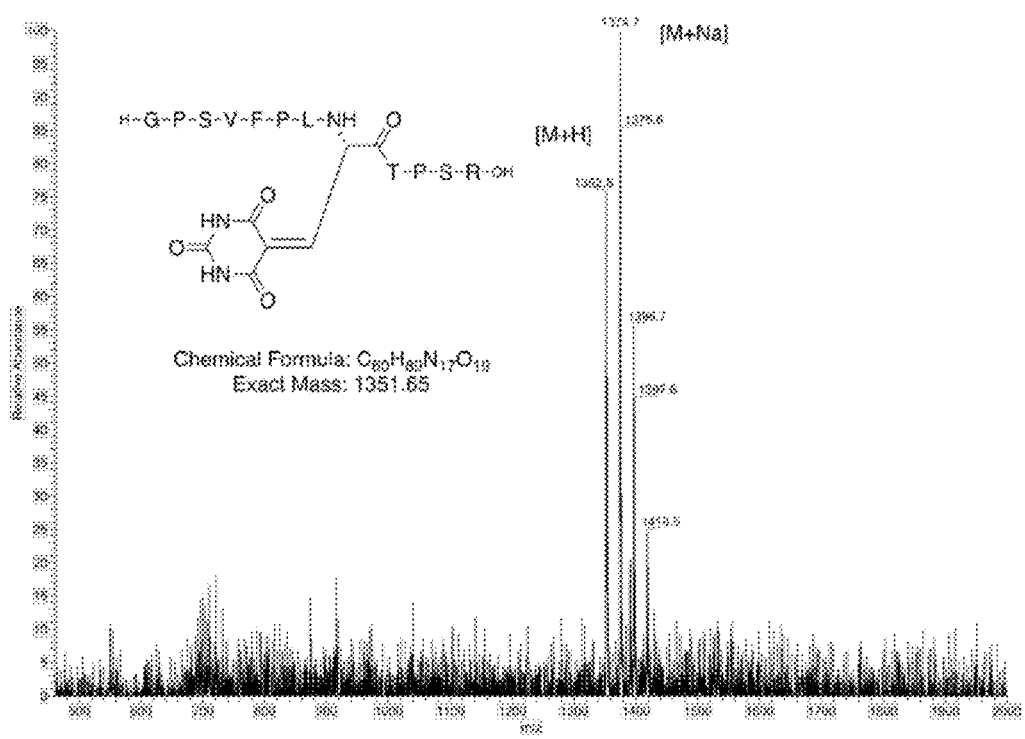
FIGS. 15B-15D are LC-MS/MS analyses of the single addition products from the conjugation reaction.
Figure 15C:
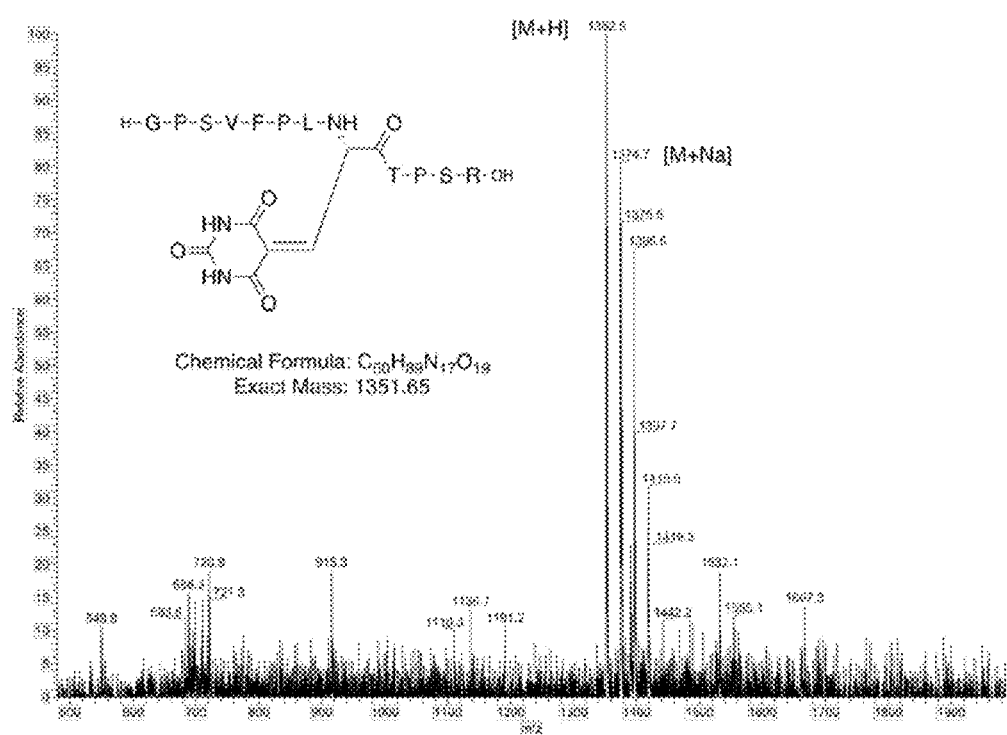
Figure 15D:
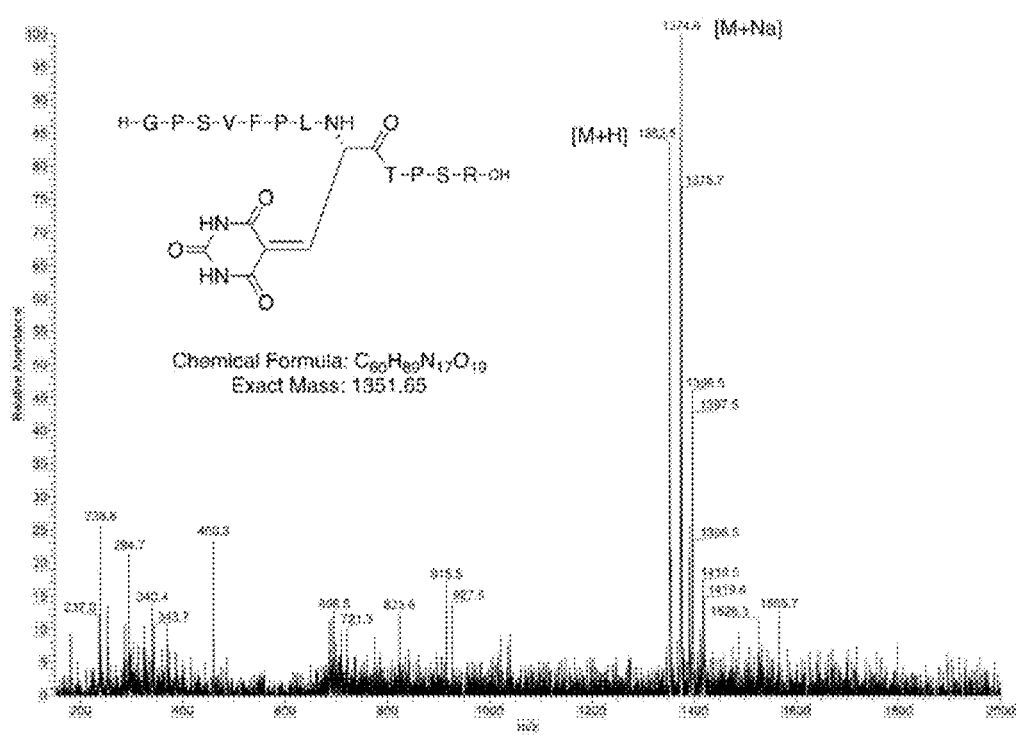

Results of the conjugation reaction are shown in FIGS. 15A-15D. FIG. 15A shows a series of RP HPLC traces including the starting materials (fGly 12 mer and barbituric acid) followed by the reaction mixtures at different time points (2, 6.5 and 10 hours). FIGS. 15B-15D are LC-MS/MS analyses of the single addition products from the conjugation reaction.

Example 25

Conjugation of FGly-Containing Peptide with Tetronic Acid

Tetronic acid undergoes keto-enol tautomerization according to Scheme 17 below.

Scheme 17

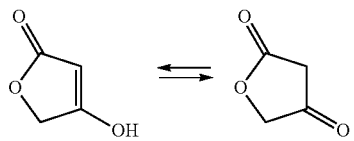

The following reagents were combined and aliquots taken at 2.5 and 14.5 hours and the reaction monitored for product formation at 215 nm by C18 RP HPLC:
70 µL MilliQ water,
10 µL 10×DPBS or 10 µL 500 mM Phosphate Buffer (pH 8.5),
10 µL 50 mM tetronic acid in DMA,
10 µL 1 mM H$_2$N-GPSVFPL(fGly)TPSR—OH (SEQ ID NO:3).

Figure 16:
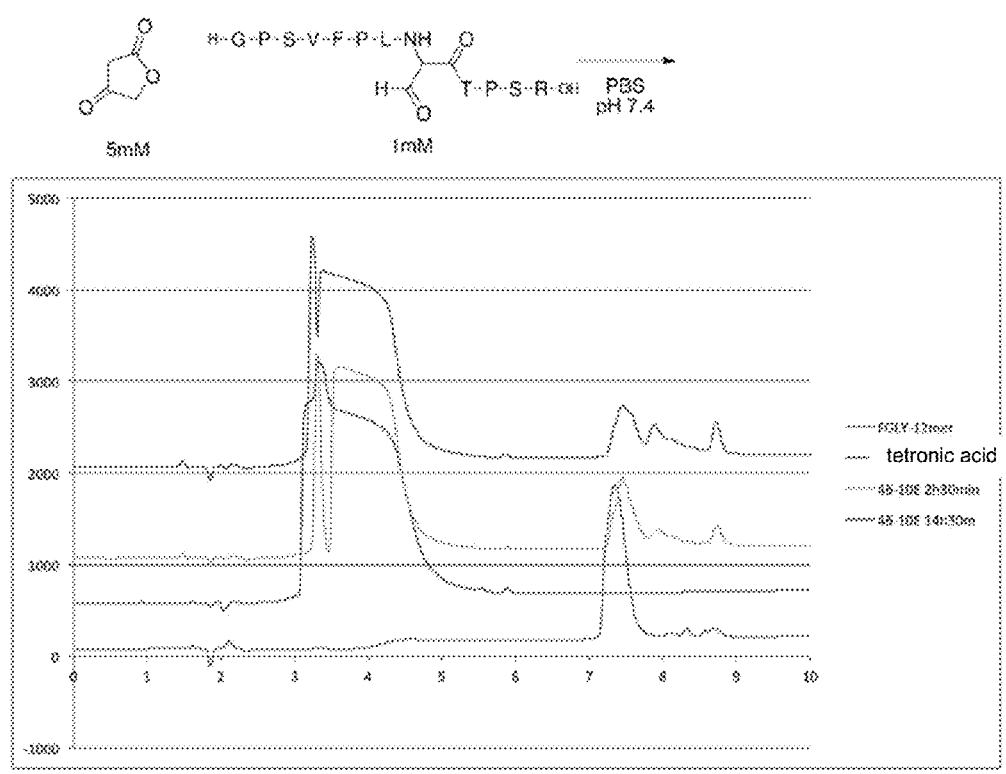
FIG. 16 shows a series of RP HPLC traces including the starting materials (fGly 12 mer and tetronic acid) followed by the reaction mixtures at different time points (2.5 and 14.5 hours).

Conjugation of the fGly-containing peptide with tetronic acid was not observed. Results of the reaction are shown in FIG. 16. FIG. 16 shows a series of RP HPLC traces including the starting materials (fGly 12 mer and tetronic acid) followed by the reaction mixtures at different time points (2.5 and 14.5 hours).

Example 26

Conjugation of FGly-Containing Peptide with Pyrone Derivative

4-Hydroxy-6-methyl-2-pyrone undergoes keto-enol tautomerization according to Scheme 18 below.

Scheme 18

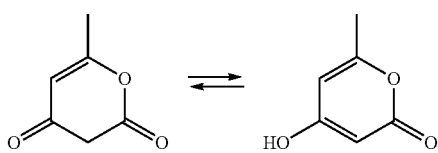

The following reagents were combined and aliquots taken at 1.5 and 13.5 hours and the reaction monitored for product formation at 215 nm by C18 RP HPLC:
70 µL MilliQ water,
10 µL 10×DPBS or 10 µL 500 mM Phosphate Buffer (pH 8.5),
10 µL 50 mM 4-hydroxy-6-methyl-2-pyrone in DMA,
10 µL 1 mM H$_2$N-GPSVFPL(fGly)TPSR—OH (SEQ ID NO:3).

Figure 17:
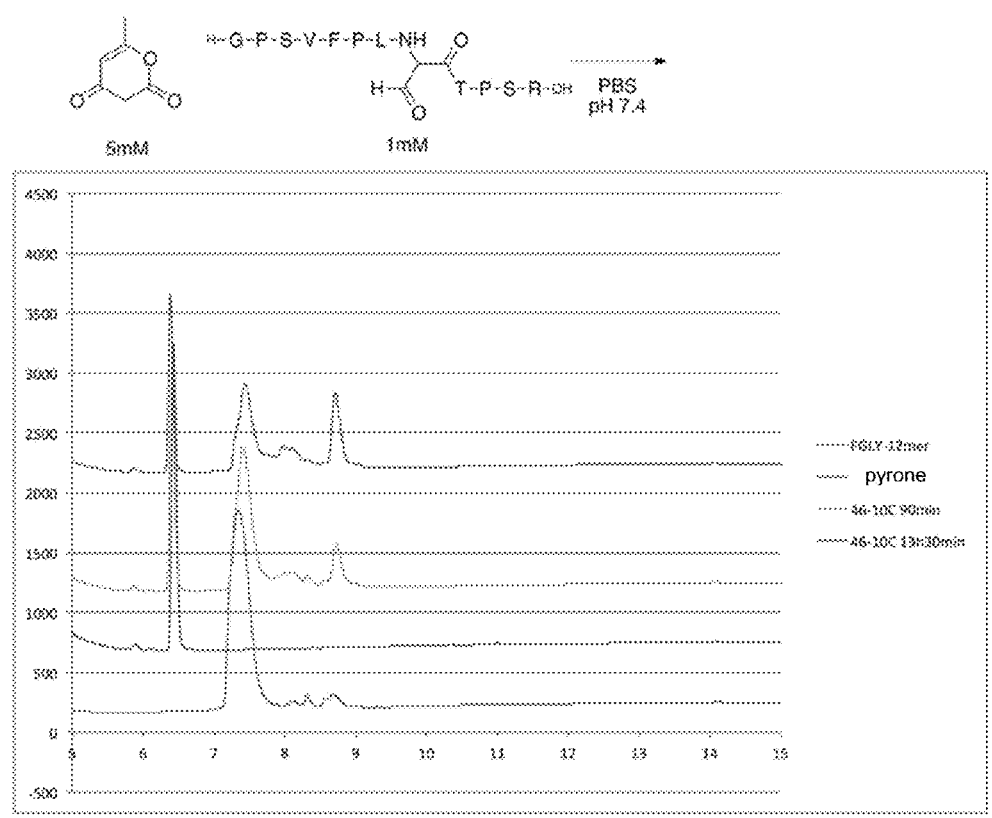
FIG. 17 shows a series of RP HPLC traces including the starting materials (fGly 12 mer and 4-hydroxy-6-methyl-2-pyrone) followed by the reaction mixtures at different time points (1.5 and 13.5 hours).

Conjugation of the fGly-containing peptide with 4-hydroxy-6-methyl-2-pyrone was not observed. Results of the reaction are shown in FIG. 17. FIG. 17 shows a series of RP HPLC traces including the starting materials (fGly 12 mer and 4-hydroxy-6-methyl-2-pyrone) followed by the reaction mixtures at different time points (1.5 and 13.5 hours).

Example 27

Conjugation of FGly-Containing Peptide with Furanone

The following reagents were combined and aliquots taken at 1.5, 6 and 10 hours and the reaction monitored for product formation at 215 nm by C18 RP HPLC:
70 µL MilliQ water,
10 µL 10×DPBS or 10 µL 500 mM Phosphate Buffer (pH 8.5),
10 µL 50 mM 2(5H)-furanone in DMA,
10 µL 1 mM H$_2$N-GPSVFPL(fGly)TPSR—OH (SEQ ID NO:3).

Figure 18:
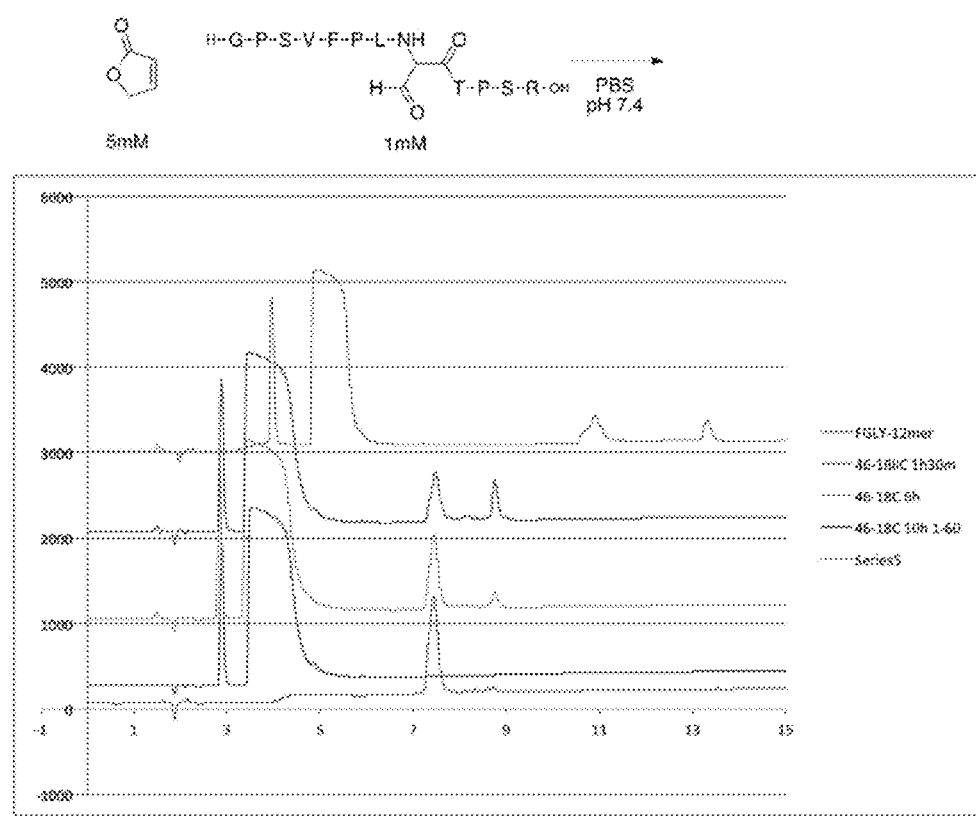
FIG. 18 shows a series of RP HPLC traces including the starting materials (fGly 12 mer and 2(5H)-furanone) followed by the reaction mixtures at different time points (1.5, 6 and 10 hours).

Conjugation of the fGly-containing peptide with 2(5H)-furanone was not observed. Results of the reaction are shown in FIG. 18. FIG. 18 shows a series of RP HPLC traces including the starting materials (fGly 12 mer and 2(5H)-furanone) followed by the reaction mixtures at different time points (1.5, 6 and 10 hours).

Example 28

Conjugation of FGly-Containing Peptide with (Phenylsulfonyl)Acetonitrile

The following reagents were combined and aliquots taken at 0.5 and 12.5 hours and the reaction monitored for product formation at 215 nm by C18 RP HPLC:
70 µL MilliQ water,
10 µL 10×DPBS or 10 µL 500 mM Phosphate Buffer (pH 8.5),
10 µL 50 mM (phenylsulfonyl)acetonitrile in DMA,
10 µL 1 mM H$_2$N-GPSVFPL(fGly)TPSR—OH (SEQ ID NO:3).

Figure 19:
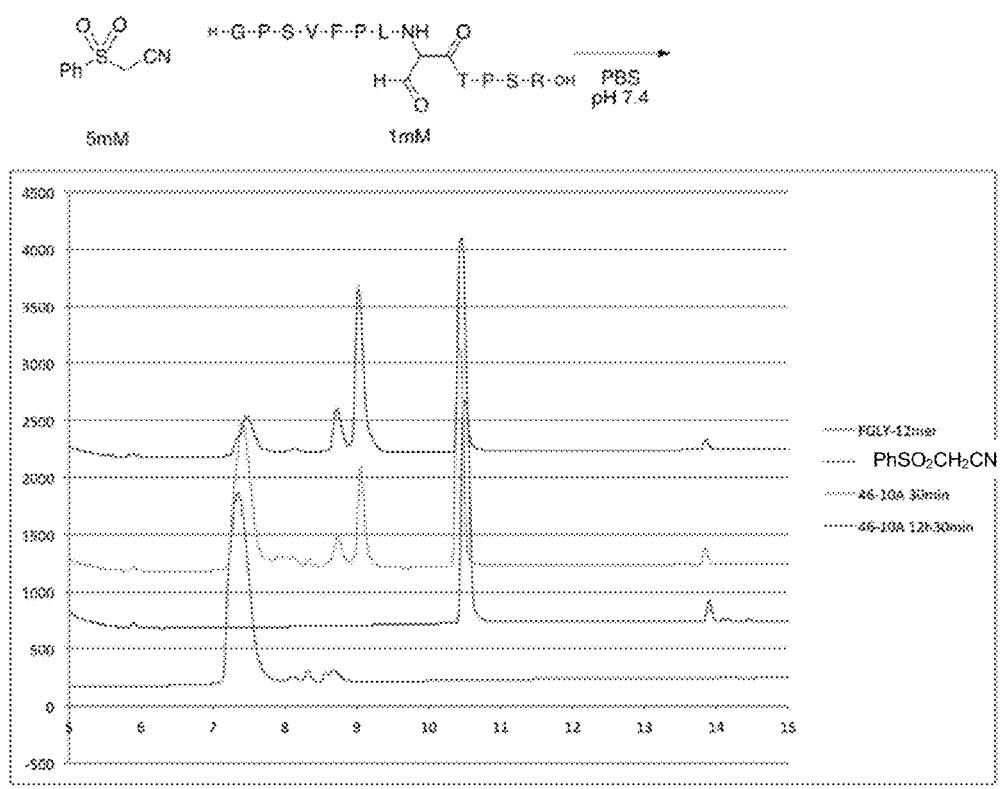
FIG. 19 shows a series of RP HPLC traces including the starting materials (fGly 12 mer and (phenylsulfonyl)acetonitrile) followed by the reaction mixtures at different time points (0.5 and 12.5 hours).

Conjugation of the fGly-containing peptide with (phenylsulfonyl)acetonitrile (PhSO$_2$—CH$_2$—CN) was not observed. Results of the reaction are shown in FIG. 19. FIG. 19 shows a series of RP HPLC traces including the starting materials (fGly 12 mer and (phenylsulfonyl)acetonitrile) followed by the reaction mixtures at different time points (0.5 and 12.5 hours).

Example 29

Conjugation of FGly-Containing Peptide with Nitromethyl Phenyl Sulfone

The following reagents were combined and aliquots taken at 1 and 13 hours and the reaction monitored for product formation at 215 nm by C18 RP HPLC:

70 μL MilliQ water,

10 μL 10×DPBS or 10 μL 500 mM Phosphate Buffer (pH 8.5),

10 μL 50 mM nitromethyl phenyl sulfone in DMA,

10 μL 1 mM H$_2$N-GPSVFPL(fGly)TPSR—OH (SEQ ID NO:3).

Figure 20:
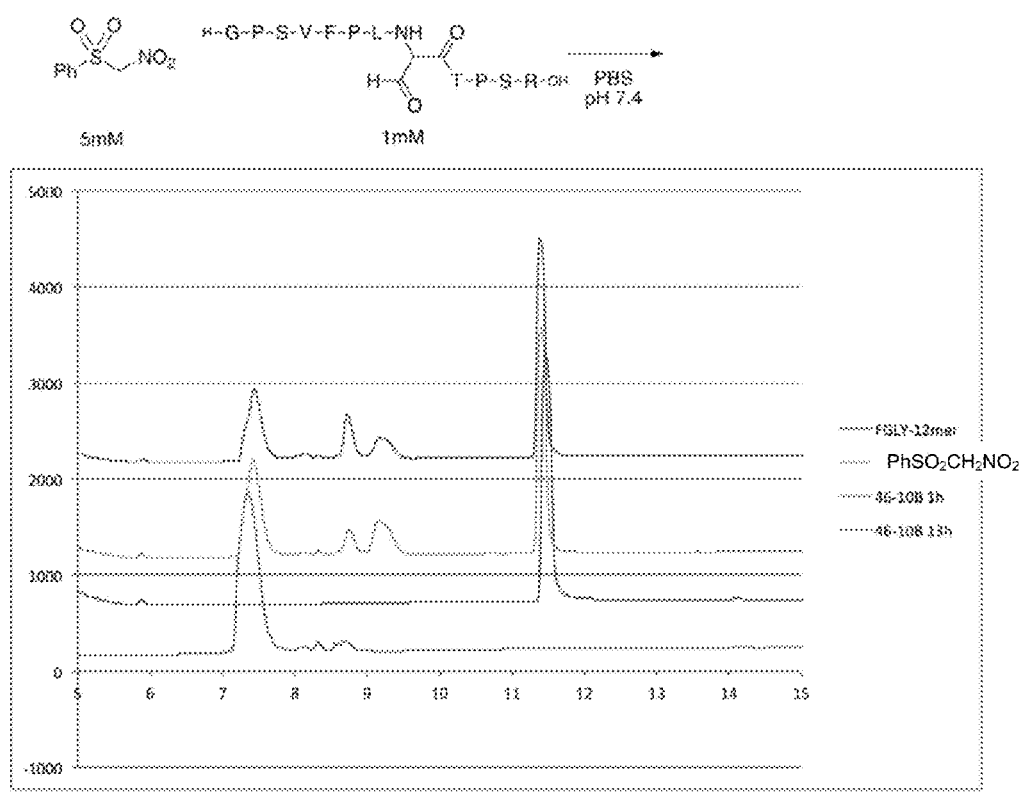
FIG. 20 shows a series of RP HPLC traces including the starting materials (fGly 12 mer and nitromethyl phenyl sulfone) followed by the reaction mixtures at different time points (1 and 13 hours).

Conjugation of the fGly-containing peptide with nitromethyl phenyl sulfone (PhSO$_2$—CH$_2$—NO$_2$) was not observed. Results of the reaction are shown in FIG. 20. FIG. 20 shows a series of RP HPLC traces including the starting materials (fGly 12 mer and nitromethyl phenyl sulfone) followed by the reaction mixtures at different time points (1 and 13 hours).

Conjugation of Pyrazalinone Ligation Reagent to an Aldehyde-Tagged Antibody

Experiments were performed to conjugate an aldehyde-tagged antibody to a pyrazalinone ligation reagent described above according to embodiments of the present disclosure.

Example 30

Conjugation of Aldehyde-Tagged Antibody with Pz-pH-2PEG-Maytansine

Pz-Ph-2PEG-Maytansine was synthesized according to Example 7 above.

Aldehyde-tagged antibody (A) was reacted with Pz-Ph-2PEG-Maytansine in PBS at pH 7, 37° C., with 2.5% DMA. The reaction mixture was analyzed by hydrophobic interaction column (HIC) after 24 hours (FIG. 7, bottom panel). Both the mono-conjugate (B) and di-conjugate (D) protein conjugate were observed. FIG. 7 also shows a hydrophobic interaction column (HIC) trace of aldehyde-tagged antibody (A) (FIG. 7, top panel).

MS Characterization of Pz-Modified mAb

Figure 21:
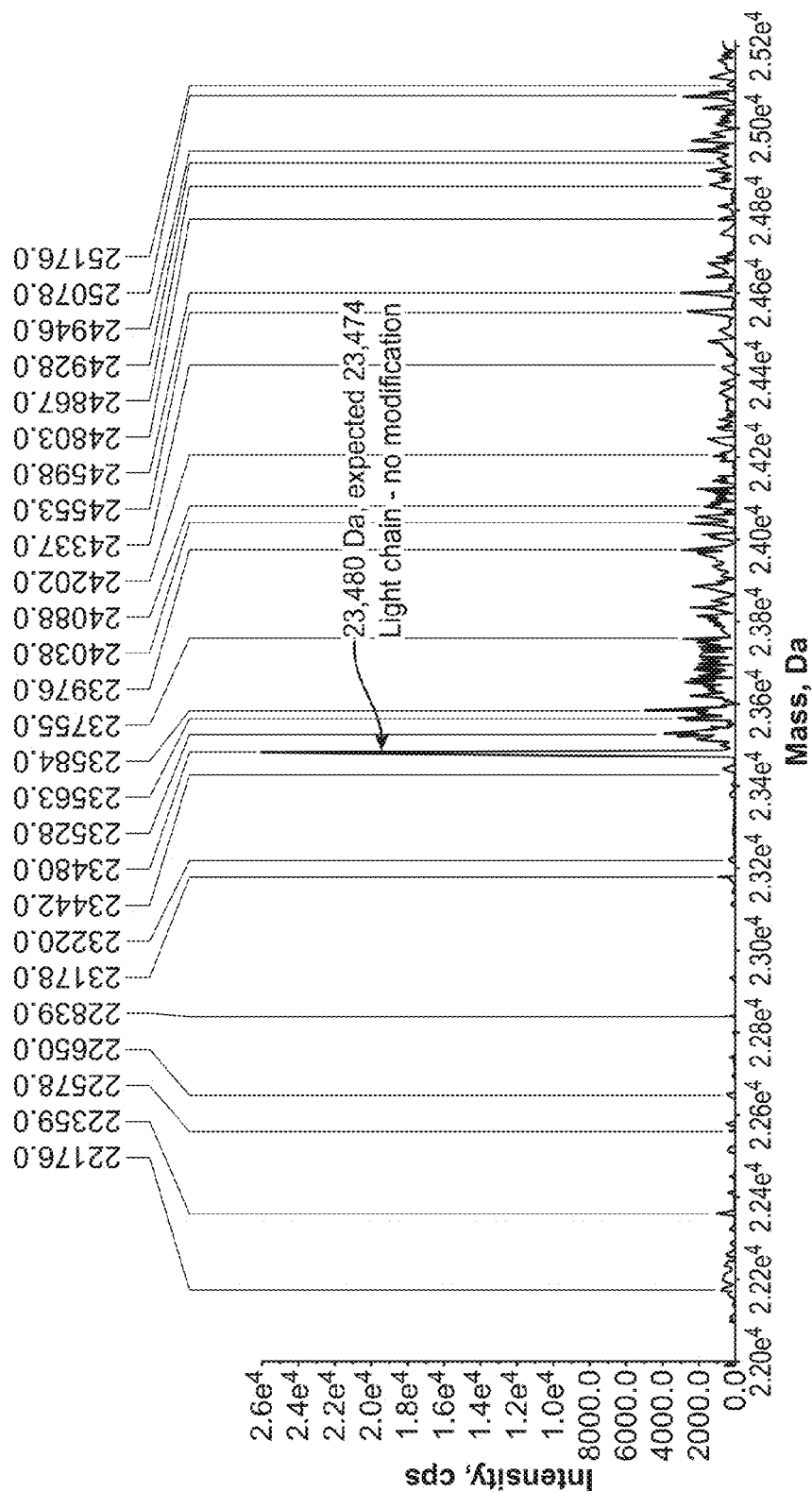
FIG. 21 shows MS data showing no reaction of Pz with the light chain of C-terminal aldehyde-tagged antibody (top panel).
Figure 21:
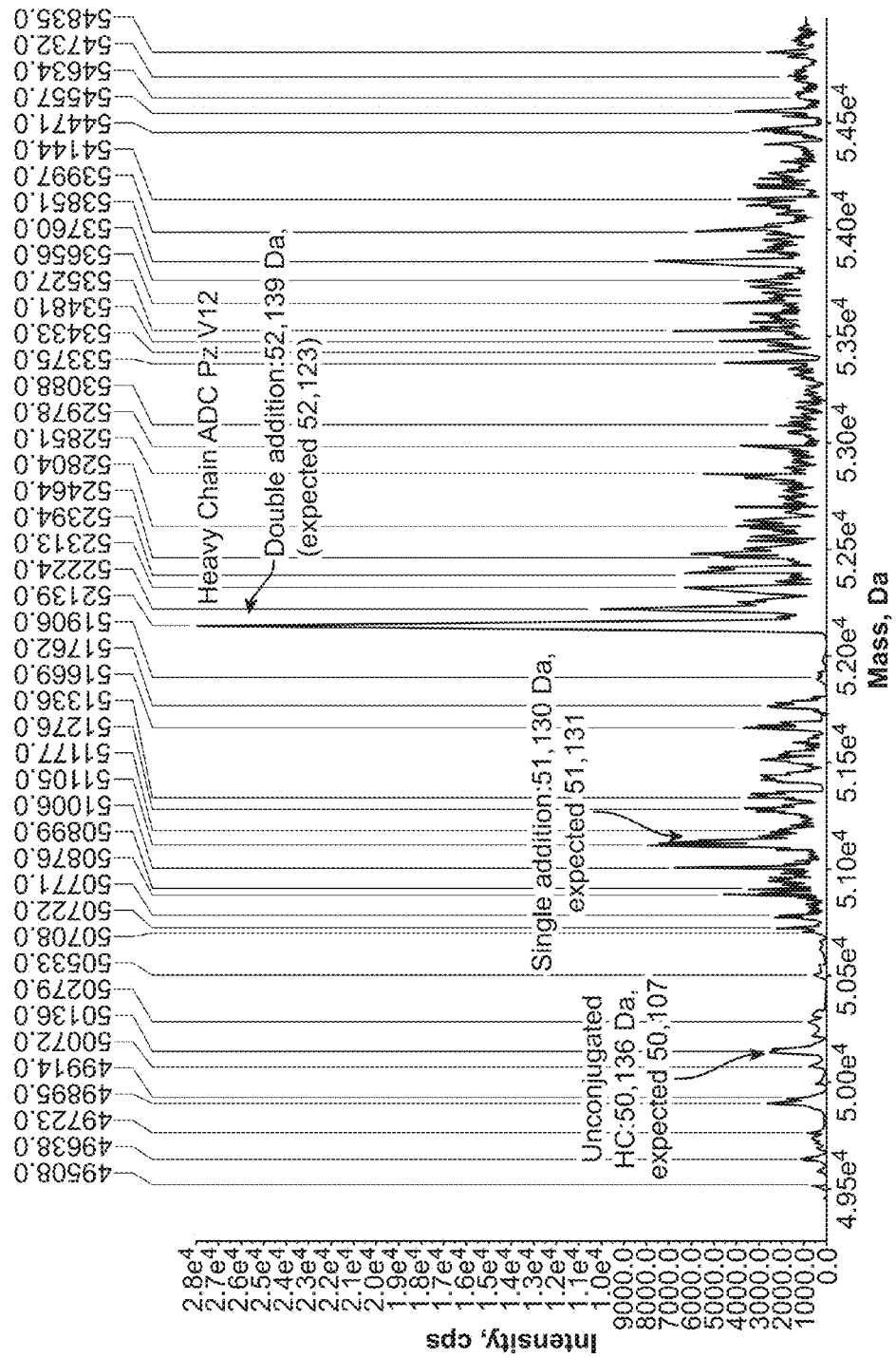

The conjugated antibody was reduced with 50 mM DTT at 37° C. for 30 min. Reduced samples were separated on a PLRP HPLC column at 70° C. in line with a 4000 QTRAP. MS1 spectra were obtained, and deconvoluted using Bioanalylst software. The light chain of the antibody showed no modification, while the heavy chain showed that the major product corresponded to the addition of two Pz-Ph-2PEG-Maytansine moieties (FIG. 21).

Example 31

Conjugation of Aldehyde-Tagged Antibody with Thio-Pz-2PEG-Maytansine

Thio-Pz-2PEG-Maytansine was synthesized according to Example 9 above.

Figure 22:
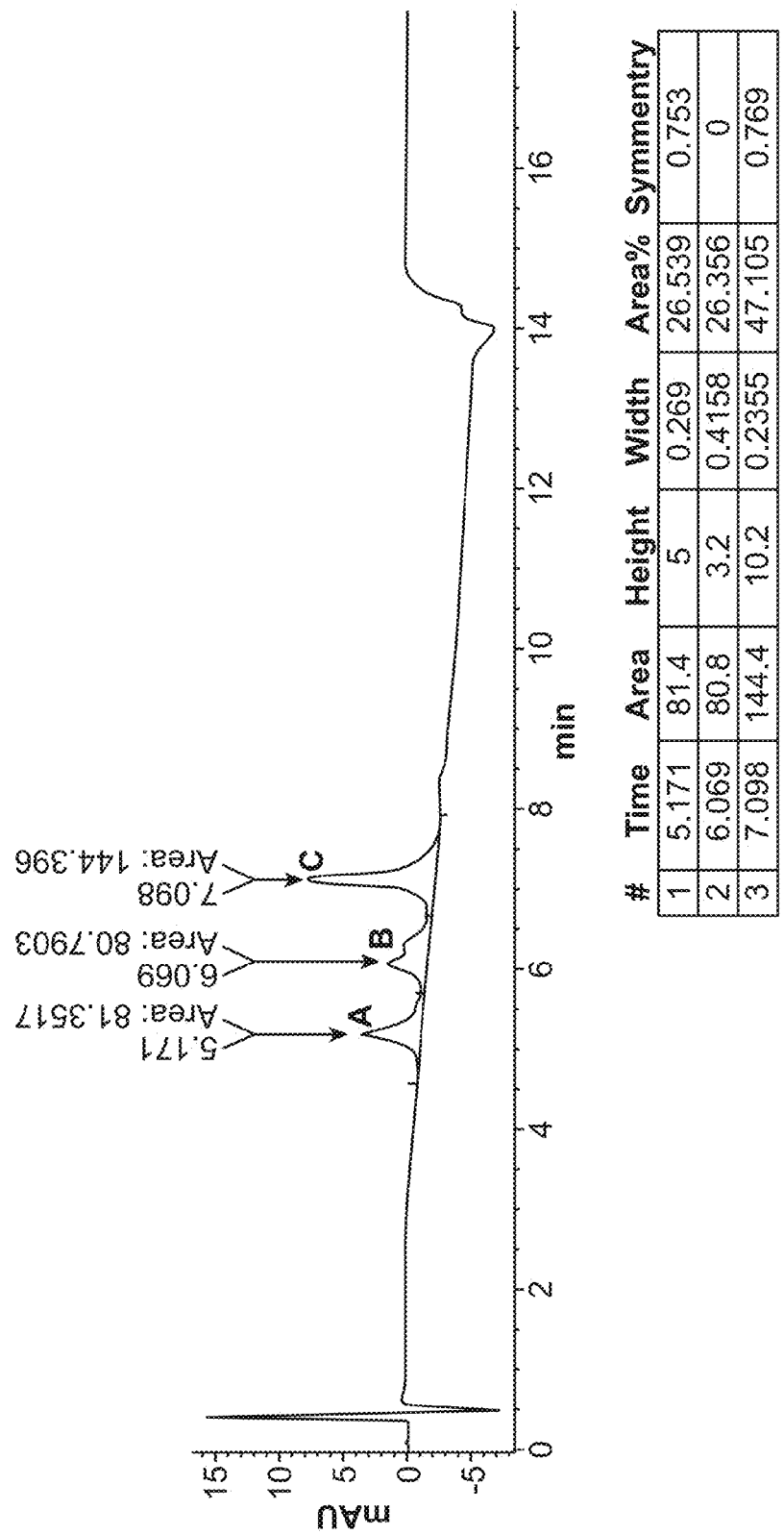
FIG. 22 shows a hydrophobic interaction column (HIC) trace of the reaction of thio-Pz-2PEG-Maytansine and an aldehyde-tagged antibody after 5.5 hours.

Aldehyde-tagged antibody (A) was reacted with thio-Pz-2PEG-Maytansine in PBS at pH 7, 37° C., with 2.5% DMA. The reaction mixture was analyzed by hydrophobic interaction column (HIC) after 5.5 hours (FIG. 22). Only the mono-conjugate (B and C) protein conjugates were observed. FIG. 22 shows a hydrophobic interaction column (HIC) trace of aldehyde-tagged antibody (A), protein with a drug antibody ratio (DAR) of 1 (B), and protein with DAR of 2 (C).

Figure 23:
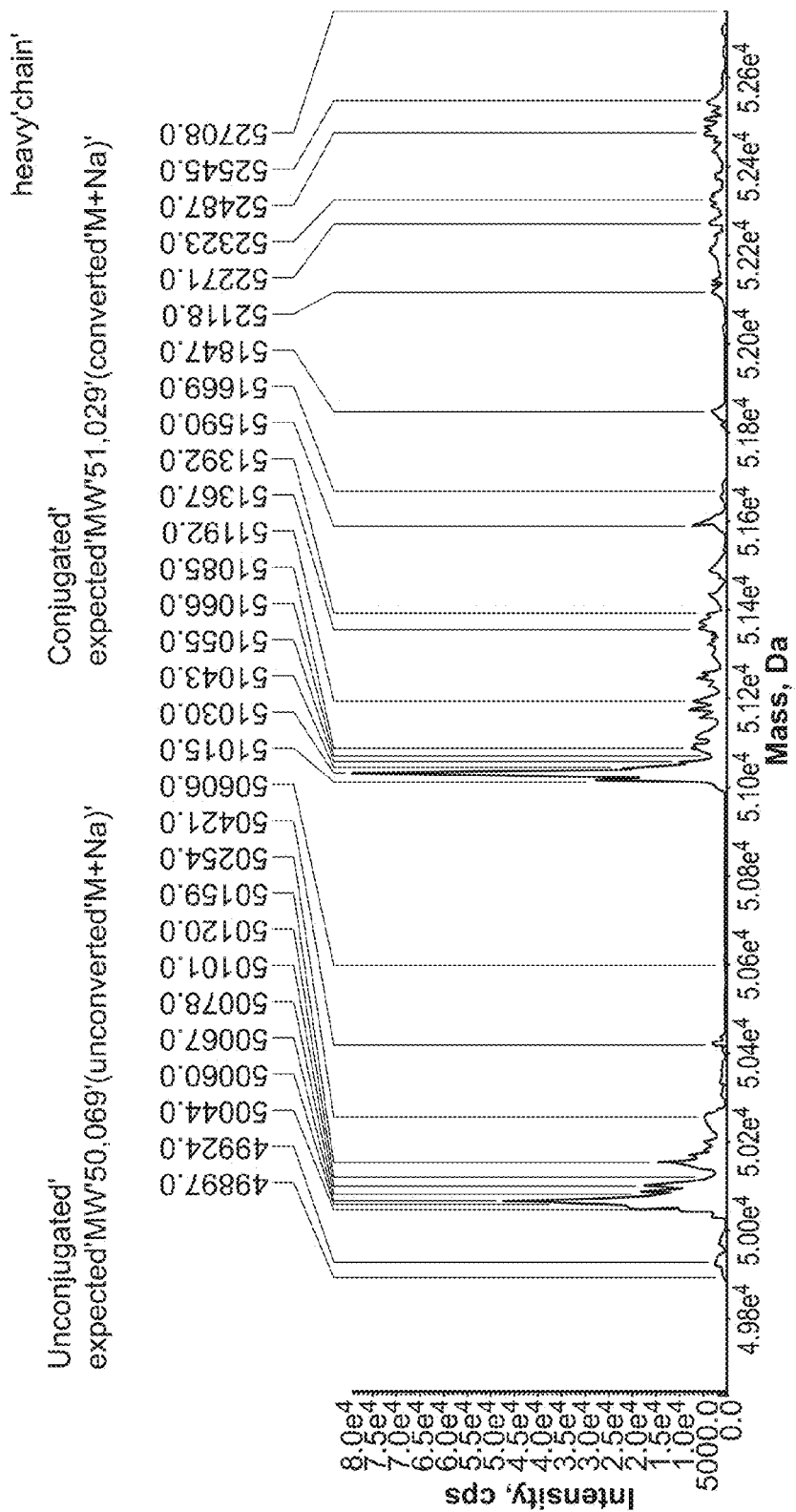
FIG. 23 shows an LC-MS analysis of IgG conjugated with thio-Pz-2PEG-Maytansine.
Figure 23:

The conjugated antibody was reduced with 50 mM DTT at 37° C. for 30 min. Reduced samples were separated on a PLRP HPLC column at 70° C. in line with a 4000 QTRAP. MS1 spectra were obtained, and deconvoluted using Bioanalylst software. The light chain of the antibody showed no modification, while the heavy chain showed the conjugated product (FIG. 23).

Additional Pyrazalinone Coupling Moieties

Additional pyrazalinone-based coupling moieties may be synthesized as described in the following examples.

Example 32

N-Bis-Pyrazalinone Coupling Moiety

An N-bis-pyrazalinone (N-bis-Pz) coupling moiety may be synthesized according to Scheme 19.

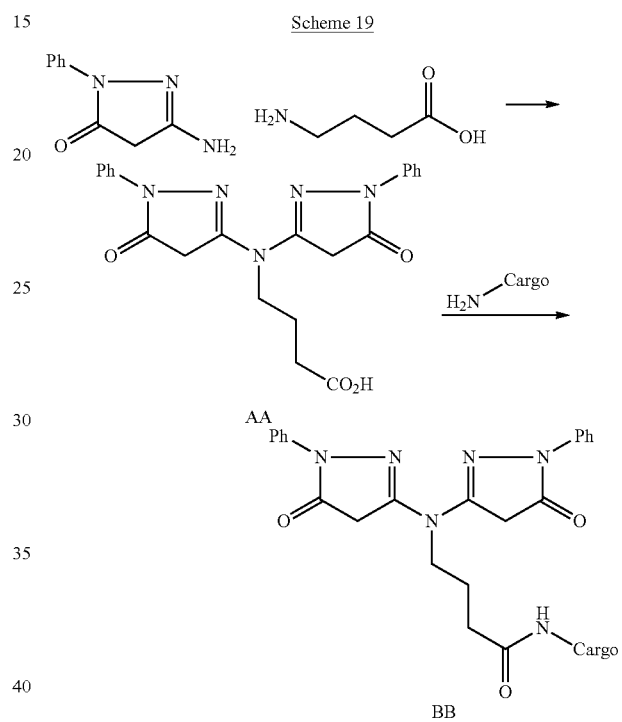

Using a modification of the procedure described in Graham, et al., *JACS*, 1954, 76, 3993-3995, 4-(bis(5-oxo-1-phenyl-4,5-dihydro-1H-pyrazol-3-yl)amino)butanoic acid is prepared by heating phenyl-3-amino-5-pyrazolone (20 g), γ-aminobutyric acid (25 g), in 20 mL n-butanol at reflux for three days. The precipitate is collected, acidified with acetic acid, and recrystallized from hot ethanol to yield 5 g of the desired product (AA). The cargo-carrying N-bis-pyrazolone (BB) is synthesized as follows. A 4 mL vial is charged with 2.0 μmol of Compound BB, 2 equiv H$_2$N-Cargo, 2 equiv DIPEA, and 1 equiv HATU in 200 μL DMA. The solution is stirred for 1 hour then purified by reverse phase chromatography.

Example 33

C-Bis-Pyrazalinone Coupling Moiety

A C-bis-pyrazalinone (C-bis-Pz) coupling moiety may be synthesized according to Schemes 20-22.

Scheme 20

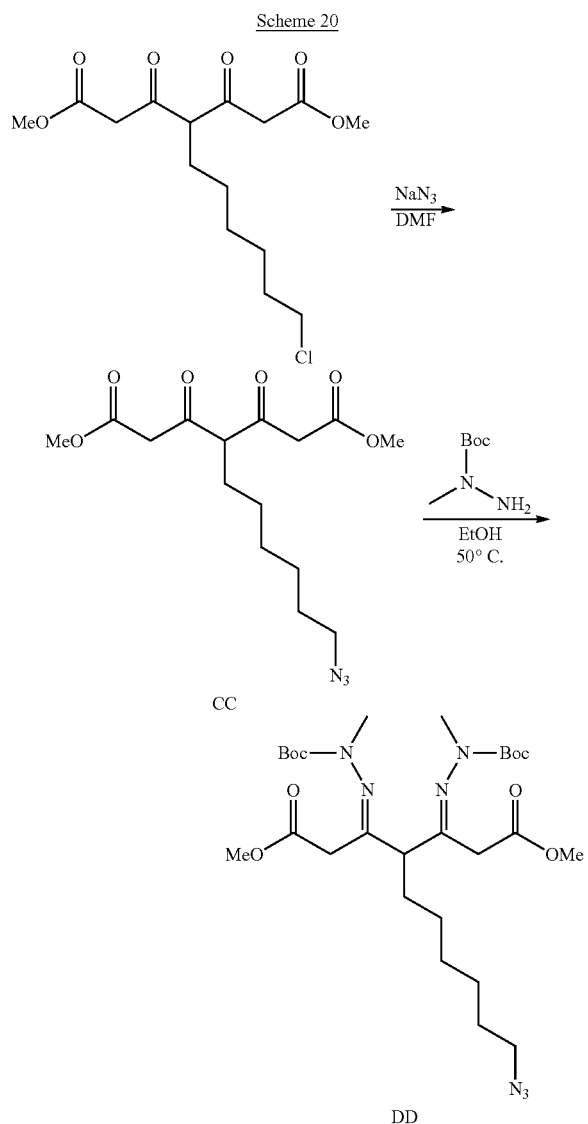

Scheme 21

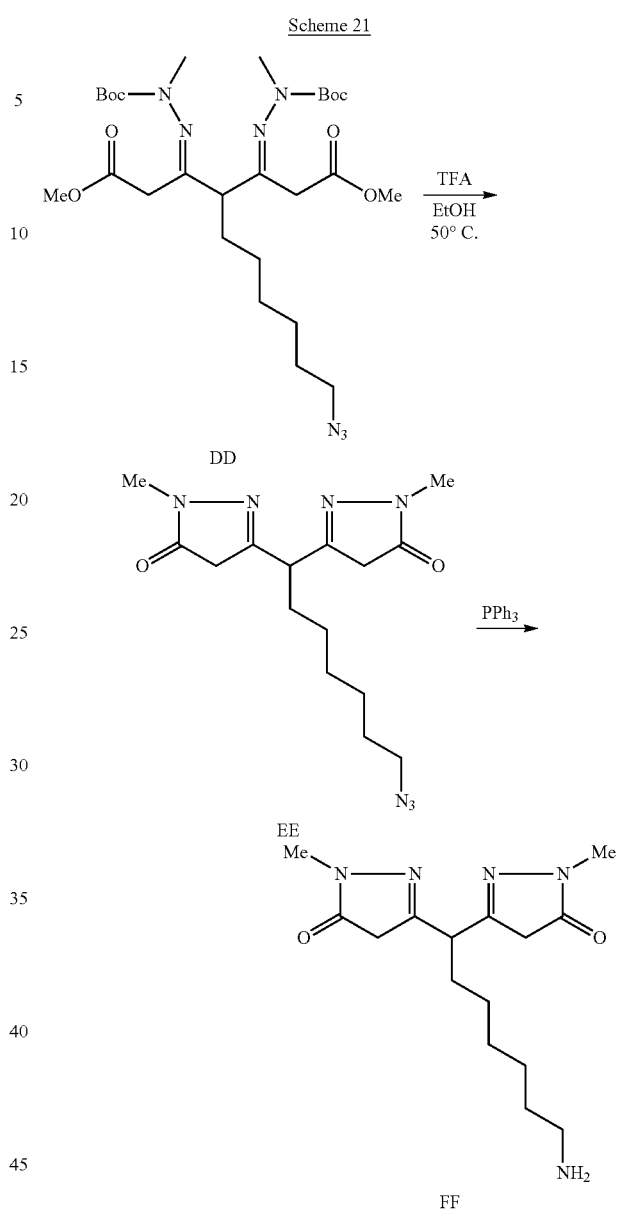

Dimethyl 4-(6-azidohexyl)-3,5-dioxoheptanedioate (CC)—A 300 mL round bottom flask is charged with 10 mmol of 4-(6-chlorohexyl)-3,5-dioxopimelic acid dimethyl ester (Reihm, et. al., *Org. Biomol. Chem.*, 2008, 6, 3079-3084), 25 mmol sodium azide, and 50 mL DMF. The reaction is stirred for 16 h and then quenched with water (200 mL). The reaction is extracted three times with $Et_2O$ (200 mL). The combined organics are then washed twice with water (150 mL) and once with brine (200 mL). The organic layer is dried over $MgSO_4$, filtered and the solvent is removed under reduced pressure. The crude reaction mixture is purified by flash chromatography affording the desired product (CC).

(3E,5E)-dimethyl 4-(6-azidohexyl)-3,5-bis(2-(tert-butoxycarbonyl)-2-methylhydrazono)heptanedioate (DD)—A 20 mL vial is charged with 10 mmol of Compound CC, N,N-Boc-1-methylhydrazine (25 mmol), and 10 mL ethanol. The reaction is stirred for 12 h at 50° C., concentrated in vacuo, and used without further purification.

3,3'-(7-azidoheptane-1,1-diyl)bis(1-methyl-1H-pyrazol-5(4H)-one) (EE)—A 20 mL vial is charged with 5 mmol of Compound DD and 10 mL of a 10% solution of TFA in ethanol. The reaction is stirred at room temperature for 1 hour and then is heated at 50° C. for 4 h. Upon cooling to room temperature, the reaction is concentrated in vacuo and azeotroped 3×5 mL toluene. The crude reaction mixture is purified by flash chromatography yielding the desired product (EE).

3,3'-(7-aminoheptane-1,1-diyl)bis(1-methyl-1H-pyrazol-5(4H)-one) (FF)—A 20 mL vial is charged with 5 mmol of Compound EE, 8 mmol triphenylphosphine, 30 equiv water, and 5 mL DCM. The reaction is stirred for 12 hours, concentrated in vacuo and purified by reverse phase flash chromatography using a 0-100% water:MeCN gradient yielding the desired product (FF).

Scheme 22

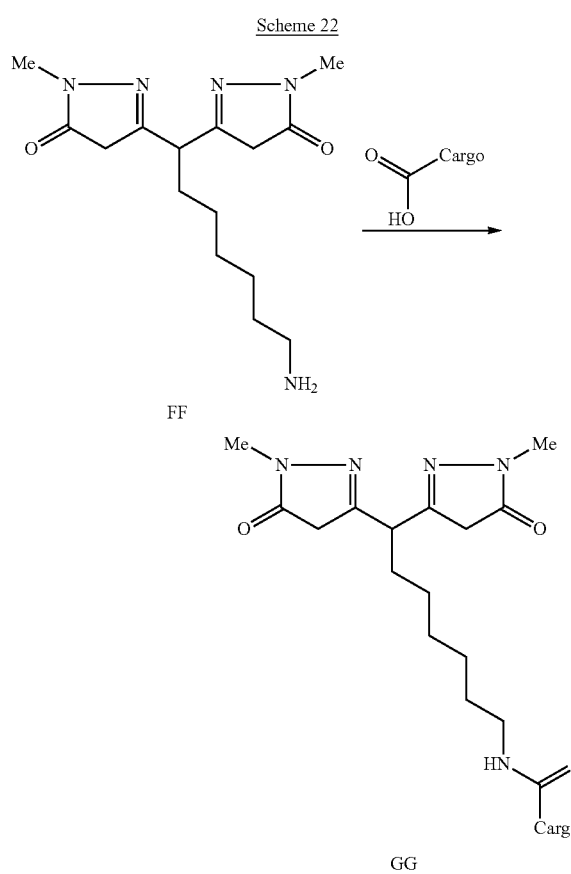

C-bis-Pz-cargo (GG)—A 4 mL vial is charged with 2.0 µmol of Compound FF, 1 equiv HO₂C-Cargo, 2 equiv DIPEA, and 1 equiv HATU in 200 µL DMA. The solution is stirred for 1 hour then purified by reverse phase chromatography using a 0-100% water:MeCN gradient yielding the desired product (GG).

Example 34

Pz-CH₂-Pz' Differential Payload

A bis-pyrazalinone (Pz-CH₂-Pz') coupling moiety conjugated to two different moieties may be synthesized according to Schemes 23 and 24.

Scheme 23

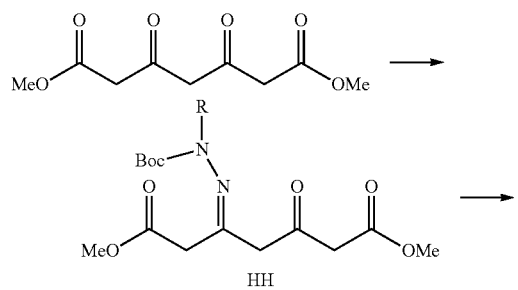

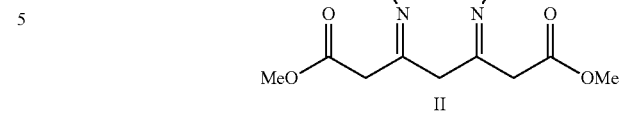
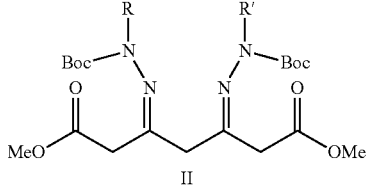

Compound HH—Compound HH is synthesized by mixing 2 mmol of the compound dimethyl 3,5-dioxoheptanedioate (Reihm, et. al., *Org. Biomol. Chem.*, 2008, 6, 3079-3084) with 1 mmol of the protected alkylhydrazine in 1 mL ethanol for 2 hours. The reaction is concentrated in vacuo and used without further purification.

Compound II—A 20 mL vial is charged with 0.5 mmol Compound HH, 0.5 mmol protected alkylhydrazine and 5 mL ethanol. The reaction is stirred for 2 hours, then concentrated in vacuo. The crude reaction is used without further purification.

Scheme 24

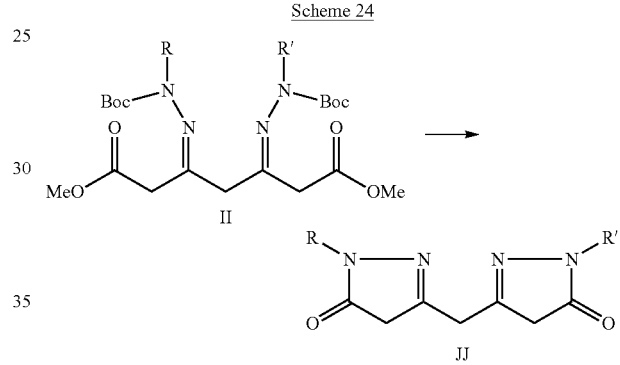

R = payload, alkyl, aryl, etc.
R' = different payload, alkyl, aryl, etc.

Compound JJ—A 4 mL vial is charged with 0.1 mmol Compound II and 1 mL DCM. To this solution, 100 µL water, 100 µL triisopropylsilane, 800 µL trifluoroacetic acid are added and the reaction is stirred for 1 hour at room temperature. The crude reaction is purified by reverse phase flash chromatography using a 0-100% water:MeCN gradient yielding the desired product (JJ).

Example 35

Malononitrile-Pz

A malononitrile-Pz coupling moiety may be synthesized according to Scheme 25.

Scheme 25

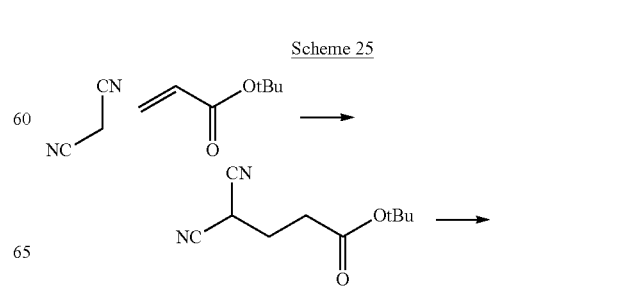

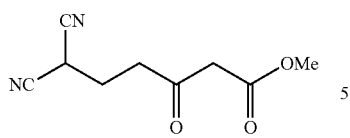

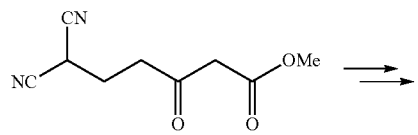

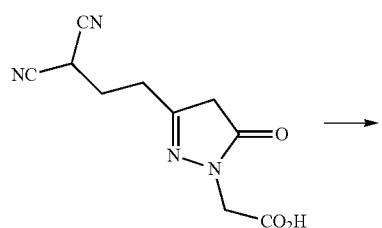

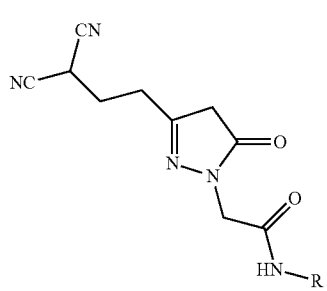

Example 36

α-Substituted-Pyrazalinone

An α-substituted-Pz coupling moiety may be synthesized according to Scheme 26.

Scheme 26

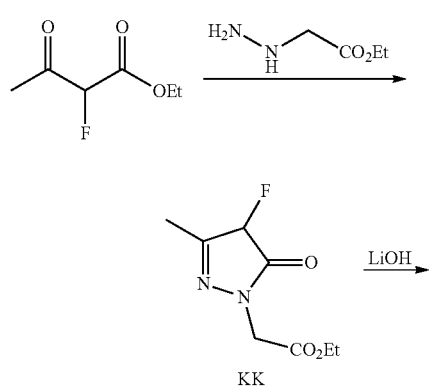

Ethyl 2-(4-fluoro-3-methyl-5-oxo-4,5-dihydro-1H-pyrazol-1-yl)acetate (KK) A solution of ethyl 2-fluoroacetoacetate (1.23 mmol), ethyl 2-hydrazinylacetate (1.23 mmol), triethylamine (17 μL, 0.124 mmol) in 10 mL ethanol is maintained at 50° C. for 2 h. The crude reaction is concentrated in vacuo and chromatographed on silica gel using a 33-60% hexane:ethyl acetate gradient yielding the desired product (KK).

2-(4-fluoro-3-methyl-5-oxo-4,5-dihydro-1H-pyrazol-1-yl)acetic acid (LL) Lithium hydroxide (10.7 mg) is added to a solution of Compound KK (0.207 mmol) in 1 mL of 2:3:1 THF:MeOH:water. The reaction is maintained for 2 h then partitioned between 40 mL water and 40 mL ethyl ether. The aqueous layer is acidified to pH 2 and washed 3×60 mL with DCM. The organic phases are combined, dried over MgSO$_4$, filtered, and concentrated in vacuo to yield the desired product (LL), which is used without further purification.

Fluoro-Pz-Cargo (MM)—COMU (6.8 mg) is added to a 0° C. solution of H$_2$N-2PEG-May (Compound 270) (18.5 mg, 0.0229 mmol), 2-(4-fluoro-3-methyl-5-oxo-4,5-dihydro-1H-pyrazol-1-yl)acetic acid (LL) (0.0153 mmol), 2,4,6-trimethylpyridine (0.0153 mmol) in 100 μL DMF. The reaction is maintained at 0° C. for 30 min then warmed to room temperature over 30 min. The resulting reaction mixture is diluted with 10 mL EtOAc then transferred to a separatory funnel. The organic phase is washed 3×10 mL 1M HCl, 3×10 mL saturated NaHCO$_3$, and 3×10 mL brine. The organic phase is dried over MgSO$_4$, filtered and concentrated in vacuo. The crude reaction is chromatographed on silica gel using a 5-12% methanol:DCM gradient to yield the desired product.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A conjugate comprising:
at least one modified amino acid residue of the formula:

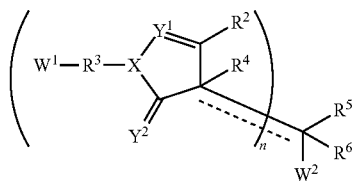

wherein
X is N, NH, O, S, CH or $CH_2$;
$Y^1$ and $Y^2$ are each independently selected from N, O and S;
n is 1 or 2;
$R^2$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
$R^3$ is selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl;
$R^4$ is optional and if present is selected from hydrogen, hydroxyl, halogen, cyano, alkyl, substituted alkyl, alkenyl, substituted alkenyl, alkynyl, substituted alkynyl, alkylalkoxy, substituted alkylalkoxy, acyl, carboxyl, and carboxyl ester;
$R^5$ is optional and if present is hydrogen or hydroxyl; and
$R^6$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl, wherein $W^1$ is a drug and $W^2$ is a polypeptide, wherein the dotted lines represent optional bonds, wherein when the dotted line between the $R^4$-carbon and the $R^5$-carbon is a double bond, n is 1 and $R^4$ and $R^5$ are not present, and wherein, when n is 2, the dotted line between the $R^4$-carbon and the $R^5$-carbon is not a double bond and $R^5$ is not present.

2. The conjugate of claim 1, wherein $Y^1$ is N.

3. The conjugate of claim 1, wherein $Y^2$ is O.

4. The conjugate of claim 1, wherein $R^2$ is alkyl, substituted alkyl, aryl or substituted aryl.

5. The conjugate of claim 1, wherein $R^2$ is methyl, t-butyl or aryl.

6. The conjugate of claim 1, wherein the dotted line between the $R^4$-carbon and the $R^5$-carbon is a double bond, n is 1, and $R^4$ and $R^5$ are not present.

7. The conjugate of claim 1, wherein the dotted line between the $R^4$-carbon and the $R^5$-carbon is not a double bond, n is 1, and $R^5$ is hydroxyl.

8. The conjugate of claim 1, wherein n is 2, the dotted line between the $R^4$-carbon and the $R^5$-carbon is not a double bond and $R^5$ is not present.

9. A pharmaceutical composition comprising:
a conjugate of claim 1; and
a pharmaceutically acceptable excipient.

10. A method of delivering a conjugate to a subject, the method comprising:
administering to the subject an effective amount of a conjugate of claim 1.

* * * * *

SEQUENCE LISTING

<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: Xaa is Cys or Ser.

<400> SEQUENCE: 1

Leu Xaa Thr Pro Ser Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 2

Leu Gly Thr Pro Ser Arg
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (8)..(8)
<223> OTHER INFORMATION: FORMYLATION

<400> SEQUENCE: 3

Gly Pro Ser Val Phe Pro Leu Gly Thr Pro Ser Arg
1               5                   10